US007235548B2

(12) United States Patent
Gouliaev et al.

(10) Patent No.: US 7,235,548 B2
(45) Date of Patent: *Jun. 26, 2007

(54) COMPOUNDS AND THEIR USE AS POSITIVE AMPA RECEPTOR MODULATORS

(75) Inventors: Alex Haaht Gouliaev, Vekso Sj (DK); Mogens Larsen, Smorum (DK); Thomas Varming, Charlottenlund (DK); Claus Mathiesen, Vekso (DK); Tina Holm Johansen, Smorum (DK); Jorgen Scheel-Kruger, Glostrup (DK); Gunnar M. Olsen, Frederiksberg (DK); Elsesbet Ostergaard Nielsen, Kobenhaven K (DK)

(73) Assignee: NeuroSearch A/S, Ballerup (DK)

( * ) Notice: Subject to any disclaimer, the term of this patent is extended or adjusted under 35 U.S.C. 154(b) by 681 days.

This patent is subject to a terminal disclaimer.

(21) Appl. No.: 10/642,224

(22) Filed: Aug. 18, 2003

(65) Prior Publication Data
US 2004/0043987 A1   Mar. 4, 2004

Related U.S. Application Data

(60) Division of application No. 09/641,814, filed on Aug. 18, 2000, now Pat. No. 6,943,159, which is a continuation of application No. PCT/DK99/00070, filed on Feb. 18, 1999.

(30) Foreign Application Priority Data
Feb. 18, 1998 (DK) ..................... 0226/98

(51) Int. Cl.
C07D 285/26 (2006.01)
C07D 417/12 (2006.01)
A61K 31/5415 (2006.01)

(52) U.S. Cl. ................. 514/223.2; 544/12; 544/13
(58) Field of Classification Search ............ 544/12, 544/13; 514/223.2
See application file for complete search history.

(56) References Cited

U.S. PATENT DOCUMENTS

| | | | |
|---|---|---|---|
| 3,261,794 A * | 7/1966 | Gordon et al. ............ 544/13 |
| 3,275,625 A | 9/1966 | Müller et al. | |
| 3,277,086 A | 10/1966 | Wei et al. | |
| 3,311,620 A | 3/1967 | Bell et al. | |
| 3,351,595 A | 11/1967 | de Stevens et al. | |
| 3,419,552 A | 12/1968 | Whitehead et al. | |
| 3,639,342 A | 2/1972 | Miyadera et al. | |
| 3,969,518 A | 7/1976 | Novello | |
| 4,184,039 A | 1/1980 | Soldati et al. | |
| 5,488,049 A | 1/1996 | Costa et al. | |
| 5,536,719 A | 7/1996 | Cordi et al. | |
| 6,015,800 A | 1/2000 | Nikam | |
| 6,943,159 B1 * | 9/2005 | Gouliaev et al. ........ 514/223.2 |

FOREIGN PATENT DOCUMENTS

| | | |
|---|---|---|
| DE | 1125938 | 3/1962 |
| DE | 147316 | 4/1969 |
| DE | 1470316 B | 4/1969 |
| DE | 1470316 B | 4/1969 |
| EP | 0692484 A1 | 1/1996 |
| EP | 0692484 A1 | 1/1996 |
| GB | 861367 | 2/1961 |
| GB | 863474 | 3/1961 |
| GB | 946864 | 1/1964 |
| GB | 1049322 | 11/1966 |
| HU | 176232 P | 1/1981 |
| HU | 176232 P | 2/1981 |
| JP | 6025984 A | 2/1985 |
| JP | 6025984 A | 2/1985 |
| NL | 296964 | 5/1965 |

(Continued)

OTHER PUBLICATIONS

Imai et al., *Communications*, pp. 851-852 (Oct. 1983).
Liang et al., *Journal*, 3074475, YHHPAL; Yaoxue Xebao; 10; 1963; 345-354; *Chem. Abstr*; 59; 13985; 1963.
Foeldi et al., *Journal*, 2700364, ACASA2; *Acta Chim. Acad. Sci. Hung.*; 38; 1963; 147.
E. Marchetti et al., *Journal*, 22139, BCFAAI; *Boll. Chim. Farm.*; IT; 104; 1965.
Alo et al., *J. Chem. Soc. Perkin Trans.*, No. 5, pp. 805-808 (1986).

(Continued)

Primary Examiner—Kahsay Habte
(74) Attorney, Agent, or Firm—Birch, Stewart, Kolasch & Birch, LLP

(57) ABSTRACT

The invention provides novel compounds represented by the general formula compound represented by the formula:

$$\text{[structure with substituents } R^2, R^3, R^4, R^5, R^6, R^7, R^8, X, Y, N]$$

wherein
the bond represented by the broken line may be a single, a double bond or absent;
and if the bond is absent, then the nitrogen is substituted with a hydrogen and $R^2$;
X represents $SO_2$ or $C=O$ or $CH_2$;
Y represents $—CH(R^4)—$, $—N(R^4)—$ or $—N(R^4)—CH_2—$, $O$;
and the meaning of $R^2$, $R^3$, $R^4$, $R^5$, $R^6$, $R^7$, and $R^8$ are as defined in the application The compounds are useful as positive modulators of the AMPA-receptor.

11 Claims, 17 Drawing Sheets

FOREIGN PATENT DOCUMENTS

| | | |
|---|---|---|
| WO | WO 932170 A1 | 10/1993 |
| WO | WO 9321170 A1 | 10/1993 |
| WO | WO 9321171 A1 | 10/1993 |
| WO | WO 9321171 A1 | 10/1993 |
| WO | WO 9515759 A1 | 6/1995 |
| WO | WO 9515759 A1 | 6/1995 |
| WO | WO 9638414 A1 | 12/1996 |
| WO | WO 9638414 A1 | 12/1996 |
| WO | WO 9707799 A1 | 3/1997 |
| WO | WO 9707799 A1 | 3/1997 |
| WO | WO 9726884 A1 | 7/1997 |
| WO | WO 9726884 A1 | 7/1997 |
| WO | WO 9736907 A1 | 10/1997 |
| WO | WO 9736907 A1 | 10/1997 |
| WO | WO 9749692 A1 | 12/1997 |
| WO | WO 9749692 A1 | 12/1997 |
| WO | WO 9812185 A1 | 3/1998 |
| WO | WO 9812185 A1 | 3/1998 |

OTHER PUBLICATIONS

Martin et al., *Journal of the Chemica Society*, pp. 2451-2458 (1974).
Raffa et al., Cardiovascular Activity of 1,2,4-benzothiadiazine 1,1-dio, *Farmaco, Ed. Sci*, vol. 29, No. 9, XP002107961, pp. 647-653 (1974).
Ghelardoni et al., Hydrogenolysis of 3,4-dihydro-1,2,4-benzothiadiazine 1,1-dioxides VII, *Ann. Chim.* (Rome), vol. 6 No. 5, XP002107962, pp. 373-384 (1972).
Wales et al., *The Journal of Pharmacology and Experimental Therapeutics*, vol. 164, No. 2, pp. 421-432 (1968).
Yale, *The Journal of Organic ChemistrY*, vol. 33, No. 6, pp. 2382-2385 (Jun. 1968).
Bierbaum et al., *Journal of Medicinal Chemistry*, vol. 6, pp. 272-275 (1963).
Kirkien-Rzseszotarski et al., *Journal of Heterocyclic Chemistry*, vol. 12, No. 1, pp. 155-159 (Feb. 1975).
Ghelardoni et al., *Ann Chim.* (Rome), Hydrogenloysis of 3,4-dihydro-1,2,4-benzothiadiazine-1,1-dioxides V, vol. 58, pp. 1402-1415, XP002107967 (1968).
Loynes et al., *Journal of Medicinal Chemistry*, vol. 8, pp. 691-694 (Mar. 9, 1965).
Short et al., *Journal of Organic Chemistry*, vol. 26, pp. 3428-3431 (Sep. 1961).
Ghelardoni et al., *Ann. chim.* (Rome), vol. 54, pp. 449-461, XP002107969 (1964).
Topliss et al., *Journal of Organic Chemistry*, vol. 26, pp. 3842-3850 (Oct. 1961).
Bernabei et al., *Farmaco, Ed. Sci.*, vol. 31, No. 7, XP002107959, pp. 508-516 (1976).

CAS printout for Werner et al. Chem Abs CA54:12148g.
Werner et al. Dihydrobenzothiadiazine 1,1-dioxides and their diuretic properties, 1960, Chem Abs CA54:12128g.
CAS printout for Orita et al. Chem Abs. 99:169045.
CAS printout for Di et al. Chem Abs. 88:145975.
CAS printout for Abramovitch et al. Chem Abs. 87:117236.
CAS printout for Ghelardoni et al. Chem Abs. 68:12959 and Chem Abs. 67:108649.
Gay, "Bendrofluazide Assay Including Extractive Alkylation for GC," Methodol. Surv. Biochem., 1978, pp. 133-139 No. 7.
Topliss et al., *Journal of Medicinal Chemistry*, vol. 15, No. 4, pp. 400-403 (1972).
Imai et al., *Communications*, pp. 851-852 (Oct. 1983).
Liang et al., *Journal*, 3074475, YHHPAL; Yaoxue Xebao; 10; 1963; 345-354; *Chem. Abstr*, 59; 13985; 1963.
Foeldi et al., *Journal*, 2700364, ACASA; *Acta Chim. Acad. Sci. Hung.*; 38; 1963; 147.
E. Marchetti et al., *Journal*, 22139, BCFAAI; *Boll. Chim. Farm.*; IT; 104; 1965.
Alo et al., *J. Chem. Soc. Perkin Trans.*, No. 5, pp. 805-808 (1986).
Martin et al., *Journal of the Chemica Society*, pp. 2451-2458 (1974).
Raffa et al., Cardiovascular Activity of 1, 2, 4-benzothiadiazine__1, 1-dio, *Farmaco, Ed. Sci*, vol. 29, No. 9, XP002107961, pp. 647-653 (1974).
Ghelardoni et al., Hydrogenolysis of 3,4-dihydro-1,2,4-benzothiadiazine 1, 1-dioxides__VII, *Ann. Chim.* (Rome), vol. 6 No. 5, XP002107962, pp. 373-384 (1972).
Wales et al., *The Journal of Pharmacology and Experimental Therapeutics*, vol. 164, No. 2, pp. 421-432 (1968).
Yale, *The Journal of Organic Chemistry*, vol. 33, No. 6, pp. 2382-2385 (Jun. 1968).
Bierbaum et al., *Journal of Medicinal Chemistry*, vol. 6, pp. 272-275 (1963).
Kirkien-Rzseszotarski et al., *Journal of Heterocyclic Chemistry*, vol. 12, No. 1, pp. 155-159 (Feb. 1975).
Ghelardoni et al., *Ann Chim.* (Rome), Hydrogenolysis of 3,4-dihydro-1,2,4-benzothiadiazine-1, 1-dioxides V, vol. 58, pp. 1402-1415, XP002107968 (1968).
Loynes et al., *Journal of Medicinal Chemistry*, vol. 8, pp. 691-694 (Mar. 9, 1965).
Short et al., *Journal of Organic Chemistry*, vol. 26, pp. 3428-3431 (Sep. 1961).
Ghelardoni et al., *Ann. chim.* (Rome), vol. 54, pp. 449-461, XP002107969 (1964).
Topliss et al., *Journal of Organic Chemistry*, vol. 26, pp. 3842-3850 (Oct. 1961).
Bemabei et al., *Farmaco, Ed. Sci.*, vol. 31, No. 7, XP002107959, pp. 508-516 (1976).

\* cited by examiner

COMPOUNDS AND THEIR USE AS POSITIVE AMPA RECEPTOR MODULATORS

This application is a divisional of application Ser. No. 09/641,814, filed Aug. 18, 2000, now U.S. Pat. No. 6,943,159 B1. Application Ser. No. 09/641,814 was a continuation of international application PCT/DK99/00070, filed Feb. 18, 1999. Applicants claim priority under 35 U.S.C. §120 to application Ser. No. 09/641,814 and to international application PCT/DK99/00070.

This invention relates to novel compounds useful as modulators of the AMPA sensitive glutamate receptors, pharmaceutical compositions comprising such compounds and their use in therapy.

BACKGROUND OF THE INVENTION

L-Glutamate is the major excitatory neurotransmitter in the mammalian central nervous system which activates several subtypes of ionotropic and metabotropic receptors. The ionotropic receptors can be divided into three subtypes, NMDA, AMPA and kainate receptors, based on structural and pharmacological differences.

Impairment of glutamatergic neurotransmission has been implicated in the learning and memory loss observed in numerous neurological disorders such as e.g. Alzheimer's decease, senile dementia, stroke (McEntee and Crook, *Psychopharmacology* 111:391–401 (1993)). It is widely accepted that learning and memory is related to the induction of long-term potentiation (LTP) which is a stable increase in the synaptic strength following repetitive high frequency stimulations. Experimental studies have shown that increasing the synaptic response mediated by AMPA receptors enhances the induction of LTP (Arai and Lynch, *Brain Research*, 598:173–184 (1992)). For the reasons stated above, compounds that stimulates AMPA receptor response in the brain, may induce improvements in the intellectual behavior and performance.

Activation of AMPA receptors with L-glutamate or the selective agonist AMPA leads to a rapid receptor desensitization; i.e. the receptor channel fails to open despite the continued presence of agonist. It is therefore possible to obtain an increase of the synaptic strength by attenuating the AMPA receptor desensitization normally elicited by the endogenous neurotransmitter L-glutamate.

In 1990 Ito et al. reported (*J. physiol.*, 424:533–543) that the nootropic drug aniracetam (N-anisoyl-2-pyrrolidinone) increased AMPA induced currents in oocytes injected with rat brain mRNA. In another study, it has been shown that 1-(1,3-benzodioxol-5-ylcarbonyl)-1,2,3,6-tetrahydropyridine, a compound that enhances synaptic transmission mediated by AMPA receptors, is effective at improving memory in experimental animals at a very high dose 120 mg/kg (Staubli et al., *Proc. Natl. Acad. Sci. USA*, 91:11158–11162 (1994)).

The benzothiadiazide cyclothiazide is a more potent and efficacious modulator of AMPA receptor current in-vitro than aniracetam (Johansen et al., *Mol. Pharmacol.* 48:946–955 (1995)). The effect of cyclothiazide on the kinetic properties of AMPA receptor currents appear to be by a different mechanism to that of aniracetam (Partin et al., *J. Neuroscience* 16:6634–6647 (1996)). However, cyclothiazide has no therapeutic potential for AMPA receptor modulation as it can not cross the blood-brain-barrier following peripheral administration. The low potency of know compounds also meets with higher demands for a high solubility due to the higher doses used for administration.

BACKGROUND ART

U.S. Pat. No. 5,488,049 describes the use of benzothiadiazide derivatives to treat memory and learning disorders. The compounds are structurally closely related to the compounds of the present invention. However the compounds of the present invention shows greater potentiation at lower concentrations. (FIG. 3 of U.S. Pat. No. 5,488,049)

U.S. Pat. No. 4,184,039 discloses benzothiadiazides for use in the promotion of hair growth;

DE 1470316 describes a method for producing some benzothiadiazides for use as additives in galvanizing baths.

In Synthesis (10), 183, p. 851 a method for preparation of benzothiadiazine-1,1-dioxides are described. The compounds are described as useful as antihypertensive and antimicrobial reagents.

In J. Med. Chem. (15, no. 4), 1972, p. 400–403 benzothiadiazine-1,1-dioxides are investigated for their π-substituents constants as structure activity study for anti hypertensive activity.

WO 9812185 describes benzothiadiazines of different structure as the compounds of the present invention.

OBJECT OF THE INVENTION

It is an object of the present invention to provide positive AMPA modulators which are useful in the treatment of disorders or diseases in mammals, including a human, and especially in the treatment of diseases and disorders which are responsive to modulation of the AMPA receptors in the brain.

Another object of the present invention is to provide a method of treating disorders or diseases of a mammal, including a human, responsive to AMPA receptor modulators which comprises administering to a mammal in need thereof a compound of the invention.

A third object of the present invention is to provide novel pharmaceutical compositions for the treatment of disorders or diseases of mammals, including a human, responsive to AMPA modulators.

Other objectives of the present invention will be apparent to the skilled person hereinafter.

SUMMARY OF THE INVENTION

The invention then, inter alia, comprises the following, alone or in combination:

A compound represented by the general formula:

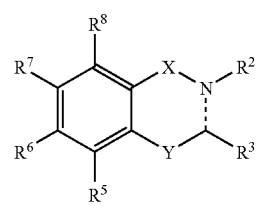

I wherein
the bond represented by the broken line may be a single, a double bond or absent;
and if the bond is absent, then the nitrogen is substituted with a hydrogen and $R^2$;
X represents $SO_2$ or C=O or $CH_2$;

Y represents —CH(R⁴)—, —N(R⁴)— or —N(R⁴)—CH₂—, O;

R² represents hydrogen, alkyl, cycloalkyl, aryl, benzyl; CO—R⁹ wherein
- R⁹ represents alkyl, cycloalkyl, benzyl, aryl; or R² together with R³ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups;

R³ represents hydrogen, cycloalkyl, alkyl, cycloalkylalkyl, haloalkyl, hydroxyalkyl, cyanoalkyl, alkoxyalkyl, alkoxy, haloalkoxy, acyl, alkyl-NR¹³R¹⁴, alkyl-S—R¹³ wherein
- R¹³ and R¹⁴ independently represents hydrogen, alkyl, cycloalkyl; or R¹³ and R¹⁴ together with the nitrogen to which they are attached forms a 3- to 8 membered heterocyclic ring structure;
- A carbocyclic 7- to 12-membered ring optionally substituted with halogen, alkyl, hydroxy or alkoxy; or
- A heterocyclic 3- to 8 membered ring optionally substituted with halogen, alkyl, hydroxy or alkoxy; and optionally the heterocyclic ring is fused to an aryl;
- Benzyl which is optionally substituted one or more times with substituents selected from the group consisting of halogen, cycloalkyl, alkyl, hydroxy, alkoxy, amino or thio, haloalkyl, hydroxyalkyl, alkoxyalkyl, alkylthio, alkylamino;
- Aryl which is optionally substituted one or more times with substituents selected from the group consisting of halogen, cycloalkyl, alkyl, hydroxy, alkoxy, amino or thio, haloalkyl, hydroxyalkyl, alkoxyalkyl, alkylthio, alkylamino; or R³ together with R² or R⁴ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups.

R⁴ represents hydrogen, alkyl, cycloalkyl, cycloalkylalkyl, aryl,
—CO—R¹⁰, or CO₂R¹⁰ wherein R¹⁰ represents hydrogen, cycloalkyl, alkyl, aryl or benzyl; or R⁴ together with R³ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups.

R⁵ represents hydrogen, halogen, alkyl, alkenyl, alkynyl, aryl,
—SO₂—NR¹¹R¹² wherein
- R¹¹ and R¹² independently represents hydrogen, alkyl, cycloalkyl, benzyl, aryl, or
- R¹¹ and R¹² together with the nitrogen to which they are attached forms a heterocyclic 3- to 8 membered ring structure optionally substituted with halogen, alkyl, hydroxy, alkoxy, amino or thio, aryl, benzyl, SO₂-alkyl, SO₂-aryl, SO₂-benzyl; and optionally the heterocyclic ring is fused to an aryl;

R⁶ represents hydrogen, halogen, alkyl, cyano, cyanoalkyl, nitro, alkoxy, haloalkoxy, haloalkyl, hydroxyalkyl, cycloalkyl, cyclohaloalkyl,
—NR¹⁵R¹⁶, NHSO₂—R¹⁵, NHSO₂-aryl wherein the aryl is optionally substituted one or more times with substituents selected from halogen, alkyl, cycloalkyl, hydroxy, alkoxy, amino, thio, CF₃, OCF₃, NO₂, aryl;

Aryl optionally substituted one or more times with substituents selected from the group consisting of alkyl, cycloalkyl, alkoxy, haloalkyl, haloalkoxy, hydroxyalkyl, alkoxyalkyl or amino;

HET optionally substituted one or more times with substituents selected from the group consisting of alkyl, cycloalkyl, alkoxy, halogen, haloalkyl, haloalkoxy;

-(alkyl)ₘ-S—R¹⁵; -(alkyl)ₘ-SO—R¹⁵; -(alkyl)ₘ-SO₂—R¹⁵; -(alkyl)ₘ-SO₂OR¹⁵, -(alkyl)ₘ-SO₂—NR¹⁵R¹⁶, -(alkyl)ₘ-NHCOR¹⁵, -(alkyl)ₘ-CONR¹⁵R¹⁶, -(alkyl)ₘ-CR'=NOR", -(alkyl)ₘ-CO—R¹⁵; -(alkyl)ₘ-CO₂—R¹⁵ wherein
- m is o or 1; and
- R' and R" independently represents hydrogen, alkyl, cycloalkyl, alkenyl, alkynyl, aryl, benzyl; and
- R¹⁵ and R¹⁶ independently represents hydrogen, alkyl, cycloalkyl, benzyl, aryl, or
- R¹⁵ and R¹⁶ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, SO₂-alkyl, SO₂-aryl, SO₂-benzyl; and optionally the heterocyclic ring is fused to an aryl;

R⁷ represents hydrogen, halogen, alkyl, cyano, cyanoalkyl, nitro, nitroalkyl; alkoxy, haloalkoxy, haloalkyl, hydroxyalkyl, cycloalkyl, cyclohaloalkyl,
—NR¹⁷R¹⁸, NHSO₂—R¹⁷, NHSO₂-aryl wherein the aryl is optionally substituted one or more times with substituents selected from halogen, alkyl, cycloalkyl, hydroxy, alkoxy, amino, thio, CF₃, OCF₃, NO₂, aryl;

-(alkyl)ₘ-S—R¹⁷; -(alkyl)ₘ-SO—R¹⁷; (alkyl)ₘ-SO₂—R¹⁷; -(alkyl)ₘ-SO₂R¹⁷, (alkyl)ₘ-SO₂—NR¹⁷R¹⁸, -(alkyl)ₘNHCOR¹⁷, -(alkyl)ₘCONR¹⁷R¹⁸, -(alkyl)ₘ-CR'=NOR", -(alkyl)ₘ-CO—R¹⁷; (alkyl)ₘCO₂—R¹⁷, wherein
- m is o or 1;
- and R' and R" independently represents hydrogen, alkyl, cycloalkyl, alkenyl, alkynyl, aryl, benzyl; and
- R¹⁷ and R¹⁸ independently represents hydrogen, alkyl, cycloalkyl, benzyl, aryl, or R¹⁷ and R¹⁸ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, SO₂-alkyl, SO₂-aryl, SO₂-benzyl; and optionally the heterocyclic ring is fused to an aryl;

HET optionally substituted one or more times with substituents selected from halogen, alkyl, alkenyl, alkynyl, hydroxy, alkoxy, amino, thio, aryl, —S-alkyl, —S-aryl, SO-alkyl, SO-aryl, SO₂-alkyl, SO₂-aryl, SO₂NR¹⁷R¹⁸;

Aryl optionally substituted one or more times with substituents selected from the group consisting of
alkyl, alkenyl, alkynyl, hydroxy, alkoxy, hydroxyalkyl, halogen, haloalkyl, amino, NHCO-alkyl, nitro, OCF3, —SO₂—NR¹⁷R¹⁸, wherein R¹⁷ and R¹⁸ independently represents hydrogen, alkyl, cycloalkyl, benzyl, aryl, or R¹⁷ and R¹⁸ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, SO$_2$-alkyl, SO$_2$-aryl, SO$_2$-benzyl; and optionally the heterocyclic ring is fused to an aryl;

or $R^7$ together with $R^6$ or together with $R^8$ forms a 5- to 7-membered ring having the one of the following structures —O—(CH$_2$)n-O—; wherein n is 1, 2 or 3; —SO$_2$—NR—(CH$_2$)n- wherein n is 1 or 2; —SO—NR—(CH$_2$)$_n$— wherein n is 1 or 2; —SO$_2$—(CH$_2$)$_n$— wherein n is 2 or 3; —SO—(CH$_2$)$_n$— wherein n is 2 or 3; —CO—CH=CH—NH—; —CO—CH=CH—O—; —CO—(CH$_2$)$_n$—NH— wherein n is 1 or 2; —CO—NH—(CH$_2$)$_n$ wherein n is 1 or 2; —CO—(CH$_2$)$_2$—O—; —O—(CH$_2$)n-O—; wherein n is 1, 2 or 3;

$R^8$ represents hydrogen, alkyl, alkoxy, hydroxyalkyl, halogen, haloalkyl, CN, cyanoalkyl, nitro, nitroalkyl;

Aryl optionally substituted one or more times with substituents selected from the group consisting of halogen, CF$_3$, OCF$_3$, NO$_2$, alkyl, cycloalkyl, alkoxy;

HET optionally substituted one or more times with substituents selected from the group consisting of halogen, CF$_3$, OCF$_3$, NO$_2$, alkyl, cycloalkyl, alkoxy;

-(alkyl)$_m$-S—R$^{19}$; -(alkyl)$_m$-SO—R$^{19}$; -(alkyl)$_m$-SO$_2$—R$^{19}$; -(alkyl)$_m$-SO$_2$OR$^{19}$, (alkyl)$_m$-SO$_2$—NR$^{19}$R$^{20}$, -(alkyl)$_m$NHCOR$^{19}$, -(alkyl)$_m$CONR$^{19}$R$^{20}$, -(alkyl)$_m$-CR'=NOR", -(alkyl)$_m$-CO—R$^{19}$; (alkyl)$_m$-CO$_2$—R$^{19}$, and m is 0 or 1; and R' and R" independently represents hydrogen, alkyl, cycloalkyl, alkenyl, alkynyl, aryl, benzyl; and R$^{19}$ and R$^{20}$ independently represents hydrogen, alkyl, cycloalkyl, benzyl, aryl, or R$^{19}$ and R$^{20}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, SO$_2$-alkyl, SO$_2$-aryl, SO$_2$-benzyl; and optionally the heterocyclic ring is fused to an aryl;

provided that when the broken line in formula I represents a double bond and X represents SO$_2$ and Y represent NH and the compound is monosubstituted then it is not monosubstituted with R$^3$ representing OCH$_3$, methyl, pentyl, t-butyl, aminophenyl, 2-phenylethylene, phenethyl, cyclopentyl, cyclopentenyl, cyclohexyl, cyclohexenyl, norbornene, benzyl, thienyl, furyl, aryl, aryl substituted with 4-methyl, 4-methoxy, 4-chloro, 4-nitro or 3-nitro;

and when the compound is disubstituted with R$^3$ being methyl then R$^5$ is not Cl, CH$_3$; or then R$^7$ is not F, Cl, Br, I, CH$_3$ CF$_3$, nitro, SO$_2$N(CH$_3$)$_2$; or then R$^6$ is not Cl, Br, CH$_3$, CH$_3$, ethyl, methoxy;

or when R$^7$ is chloro then R$^3$ is not ethyl, butyl, sec-butyl, t-butyl, cyclobutyl, 2,2-dimethylpropyl, phenyl;

and when the compound is disubstituted then it is not with R$^6$=OMe, R$^3$=ethyl; R$^6$=methyl, R$^3$=propyl; R$^7$=SO$_2$NH$_2$, R$^6$=Cl; R$^7$=SO$_2$NH$_2$, R$^3$=phenyl; R$^7$=Br, R$^3$=phenyl;

And provided that when the compound is trisubstituted then it is not R$^3$=CH$_3$, R$^5$=NO$_2$, R$^7$=Cl; R$^3$=CH$_3$, R$^6$=NO$_2$, R$^7$=Cl; R$^3$=CH$_3$, R$^5$=NH$_2$, R$^7$=Cl;

and provided that when the broken line in formula I represents a single bond and X represents SO$_2$ and Y represent NH Then the compound is not a disubstituted compounds with R$^7$ or R$^6$ being chloro and R$^3$ being alkyl, cyclobutyl, cyclopropyl, cyclohexyl, cyclohexen, norbornenyl, norbornanyl, ethylthiomethyl, ethyloxymethyl, ethyloxyethyl, methyloxymethyl, methylamino, 2-chloroethyl, chloromethyl, dichloromethyl, trifluoromethyl, amino; the compound is not a trisubstituted compound with R$^3$ being CH$_3$ and R$^5$=isopropyl, R$^7$=F; R$^5$=ethyl, R$^7$=Cl; R$^5$=propyl, R$^7$=Cl; R$^5$=ethyl, R$^7$=F; R$^5$=methyl, R$^7$=Cl; R$^5$=ethyl , R$^7$=methyl; R$^5$=Cl, R$^7$=Methyl; R$^5$=methyl, R$^7$=Cl; R$^4$=methyl, R$^5$=ethyl; or trisubstituted with R$^4$=methyl, R$^5$=methyl , R$^7$=F;

A pharmaceutical composition comprising an therapeutically effective amount of a compound as above together with pharmaceutically acceptable carriers or expients;

The use of a compound represented by the general formula

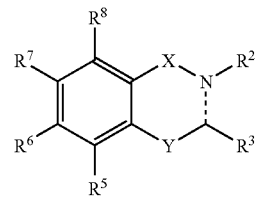

I wherein the bond represented by the broken line may be a single, a double bond or absent;

and if the bond is absent, then the nitrogen is substituted with a hydrogen and R$^2$;

X represents SO$_2$ or C=O or CH$_2$;

Y represents —CH(R$^4$)—, —N(R$^4$)— or —N(R$^4$)—CH$_2$—, O;

R$^2$ represents hydrogen, alkyl, cycloalkyl, aryl, benzyl; CO—R$^9$ wherein

R$^9$ represents alkyl, cycloalkyl, benzyl, aryl; or

R$^2$ together with R$^3$ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups;

R$^3$ represents hydrogen, cycloalkyl, alkyl, cycloalkylalkyl, haloalkyl, hydroxyalkyl, cyanoalkyl, alkoxyalkyl, alkoxy, haloalkoxy, acyl, alkyl-NR$^{13}$R$^{14}$, alkyl-S—R$^{13}$ wherein R$^{13}$ and R$^{14}$ independently represents hydrogen, alkyl, cycloalkyl; or R$^{13}$ and R$^{14}$ together with the nitrogen to which they are attached forms a 3- to 8 membered heterocyclic ring structure;

A carbocyclic 7- to 12-membered ring optionally substituted with halogen, alkyl, hydroxy or alkoxy; or A heterocyclic 3- to 8 membered ring optionally substituted with halogen, alkyl, hydroxy or alkoxy; and optionally the heterocyclic ring is fused to an aryl;

Benzyl which is optionally substituted one or more times with substituents selected from the group consisting of halogen, cycloalkyl, alkyl, hydroxy, alkoxy, amino or thio, haloalkyl, hydroxyalkyl, alkoxyalkyl, alkylthio, alkylamino;

Aryl which is optionally substituted one or more times with substituents selected from the group consisting of halogen, cycloalkyl, alkyl, hydroxy, alkoxy, amino or thio, haloalkyl, hydroxyalkyl, alkoxyalkyl, alkylthio, alkylamino; or R$^3$ together with R$^2$ or R$^4$ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups.

$R^4$ represents hydrogen, alkyl, cycloalkyl, cycloalkylalkyl, aryl, —CO—$R^{10}$, or $CO_2R^{10}$ wherein $R^{10}$ represents hydrogen, cycloalkyl, alkyl, aryl or benzyl; or $R^4$ together with $R^3$ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups.

$R^5$ represents hydrogen, halogen, alkyl, alkenyl, alkynyl, aryl,
—$SO_2$—$NR^{11}R^{12}$ wherein
  $R^{11}$ and $R^{12}$ independently represents hydrogen, alkyl, cycloalkyl, benzyl, aryl, or
  $R^{11}$ and $R^{12}$ together with the nitrogen to which they are attached forms a heterocyclic 3- to 8 membered ring structure optionally substituted with halogen, alkyl, hydroxy, alkoxy, amino or thio, aryl, benzyl, $SO_2$-alkyl, $SO_2$-aryl, $SO_2$-benzyl; and optionally the heterocyclic ring is fused to an aryl;

$R^6$ represents hydrogen, halogen, alkyl, cyano, cyanoalkyl, nitro, alkoxy, haloalkoxy, haloalkyl, hydroxyalkyl, cycloalkyl, cyclohaloalkyl,
—$NR^{15}R^{16}$, $NHSO_2$—$R^{15}$, $NHSO_2$-aryl wherein the aryl is optionally substituted one or more times with substituents selected from halogen, alkyl, cycloalkyl, hydroxy, alkoxy, amino, thio, $CF_3$, $OCF_3$, $NO_2$, aryl;

Aryl optionally substituted one or more times with substituents selected from the group consisting of alkyl, cycloalkyl, alkoxy, haloalkyl, haloalkoxy, hydroxyalkyl, alkoxyalkyl or amino;

HET optionally substituted one or more times with substituents selected from the group consisting of alkyl, cycloalkyl, alkoxy, halogen, haloalkyl, haloalkoxy;

-(alkyl)$_m$-S—$R^{15}$; -(alkyl)$_m$-SO—$R^{15}$; -(alkyl)$_m$-$SO_2$—$R^{15}$; -(alkyl)$_m$-$SO_2OR^{15}$, -(alkyl)$_m$-$SO_2$—$NR^{15}R^{16}$, -(alkyl)$_m$-NHCOR$^{15}$, -(alkyl)$_m$-CONR$^{15}R^{16}$, -(alkyl)$_m$-CR'=NOR", -(alkyl)$_m$-CO—$R^{15}$; -(alkyl)$_m$-$CO_2$—$R^{15}$ wherein
  m is 0 or 1; and
  R' and R" independently represents hydrogen, alkyl, cycloalkyl, alkenyl, alkynyl, aryl, benzyl; and
  $R^{15}$ and $R^{16}$ independently represents hydrogen, alkyl, cycloalkyl, benzyl, aryl, or
  $R^{15}$ and $R^{16}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl;

$R^7$ represents hydrogen, halogen, alkyl, cyano, cyanoalkyl, nitro, nitroalkyl; alkoxy, haloalkoxy, haloalkyl, hydroxyalkyl, cycloalkyl, cyclohaloalkyl,
—$NR^{17}R^{18}$, $NHSO_2$—$R^{17}$, $NHSO_2$-aryl wherein the aryl is optionally substituted one or more times with substituents selected from halogen, alkyl, cycloalkyl, hydroxy, alkoxy, amino, thio, $CF_3$, $OCF_3$, $NO_2$, aryl;
-(alkyl)$_m$-S—$R^{17}$; -(alkyl)$_m$-SO—$R^{17}$; (alkyl)$_m$-$SO_2$—$R^{17}$; -(alkyl)$_m$-$SO_2OR^{17}$, (alkyl)$_m$-$SO_2$—$NR^{17}R^{18}$, -(alkyl)$_m$NHCOR$^{17}$, -(alkyl)$_m$CONR$^{17}R^{18}$, -(alkyl)$_m$-CR'=NOR", -(alkyl)$_m$-CO—$R^{17}$; (alkyl)$_m$$CO_2$—$R^{17}$, wherein
  m is 0 or 1;
  and R' and R" independently represents hydrogen, alkyl, cycloalkyl, alkenyl, alkynyl, aryl, benzyl; and
  $R^{17}$ and $R^{18}$ independently represents hydrogen, alkyl, cycloalkyl, benzyl, aryl, or $R^{17}$ and $R^{18}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl;

HET optionally substituted one or more times with substituents selected from halogen, alkyl, alkenyl, alkynyl, hydroxy, alkoxy, amino, thio, aryl, —S-alkyl, —S-aryl, SO-alkyl, SO-aryl, $SO_2$-alkyl, $SO_2$-aryl, $SO_2NR^{17}R^{18}$;

Aryl optionally substituted one or more times with substituents selected from the group consisting of alkyl, alkenyl, alkynyl, hydroxy, alkoxy, hydroxyalkyl, halogen, haloalkyl, amino, NHCO-alkyl, nitro, OCF3, —$SO_2$—$NR^{17}R^{18}$, wherein $R^{17}$ and $R^{18}$ independently represents hydrogen, alkyl, cycloalkyl, benzyl, aryl, or $R^{17}$ and $R^{18}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl;

or $R^7$ together with $R^6$ or together with $R^8$ forms a 5- to 7-membered ring having the one of the following structures —O—$(CH_2)$n-O—; wherein n is 1, 2 or 3; —$SO_2$—NR—$(CH_2)$n- wherein n is 1 or 2; —SO—NR—$(CH_2)_n$— wherein n is 1 or 2; —$SO_2$—$(CH_2)_n$— wherein n is 2 or 3; —SO—$(CH_2)_n$— wherein n is 2 or 3; —CO—CH=CH—NH—; —CO—CH=CH—O—; —CO—$(CH_2)_n$—NH— wherein n is 1 or 2; —CO—NH—$(CH_2)_n$ wherein n is 1 or 2; —CO—$(CH_2)_2$—O—; —O—$(CH_2)$n-O—; wherein n is 1, 2 or 3;

$R^8$ represents hydrogen, alkyl, alkoxy, hydroxyalkyl, halogen, haloalkyl, CN, cyanoalkyl, nitro, nitroalkyl;

Aryl optionally substituted one or more times with substituents selected from the group consisting of halogen, $CF_3$, $OCF_3$, $NO_2$, alkyl, cycloalkyl, alkoxy;

HET optionally substituted one or more times with substituents selected from the group consisting of halogen, $CF_3$, $OCF_3$, $NO_2$, alkyl, cycloalkyl, alkoxy;

-(alkyl)$_m$-S—$R^{19}$; -(alkyl)$_m$-SO—$R^{19}$; -(alkyl)$_m$-$SO_2$—$R^{19}$; -(alkyl)$_m$-$SO_2OR^{19}$, (alkyl)$_m$-$SO_2$—$NR^{19}R^{20}$, -(alkyl)$_m$NHCOR$^{19}$, -(alkyl)$_m$CONR$^{19}R^{20}$, -(alkyl)$_m$-CR'=NOR", -(alkyl)$_m$-CO—$R^{19}$; (alkyl)$_m$-$CO_2$—$R^{19}$, and m is 0 or 1; and R' and R" independently represents hydrogen, alkyl, cycloalkyl, alkenyl, alkynyl, aryl, benzyl; and $R^{19}$ and $R^{20}$ independently represents hydrogen, alkyl, cycloalkyl, benzyl, aryl, or $R^{19}$ and $R^{20}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl;

for the manufacture of a medicament for the treatment of disorders or diseases responsive to modulation of the AMPA receptor complex.

A method for the treatment of disorders or diseases responsive to the modulation of the AMPA receptor complex wherein a therapeutically efficient amount of a compound represented by the general formula

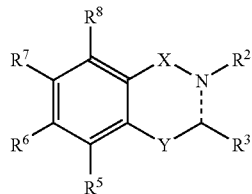

I wherein
the bond represented by the broken line may be a single, a double bond or absent;
and if the bond is absent, then the nitrogen is substituted with a hydrogen and $R^2$;
X represents $SO_2$ or C=O or $CH_2$;
Y represents —CH($R^4$)—, —N($R^4$)— or —N($R^4$)—$CH_2$—, O;
$R^2$ represents hydrogen, alkyl, cycloalkyl, aryl, benzyl; CO—$R^9$ wherein
  $R^9$ represents alkyl, cycloalkyl, benzyl, aryl; or
$R^2$ together with $R^3$ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups;
$R^3$ represents hydrogen, cycloalkyl, alkyl, cycloalkylalkyl, haloalkyl, hydroxyalkyl, cyanoalkyl, alkoxyalkyl, alkoxy, haloalkoxy, acyl, alkyl-$NR^{13}R^{14}$, alkyl-S—$R^{13}$
  wherein
    $R^{13}$ and $R^{14}$ independently represents hydrogen, alkyl, cycloalkyl; or $R^{13}$ and $R^{14}$ together with the nitrogen to which they are attached forms a 3- to 8 membered heterocyclic ring structure;
  A carbocyclic 7- to 12-membered ring optionally substituted with halogen, alkyl, hydroxy or alkoxy; or
  A heterocyclic 3- to 8 membered ring optionally substituted with halogen, alkyl, hydroxy or alkoxy; and optionally the heterocyclic ring is fused to an aryl;
  Benzyl which is optionally substituted one or more times with substituents selected from the group consisting of halogen, cycloalkyl, alkyl, hydroxy, alkoxy, amino or thio, haloalkyl, hydroxyalkyl, alkoxyalkyl, alkylthio, alkylamino;
  Aryl which is optionally substituted one or more times with substituents selected from the group consisting of halogen, cycloalkyl, alkyl, hydroxy, alkoxy, amino or thio, haloalkyl, hydroxyalkyl, alkoxyalkyl, alkylthio, alkylamino; or
$R^3$ together with $R^2$ or $R^4$ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups.
$R^4$ represents hydrogen, alkyl, cycloalkyl, cycloalkylalkyl, aryl, —CO—$R^{10}$, or $CO_2R^{10}$ wherein $R^{10}$ represents hydrogen, cycloalkyl, alkyl, aryl or benzyl; or
$R^4$ together with $R^3$ and together with the atoms to which they are attached, forms a 4- to 7-membered ring optionally substituted one or more times with substituents selected from halogen, alkyl, alkenyl, alkynyl, hydroxy, alkoxy, amino or thio and optionally containing one or more heteroatoms and optionally containing carbonyl groups.
$R^5$ represents hydrogen, halogen, alkyl, alkenyl, alkynyl, aryl,
  —$SO_2$—$NR^{11}R^{12}$ wherein
    $R^{11}$ and $R^{12}$ independently represents hydrogen, alkyl, cycloalkyl, benzyl, aryl, or
    $R^{11}$ and $R^{12}$ together with the nitrogen to which they are attached forms a heterocyclic 3- to 8 membered ring structure optionally substituted with halogen, alkyl, hydroxy, alkoxy, amino or thio, aryl, benzyl, $SO_2$-alkyl, $SO_2$-aryl, $SO_2$-benzyl; and optionally the heterocyclic ring is fused to an aryl;
$R^6$ represents hydrogen, halogen, alkyl, cyano, cyanoalkyl, nitro, alkoxy, haloalkoxy, haloalkyl, hydroxyalkyl, cycloalkyl, cyclohaloalkyl,
  —$NR^{15}R^{16}$, $NHSO_2$—$R^{15}$, $NHSO_2$-aryl wherein the aryl is optionally substituted one or more times with substituents selected from halogen, alkyl, cycloalkyl, hydroxy, alkoxy, amino, thio, $CF_3$, $OCF_3$, $NO_2$, aryl;
  Aryl optionally substituted one or more times with substituents selected from the group consisting of alkyl, cycloalkyl, alkoxy, haloalkyl, haloalkoxy, hydroxyalkyl, alkoxyalkyl or amino;
  HET optionally substituted one or more times with substituents selected from the group consisting of alkyl, cycloalkyl, alkoxy, halogen, haloalkyl, haloalkoxy;
  -(alkyl)$_m$-S—$R^{15}$; -(alkyl)$_m$-SO—$R^{15}$; -(alkyl)$_m$-$SO_2$—$R^{15}$; -(alkyl)$_m$-$SO_2OR^{15}$, -(alkyl)$_m$-$SO_2$—$NR^{15}R^{16}$, -(alkyl)$_m$-$NHCOR^{15}$, -(alkyl)$_m$-$CONR^{15}R^{16}$, -(alkyl)$_m$-CR'=NOR", -(alkyl)$_m$-CO—$R^{15}$; -(alkyl)$_m$-$CO_2$—$R^{15}$
  wherein
    m is o or 1; and
    R' and R" independently represents hydrogen, alkyl, cycloalkyl, alkenyl, alkynyl, aryl, benzyl; and
    $R^{15}$ and $R^{16}$ independently represents hydrogen, alkyl, cycloalkyl, benzyl, aryl, or
    $R^{15}$ and $R^{16}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl;
$R^7$ represents hydrogen, halogen, alkyl, cyano, cyanoalkyl, nitro, nitroalkyl; alkoxy, haloalkoxy, haloalkyl, hydroxyalkyl, cycloalkyl, cyclohaloalkyl,
  —$NR^{17}R^{18}$, $NHSO_2$—$R^{17}$, $NHSO_2$-aryl wherein the aryl is optionally substituted one or more times with substituents selected from halogen, alkyl, cycloalkyl, hydroxy, alkoxy, amino, thio, $CF_3$, $OCF_3$, $NO_2$, aryl;
  -(alkyl)$_m$-S—$R^{17}$; -(alkyl)$_m$-SO—$R^{17}$; (alkyl)$_m$-$SO_2$—$R^{17}$; -(alkyl)$_m$-$SO_2OR^{17}$, (alkyl)$_m$-$SO_2$—$NR^{17}R^{18}$, -(alkyl)$_m$$NHCOR^{17}$, -(alkyl)$_m$$CONR^{17}R^{18}$, -(alkyl)$_m$-CR'=NOR", -(alkyl)$_m$-CO—$R^{17}$; (alkyl)$_m$$CO_2$—$R^{17}$,
  wherein m is o or 1;

and R' and R" independently represents hydrogen, alkyl, cycloalkyl, alkenyl, alkynyl, aryl, benzyl; and $R^{17}$ and $R^{18}$ independently represents hydrogen, alkyl, cycloalkyl, benzyl, aryl, or $R^{17}$ and $R^{18}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl;

HET optionally substituted one or more times with substituents selected from halogen, alkyl, alkenyl, alkynyl, hydroxy, alkoxy, amino, thio, aryl, —S-alkyl, —S-aryl, SO-alkyl, SO-aryl, $SO_2$-alkyl, $SO_2$-aryl, $SO_2NR^{17}R^{18}$;

Aryl optionally substituted one or more times with substituents selected from the group consisting of alkyl, alkenyl, alkynyl, hydroxy, alkoxy, hydroxyalkyl, halogen, haloalkyl, amino, NHCO-alkyl, nitro, $OCF_3$, —$SO_2$—$NR^{17}R^{18}$, wherein $R^{17}$ and $R^{18}$ independently represents hydrogen, alkyl, cycloalkyl, benzyl, aryl, or $R^{17}$ and $R^{18}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl;

or $R^7$ together with $R^6$ or together with $R^8$ forms a 5- to 7-membered ring having the one of the following structures —O—$(CH_2)$n-O—; wherein n is 1, 2 or 3; —$SO_2$—NR—$(CH_2)$n- wherein n is 1 or 2; —SO—NR—$(CH_2)_n$— wherein n is 1 or 2; —$SO_2$—$(CH_2)_n$— wherein n is 2 or 3; —SO—$(CH_2)_n$— wherein n is 2 or 3; —CO—CH=CH—NH—; —CO—CH=CH—O—; —CO—$(CH_2)_n$—NH— wherein n is 1 or 2; —CO—NH—$(CH_)_n$ wherein n is 1 or 2; —CO—$(CH_2)_2$—O—; —O—$(CH_2)$n-O—; wherein n is 1, 2 or 3;

$R^8$ represents hydrogen, alkyl, alkoxy, hydroxyalkyl, halogen, haloalkyl, CN, cyanoalkyl, nitro, nitroalkyl;

Aryl optionally substituted one or more times with substituents selected from the group consisting of halogen, $CF_3$, $OCF_3$, $NO_2$, alkyl, cycloalkyl, alkoxy;

HET optionally substituted one or more times with substituents selected from the group consisting of halogen, $CF_3$, $OCF_3$, $NO_2$, alkyl, cycloalkyl, alkoxy;

-(alkyl)$_m$-S—$R^{19}$; -(alkyl)$_m$-SO—$R^{19}$; -(alkyl)$_m$-$SO_2$—$R^{19}$; -(alkyl)$_m$-$SO_2OR^{19}$, (alkyl)$_m$-$SO_2$—$NR^{19}R^{20}$, -(alkyl)$_m$NHCOR$^{19}$, -(alkyl)$_m$CONR$^{19}R^{20}$, -(alkyl)$_m$-CR'=NOR", -(alkyl)$_m$-CO—$R^{19}$;

(alkyl)$_m$-$CO_2$—$R^{19}$, and m is 0 or 1; and R' and R" independently represents hydrogen, alkyl, cycloalkyl, alkenyl, alkynyl, aryl, benzyl; and $R^{19}$ and $R^{20}$ independently represents hydrogen, alkyl, cycloalkyl, benzyl, aryl, or $R^{19}$ and $R^{20}$ together with the nitrogen to which they are attached forms a heterocyclic 3- to 8 membered ring structure optionally substituted with halogen, alkyl, alkenyl, alkynyl, hydroxy, alkoxy, amino or thio, aryl, benzyl, $SO_2$-alkyl, $SO_2$-aryl, $SO_2$-benzyl; and optionally the heterocyclic ring is fused to an aryl, is administered.

DETAILED DISCLOSURE OF THE INVENTION

The invention provides novel compounds of formula I as shown above. Preferred embodiments of the invention are compounds of formula I as above wherein $R^2$ represents
hydrogen, alkyl, cycloalkyl, phenyl, benzyl;
or $R^2$ together with $R^3$ and together with the atoms to which they are attached forms a 5- to 6-membered ring optionally substituted one or more times with substituents selected from halogen, alkyl, hydroxy, alkoxy, amino or thio; and optionally containing one or more heteroatoms and optionally containing carbonyl groups;

$R^3$ represents
hydrogen, cycloalkyl, cycloalkylalkyl, alkyl, haloalkyl, alkoxy, a carbocyclic 7- to 10-membered ring; a heterocyclic 5- to 6 membered ring; benzyl; aryl;
or $R^3$ together with $R^2$ or $R^4$ forms a 5- to 6-membered ring;

$R^4$ represents
hydrogen, alkyl,
or $R^4$ together with $R^3$ and together with the atoms to which they are attached, forms a 5- to 6-membered ring; optionally substituted one or more times with substituents selected from halogen, alkyl, alkenyl, alkynyl, hydroxy, alkoxy, amino or thio and optionally containing one or more heteroatoms and optionally containing carbonyl groups.

$R^5$ represents
hydrogen, halogen, alkyl, alkenyl, alkynyl, phenyl, —$SO_2$—$NR^{11}R^{12}$ wherein
$R^{11}$ and $R^{12}$ independently represents hydrogen, alkyl, cycloalkyl, benzyl, aryl, or $R^{11}$ and $R^{12}$ together with the nitrogen to which they are attached forms a heterocyclic 5- to 6-membered ring structure;

$R^6$ represents
hydrogen, Br, F, I, cycloalkyl, alkyl, alkoxy, alkoxyalkyl, Phenyl optionally substituted one or more times with substituents selected from the group consisting of alkyl, alkoxy;
HET;
—S—$R^{15}$; —SO—$R^{15}$; —$SO_2$—$R^{15}$; —$SO_2OR^{15}$, —$SO_2$—$NR^{15}R^{16}$, —NHCOR$^{15}$, —CON$^{15}R^{16}$, —CR'=NOR", —CO—$R^{15}$; —$CO_2$—$R^{15}$, wherein
R' and R" independently represents hydrogen, alkyl, cycloalkyl, phenyl, benzyl; and
$R^{15}$ and $R^{16}$ independently represents hydrogen, alkyl, cycloalkyl, benzyl, aryl, or $R^{15}$ and $R^{16}$ together with the nitrogen to which they are attached forms a heterocyclic 3- to 8 membered ring structure optionally substituted with halogen, alkyl, alkenyl, alkynyl, hydroxy, alkoxy, amino or thio, phenyl, benzyl, $SO_2$-alkyl, $SO_2$-aryl, $SO_2$-benzyl; and optionally the heterocyclic ring is fused to an aryl;

$R^7$ represents
hydrogen, Br, F, I, alkyl, cyano, cyanoalkyl, nitro, nitroalkyl, alkoxy, haloalkoxy, haloalkyl, hydroxyalkyl, cycloalkyl, cyclohaloalkyl, -(alkyl)m-$NR^{17}R^{18}$, $NHSO_2$—$R^{17}$, —S—$R^{17}$; —SO—$R^{17}$; —$SO_2$—$R^{17}$; —$SO_2OR^{17}$, —$SO_2$—$NR^{17}R^{18}$, NHCOR$^{17}$, CONR$^{17}R^{18}$, CR'=NOR", —CO—$R^{17}$; —$CO_2$—$R^{17}$,
wherein R' and R" independently represents hydrogen, alkyl, cycloalkyl, phenyl, benzyl; and
$R^{17}$ and $R^{18}$ independently represents hydrogen, alkyl, cycloalkyl, benzyl, aryl, or $R^{17}$ and $R^{18}$ together with the nitrogen to which they are attached forms a heterocyclic 3- to 8 membered ring structure optionally substituted with alkyl, $SO_2$-alkyl, $SO_2$-aryl, $SO_2$-benzyl; and optionally the heterocyclic ring is fused to an aryl;

HET optionally substituted one or more times with substituents selected from halogen, alkyl, phenyl, $SO_2NR^{17}R^{18}$;

Phenyl optionally substituted one or more times with substituents selected from the group consisting of
alkyl, hydroxy, alkoxy, halogen, haloalkyl, amino, NHCO-alkyl, nitro, OCF3, $—SO_2—NR^{17}R^{18}$ wherein $R^{17}$ and $R^{18}$ independently represents hydrogen, alkyl, cycloalkyl, benzyl, aryl, or $R^{17}$ and $R^{18}$ together with the nitrogen to which they are attached forms a heterocyclic 3- to 8 membered ring structure optionally substituted with halogen, alkyl, $SO_2$-alkyl, $SO_2$-aryl, $SO_2$-benzyl; and optionally the heterocyclic ring is fused to an aryl;
or $R^7$ together with $R^6$ or together with $R^8$ forms a 5- to 7-membered ring having the one of the following structures $—O—(CH_2)n-O—$; wherein n is 1, 2 or 3; $—SO_2—NR—(CH_2)n-$ wherein n is 1 or 2; $—SO—NR—(CH_2)_n—$ wherein n is 1 or 2; $—SO_2—(CH_2)_n—$ wherein n is 2 or 3; $—SO—(CH_2)_n—$ wherein n is 2 or 3; $—CO—CH=CH—NH—$; $—CO—CH=CH—O—$; $—CO—(CH_2)_n—NH—$ wherein n is 1 or 2; $—CO—NH—(CH_2)_n$ wherein n is 1 or 2; $—CO—(CH_2)_2—O—$; $—O—(CH_2)n-O—$; wherein n is 1, 2 or 3;

$R^8$ represents hydrogen, alkyl, alkoxy, hydroxyalkyl, halogen, haloalkyl, CN, cyanoalkyl, nitro, nitroalkyl;

Phenyl optionally substituted one or more times with substituents selected from the group consisting of
alkyl, cycloalkyl, alkoxy;
HET;
$—S—R^{19}$; $—SO—R^{19}$; $—SO_2—R^{19}$; $—SO_2OR^{19}$, $—SO_2—NR^{19}R^{20}$, $NHCOR^{19}$, $—CONR^{19}R^{20}$, CR'=NOR", $—CO—R^{19}$; $—CO_2—R^{19}$, wherein
R' and R" independently represents hydrogen, alkyl, cycloalkyl, phenyl, benzyl; and
$R^{19}$ and $R_{20}$ independently represents hydrogen, alkyl, cycloalkyl, benzyl, aryl, heterocyclic 3- to 8 membered ring structure optionally substituted with halogen, alkyl, alkenyl, alkynyl, hydroxy, alkoxy, amino or thio, phenyl, benzyl, $SO_2$-alkyl, $SO_2$-aryl, $SO_2$-benzyl; and optionally the heterocyclic ring is fused to an aryl;
provided that when X represents $SO_2$ and Y represents N and the broken line represents a single bond then neither of $R^7$ or $R^6$ are chloro when $R^2$, $R^4$, $R^5$, $R^8$ and the remaining of $R^6$ and $R^7$ are all hydrogen; and provided that $R^3$ can represent $CH_3$ only when $R^5$ is hydrogen or $R^7$ is not sulfamoyl;

and provided that when X represents $SO_2$ and Y represents N and the broken line represents a double bond then neither of $R^7$ or $R^6$ are chloro when $R^2$, $R^4$, $R^5$, $R^8$ and the remaining of and $R^7$ are all hydrogen; and provided that $R^2$, $R^4$, $R^5$, $R^6$, $R^7$ and $R^8$ are not all hydrogen; and provided that the compound is not disubstituted with $R^3$ is being $CH_3$ when $R^7$ is fluoro, bromo, iodo, $CF_3$, $CH_3$, $NO_2$, $SO_2N(CH_3)_2$, or $R^6$ is bromo, $CF_3$, $CH_3$, ethyl, methoxy; or $R^5$ is chloro, $CH_3$; or $R^8$ is chloro; and provided that the compound is not
3-ethyl-6-methoxy-1,2,4-benzothiadiazine-1,1-dioxide;
3-propyl-6-methyl-1,2,4-benzothiadiazine-1,1-dioxide;
3-ethyl-6-methoxy-1,2,4-benzothiadiazine-1,1-dioxide;
3-phenyl-7-bromo-1,2,4-benzothiadiazine-1,1-dioxide;
3-phenyl-7-sulfamoyl-1,2,4-benzothiadiazine-1,1-dioxide;
5-bromo-7-chloro-3-methyl-1,2,4-benzothiadiazine-1,1-dioxide;
5-iodo-7-chloro-3-methyl-1,2,4-benzothiadiazine-1,1-dioxide;
5-nitro-7-chloro-3-methyl-1,2,4-benzothiadiazine-1,1-dioxide;
6-nitro-7-chloro-3-methyl-1,2,4-benzothiadiazine-1,1-dioxide; or
6-amino-7-chloro-3-methyl-1,2,4-benzothiadiazine-1,1-dioxide;

A more preferred embodiment of the invention is a compound of formula I as above, wherein $R^2$ represents hydrogen, alkyl, cycloalkyl;

or $R^2$ together with $R^3$ forms a 5- to 6-membered ring; optionally substituted one or more times with substituents selected from halogen, alkyl, alkenyl, alkynyl, hydroxy, alkoxy, amino or thio and optionally containing one or more heteroatoms and optionally containing carbonyl groups;

And a preferred embodiment is wherein
$R^3$ represents
hydrogen, cycloalkyl, alkyl, haloalkyl, alkoxy, a carbocyclic 7- to 10-membered ring; a heterocyclic 5- to 6 membered ring; benzyl; aryl;
or
$R^3$ together with $R^2$ or $R^4$ forms a 5- to 6-membered ring; optionally substituted one or more times with substituents selected from halogen, alkyl, alkenyl, alkynyl, hydroxy, alkoxy, amino or thio and optionally containing one or more heteroatoms and optionally containing carbonyl groups.

And another preferred embodiment is wherein
$R^4$ represents
hydrogen, alkyl, or $R^4$ together with $R^3$ and together with the atoms to which they are attached, forms a 5- to 6-membered ring optionally substituted one or more times with substituents selected from halogen, alkyl, alkenyl, alkynyl, hydroxy, alkoxy, amino or thio and optionally containing one or more heteroatoms and optionally containing carbonyl groups.

And another preferred embodiment is wherein
$R^5$ represents
hydrogen, halogen, alkyl, alkenyl, alkynyl, phenyl, $—SO_2—NR^{11}R^{12}$ wherein
$R^{11}$ and $R^{12}$ independently represents hydrogen, alkyl, cycloalkyl, benzyl, aryl, or $R^{11}$ and $R^{12}$ together with the nitrogen to which they are attached forms a heterocyclic 3- to 8 membered ring structure;

And another preferred embodiment is wherein
$R^1$ represents
hydrogen, halogen, cycloalkyl, alkyl, alkoxy, alkoxyalkyl,
Aryl optionally substituted one or more times with substituents selected from the group consisting of alkyl, alkoxy;
HET;
$—S—R^{15}$; $—SO—R^{15}$; $—SO_2—R^{15}$; $—SO_2OR^{15}$, $—SO_2—NR^{15}R^{16}$, $—NHCOR^{15}$, $—CONR^{15}R^{16}$, $—CR'=NOR"$, $—CO—R^{15}$; $—CO_2—R^{15}$, wherein
R' and R" independently represents hydrogen, alkyl, cycloalkyl, phenyl, benzyl; and
$R^{15}$ and $R^{16}$ independently represents hydrogen, alkyl, cycloalkyl, benzyl, aryl, or $R^{15}$ and $R^{16}$ together with the nitrogen to which they are attached forms a heterocyclic 3- to 8 membered ring structure optionally substituted with halogen, alkyl, alkenyl, alkynyl, hydroxy, alkoxy, amino or thio, phenyl, benzyl, SO$_2$-alkyl, SO$_2$-aryl, SO$_2$-benzyl; and optionally the heterocyclic ring is fused to an aryl;

And another preferred embodiment is wherein

R$^7$ represents hydrogen, halogen, alkyl, cyano, cyanoalkyl, nitro, alkoxy, haloalkoxy, haloalkyl, hydroxyalkyl, cycloalkyl, cyclohaloalkyl, -(alkyl)m-NR$^{17}$R$^{18}$, NHSO$_2$—R$^{17}$, —S—R$^{17}$; —SO—R$^{17}$; —SO$_2$—R$^{17}$; —SO$_2$OR$^{17}$, —SO$_2$—NR$^{17}$R$^{18}$, NHCOR$^{17}$, CONR$^{17}$R$^{18}$, CR'=NOR", —CO—R$^{17}$; —CO$_2$—R$^{17}$, wherein R' and R" independently represents hydrogen, alkyl, cycloalkyl, phenyl, benzyl; and R$^{17}$ and R$^{18}$ independently represents hydrogen, alkyl, cycloalkyl, benzyl, aryl, or R$^{17}$ and R$^{18}$ together with the nitrogen to which they are attached forms a heterocyclic 3- to 8 membered ring structure optionally substituted with alkyl, SO$_2$-alkyl, SO$_2$-aryl, SO$_2$-benzyl; and optionally the heterocyclic ring is fused to an aryl;

HET optionally substituted one or more times with substituents selected from halogen, alkyl, phenyl, SO$_2$NR$^{17}$R$^{18}$;

Phenyl optionally substituted one or more times with substituents selected from the group consisting of alkyl, hydroxy, alkoxy, halogen, haloalkyl, amino, NHCO-alkyl, nitro, OCF3, —SO$_2$—NR$^{17}$R$^{18}$ wherein R$^{17}$ and R$^{18}$ independently represents hydrogen, alkyl, cycloalkyl, benzyl, aryl, or R$^{17}$ and R$^{18}$ together with the nitrogen to which they are attached forms a heterocyclic 3- to 8 membered ring structure optionally substituted with halogen, alkyl, SO$_2$-alkyl, SO$_2$-aryl, SO$_2$-benzyl; and optionally the heterocyclic ring is fused to an aryl;

or

R$^7$ together with R$^6$ or together with R$^8$ forms a 5- to 7-membered ring having the one of the following structures —O—(CH$_2$)n-O—; wherein n is 1, 2 or 3; —SO$_2$—NR—(CH$_2$)n- wherein n is 1 or 2; —SO—NR—(CH$_2$)n- wherein n is 1 or 2; —SO$_2$—(CH$_2$)n- wherein n is 2 or 3; —SO—(CH$_2$)n- wherein n is 2 or 3; —CO—CH=CH—NH—; —CO—CH=CH—O—; —CO—(CH$_2$)$_n$—NH— wherein n is 1 or 2; —CO—NH—(CH$_2$)$_n$ wherein n is 1 or 2; —CO—(CH$_2$)$_2$—O—; O—(CH$_2$)$_n$—O—; wherein n is 1, 2 or 3;

And another preferred embodiment is wherein

R$^8$ represents hydrogen, alkyl, alkoxy, hydroxyalkyl, halogen, haloalkyl, CN, cyanoalkyl, nitro, nitroalkyl;

Phenyl optionally substituted one or more times with substituents selected from the group consisting of alkyl, cycloalkyl, alkoxy;

HET;

—S—R$^{19}$; —SO—R$^{19}$; —SO$_2$—R$^{19}$; —SO$_2$OR$^{19}$, —SO$_2$—NR$^{19}$R$^{20}$, NHCOR$^{19}$, —CONR$^{19}$R$^{20}$, CR'=NOR", —CO—R$^{19}$; —CO$_2$—R$^{19}$, wherein R' and R" independently represents hydrogen, alkyl, cycloalkyl, phenyl, benzyl; and R$^{19}$ and R$^{20}$ independently represents hydrogen, alkyl, cycloalkyl, benzyl, aryl, or R$^{19}$ and R$^{20}$ together with the nitrogen to which they are attached forms a heterocyclic 3- to 8 membered ring structure optionally substituted with halogen, alkyl, alkenyl, alkynyl, hydroxy, alkoxy, amino or thio, phenyl, benzyl, SO$_2$-alkyl, SO$_2$-aryl, SO$_2$-benzyl; and optionally the heterocyclic ring is fused to an aryl;

An especially preferred embodiments is a compounds of formula I as above wherein X represents SO$_2$; Y represents N and the broken line represents a single bond; R$^2$ represents H;

R$^3$ represents cycloalkyl, a carbocyclic 7- to 10-membered ring; a heterocyclic 5- to 6 membered ring;

R$^4$ represents H;

R$^5$ represents H;

R$^6$ represents hydrogen, alkyl or halogen;

R$^7$ represents cyanoalkyl, nitroalkyl, haloalkyl,

-(alkyl)$_m$-SO—R$^{17}$; (alkyl)$_m$-SO$_2$—R$^{17}$; (alkyl)$_m$-SO$_2$—NR$^{17}$R$^{18}$, -(alkyl)$_m$CONR$^{17}$R$^{18}$, -(alkyl)$_m$-CR'=NOR", -(alkyl)$_m$-CO—R$^{17}$; (alkyl)$_m$CO$_2$—R$^{17}$, wherein m is o or 1;

R' and R" independently represents hydrogen, alkyl, cycloalkyl, phenyl, benzyl; and R$^{17}$ and R$^{18}$ independently represents hydrogen, alkyl, cycloalkyl, benzyl, aryl, or R$^{17}$ and R$^{18}$ together with the nitrogen to which they are attached forms a heterocyclic 3- to 8 membered ring structure optionally substituted with alkyl, SO$_2$-alkyl, SO$_2$-aryl, SO$_2$-benzyl; and optionally the heterocyclic ring is fused to an aryl; or

HET;

or

R$^7$ together with R$^6$ or together with R$^8$ forms a 5- to 7-membered ring having the one of the following structures —O—(CH$_2$)n-O—; wherein n is 1, 2 or 3; —SO$_2$—NR—(CH$_2$)n- wherein n is 1 or 2; —SO—NR—(CH$_2$)n- wherein n is 1 or 2; —SO$_2$—(CH$_2$)n- wherein n is 2 or 3; —SO—(CH$_2$)n- wherein n is 2 or 3; —CO—CH=CH—NH—; —CO—CH=CH—O—; —CO—(CH$_2$)$_n$—NH— wherein n is 1 or 2; —CO—NH—(CH$_2$)$_n$ wherein n is 1 or 2; —CO—(CH$_2$)$_2$—O—; O—(CH$_2$)$_n$—O—; wherein n is 1, 2 or 3;

R$^8$ represents alkyl, halogen, cyanoalkyl, nitroalkyl, haloalkyl,

-(alkyl)$_m$-SO—R$^{17}$; (alkyl)$_m$-SO$_2$—R$^{17}$; (alkyl)$_m$-SO$_2$—NR$^{17}$R$^{18}$, -(alkyl)$_m$CONR$^{17}$R$^{18}$, -(alkyl)$_m$-CR'=NOR", -(alkyl)$_m$-CO—R$^{17}$; (alkyl)$_m$CO$_2$—R$^{17}$, wherein m is o or 1;

R' and R" independently represents hydrogen, alkyl, cycloalkyl, phenyl, benzyl; and R$^{17}$ and R$^{18}$ independently represents hydrogen, alkyl, cycloalkyl, benzyl, aryl, or R$^{17}$ and R$^{18}$ together with the nitrogen to which they are attached forms a heterocyclic 3- to 8 membered ring structure optionally substituted with alkyl, SO$_2$-alkyl, SO$_2$-aryl, SO$_2$-benzyl; and optionally the heterocyclic ring is fused to an aryl; or

HET;

Special embodiments of the invention are the following all referring to formula I as above.

An embodiment of the invention is wherein

R$^3$ represents hydrogen, cyclopropyl, cyclopentyl, cyclohexyl, methyl, ethyl, propyl, isopropyl, CF$_3$, ethoxy, norbornene, norbornane, adamantane, benzyl; phenyl;

or

R$^3$ together with R$^2$ or R$^4$ and together with the atoms to which they are attached forms a 5-membered ring;

Another embodiment of the invention is wherein $R^4$ represents
hydrogen, methyl, ethyl; or $R^4$ together with $R^3$ and together with the atoms to which they are attached, forms a 5-membered ring;

And another embodiment of the invention is wherein
$R^5$ represents
hydrogen, chloro, bromo, methyl, phenyl, —$SO_2NH_2$;

And another embodiment of the invention is wherein
$R^6$ represents
hydrogen, 2-methoxyphenyl, 2-pyridyl, 3-pyridyl, methyl, methoxy, chloro or bromo;

And another embodiment of the invention is wherein
$R^7$ represents
hydrogen, chloro, bromo, methyl, 1-hydroxyethyl, acetyl, —($CH_3$)C=N—OH, $CONH_2$, $CO_2$-ethyl, cyano, phenyl, 2-N-acetylaminophenyl, 2-nitrophenyl, 2-methoxyphenyl, 4-trifluoromethyl-2-methoxyphenyl, 2,4-dimethoxyphenyl, 2-N,N-dimethylsulfamoylphenyl, 2-chlorophenyl, 2-fluorophenyl, 3-hydroxyphenyl, 2-pyridyl, 3-pyridyl, 2-pyrimidyl, 2-furyl, 3-furyl, 2-thienyl, 2-(N-methyl)-imidazolyl, 5-triazolyl, 4-phenyl-triazol-5-yl, 5-methyl-1,2,4-oxadiazol-3-yl, $CH_3CONH$—, $CH_3SO_2NH$—, $NO_2$, $SO_2OH$, phenyl-$SO_2$—, sulfamoyl, N,N-dimethylsulfamoyl, N,N-diethylsulfamoyl, N-phenyl-N-methyl-sulfamoyl, N-cyclohexyl-sulfamoyl, —$SO_2$-heterocyclic ring, wherein the heterocyclic rings are selected from the group of piperidine, pyrrolidine, 1,2,5,6-tetrahydropyridine, tetrahydroquinoline, N-methylpiperazine, N-sulfonylmethyl-piperazine, morpholine;

And another embodiment is wherein
$R^8$ represents
hydrogen, methyl, hydroxymethyl, 2-methoxyphenyl, 3-methoxyphenyl, 2-pyridyl, methoxy;

Especially preferred embodiments are a compounds represented by formula I as above
wherein X is $SO_2$ and Y is N and the broken line represents a single bond and $R^2$ represents hydrogen or $CH_3$;
and $R^3$ represents cyclohexyl, cyclopentyl, norbornene, norbornane, adamantane, phenyl, ethoxy;
and $R^4$ represents hydrogen or $CH_3$;
and $R^5$ represents hydrogen, $CH_3$, phenyl, sulfamoyl, chloro, bromo,
and $R^6$ represents hydrogen, $CH_3$, 2-methoxyphenyl, methoxy, chloro, bromo, 2-pyridyl, 3-pyridyl;
and $R^7$ represents
hydrogen, chloro, bromo, methyl, 1-hydroxyethyl, acetyl, —($CH_3$)C=N—OH, $CONH_2$, $CO_2$-ethyl, cyano, phenyl, 2-N-acetylaminophenyl, 2-nitrophenyl, 2-methoxyphenyl, 4-trifluoromethyl-2-methoxyphenyl, 2,4-dimethoxyphenyl, 2-N, N-dimethylsulfamoylphenyl, 2-chlorophenyl, 2-fluorophenyl, 3-hydroxyphenyl, 2-pyridyl, 3-pyridyl, 2-pyrimidyl, 2-furyl, 3-furyl, 2-thienyl, 2-(N-methyl)-imidazolyl, 5-triazolyl, 4-phenyl-triazol-5-yl, 5-methyl-1,2,4-oxadiazol-3-yl, $CH_3CONH$—, $CH_3SO_2NH$—, $NO_2$, $SO_2OH$, phenyl-$SO_2$—, sulfamoyl, N,N-dimethylsulfamoyl, N,N-diethylsulfamoyl, N-phenyl-N-methyl-sulfamoyl, N-cyclohexyl-sulfamoyl, —$SO_2$-heterocyclic ring, wherein the heterocyclic rings are selected from the group of piperidine, pyrrolidine, 1,2,5,6-tetrahydropyridine, tetrahydroquinoline, N-methylpiperazine, N-sulfonylmethyl-piperazine, morpholine;
$R^8$ represents methyl, hydroxymethyl, 2-methoxyphenyl, 3-methoxyphenyl, 2-pyridyl, methoxy, Another especially preferred embodiment of the invention is a compounds of formula I as above wherein X is $SO_2$ and Y is N and the broken line represents a double bond and $R^3$ represents $CH_3$ or $CF_3$ or $R^3$ together with $R^4$ and together with the atoms to which
and $R^4$, $R^6$ and $R^8$ are all hydrogen;
and $R^5$ is hydrogen or halogen;
and $R^7$ is N-methylsulfamoyl, N,N-dimethylsulfamoyl, N-cyclohexylsulfamoyl, tetrahydropyridyl-sulfonyl; $SO_2OH$, sulfamoyl;

Another especially preferred embodiment of the invention is a compounds of formula I as above wherein X is C=O and Y is N, O or CH; and
$R^2$ represents hydrogen; and
$R^3$ represents hydrogen, $CH_3$, $CF_3$, cyclohexyl, norbornene, phenyl, ethyl; and
$R^7$ represents hydrogen, N,N-dimethylsulfamoyl, N-cyclohexylsulfamoyl, tetrahydropyridyl-sulfonyl, morpholinosulfonyl sulfamoyl, bromo; and
$R^5$ represents hydrogen or bromo; and
$R^4$, $R^6$ and $R^8$ all represent hydrogen;

Another especially preferred embodiment of the invention is a compounds of formula I as above wherein X represents $CH_2$ and Y is N; and
$R^3$ represents cyclohexyl or norbornene; and
$R^5$ represents hydrogen or bromo; and
$R^7$ represents bromo or sulfamoyl; and
$R^2$, $R^4$, $R^6$ and $R^8$ all represent hydrogen;

Another especially preferred embodiment of the invention is a compounds of formula I as above wherein X represents $SO_2$ and Y represents NH; and the broken line is absent and $R^2$,
$R^4$, $R^5$ and $R^8$ all represent hydrogen;
$R^3$ represents cyclohexyl, methyl or hydrogen; and
$R^7$ represents N,N-dimethylsulfamoyl, tetrahydropyridyl-sulfonyl, bromo;
and $R^6$ represents bromo or hydrogen;

Another especially preferred embodiment of the invention is a compounds of formula I as above wherein X is $SO_2$ and N is —$NHCH_2$—; and $R^3$ represents 3-methylbut-2-yl, phenyl or cyclohexyl; and $R^7$ represents 1-piperidino-sulfonyl.

The most preferred embodiment of the invention are compounds of formula I as above wherein the compounds are the following:
2-Cyclohexyl-4-oxo-1,2,3,4-tetrahydroquinazoline;
2-Phenyl-4-oxo-1,2,3,4-tetrahydroquinazoline;
2-Methyl-3,4-dihydro-1,3-benzoxazine-4-one;
2-Phenyl-3,4-dihydro-1,3-benzoxazine-4-one;
3-Bicyclo[2.2.1]hept-5'-en-2'-yl-1,2,3,4-tetrahydro-1,2,4-benzothiadiazine-1,1-dioxide;
3-Phenyl-1,2,3,4-tetrahydro-1,2,4-benzothiadiazine-1,1-dioxide;
1,2,3,5,10,10a-Hexahydrobenzo[e]pyrrolo[1,2-b]-1,2,4-thiadiazine-5,5-dioxide;
2-Ethyl-2-methyl-3,4-dihydro-1,3-benzoxazine-4-one;
3-Cyclohexyl-6-(2-methoxyphenyl)-1,2,3,4-tetrahydro-1,2,4-benzothiadiazine-1,1-dioxide;
3-Cyclohexyl-6-(2-pyridyl)-1,2,3,4-tetrahydro-1,2,4-benzothiadiazine-1,1-dioxide;
3-Cyclohexyl-6-(3-pyridyl)-1,2,3,4-tetrahydro-1,2,4-benzothiadiazine-1,1-dioxide;
3-Cyclohexyl-7-(1-hydroxyethyl)-1,2,3,4-tetrahydro-1,2,4-benzothiadiazine-1,1-dioxide;
3-Cyclohexyl-7-acetyl-1,2,3,4-tetrahydro-1,2,4-benzothiadiazine-1,1-dioxide;
3-Cyclohexyl-7-(1-hydroxyiminoethyl)-1,2,3,4-tetrahydro-1,2,4-benzothiadiazine-1,1-dioxide;

3-Cyclohexyl-7-carbamoyl-1,2,3,4-tetrahydro-1,2,4-benzothiadiazine-1,1-dioxide;
3-Cyclohexyl-7-ethoxycarbonyl-1,2,3,4-tetrahydro-1,2,4-benzothiadiazine-1,1-dioxide;
3-Cyclohexyl-7-cyano-1,2,3,4-tetrahydro-1,2,4-benzothiadiazine-1,1-dioxide;
3-Bicyclo[2.2.1]hept-5'-en-2'-yl-7-phenyl-1,2,3,4-tetrahydro-1,2,4-benzothiadiazine-1,1-dioxide;
3-Cyclohexyl-7-(2'-acetamidophenyl)-1,2,3,4-tetrahydro-1,2,4-benzothiadiazine-1,1-dioxide;
3-Cyclohexyl-7-(2'-nitrophenyl)-1,2,3,4-tetrahydro-1,2,4-benzothiadiazine-1,1-dioxide;
3-Cyclohexyl-7-(2'-methoxyphenyl)-1,2,3,4-tetrahydro-1,2,4-benzothiadiazine-1,1-dioxide;
3-Cyclohexyl-7-(2'-methoxy-4'-trifluoromethylphenyl)-1,2,3,4-tetrahydro-1,2,4-benzothiadiazine-1,1-dioxide;
3-Cyclohexyl-7-(2',4'-dimethoxyphenyl)-1,2,3,4-tetrahydro-1,2,4-benzothiadiazine-1,1-dioxide;
3-Cyclohexyl-7-(2'-(N,N-dimethylsulfamoyl)phenyl)-1,2,3,4-tetrahydro-1,2,4-benzothiadiazine-1,1-dioxide;
3-Cyclohexyl-7-(2'-chlorophenyl)-1,2,3,4-tetrahydro-1,2,4-benzothiadiazine-1,1-dioxide;
3-Cyclohexyl-7-(2'-fluorophenyl)-1,2,3,4-tetrahydro-1,2,4-benzothiadiazine-1,1-dioxide;
3-Cyclohexyl-7-(3'-hydroxyphenyl)-1,2,3,4-tetrahydro-1,2,4-benzothiadiazine-1,1-dioxide;
3-Cyclohexyl-7-(2'-pyridyl)-1,2,3,4-tetrahydro-1,2,4-benzothiadiazine-1,1-dioxide;
3-Cyclohexyl-7-(3'-pyridyl)-1,2,3,4-tetrahydro-1,2,4-benzothiadiazine-1,1-dioxide;
3-Cyclohexyl-7-(2'-pyrimidinyl)-1,2,3,4-tetrahydro-1,2,4-benzothiadiazine-1,1-dioxide;
3-Cyclohexyl-7-(2'-furyl)-1,2,3,4-tetrahydro-1,2,4-benzothiadiazine-1,1-dioxide;
3-Cyclohexyl-7-(3'-furyl)-1,2,3,4-tetrahydro-1,2,4-benzothiadiazine-1,1-dioxide;
3-Cyclohexyl-7-(2'-thienyl)-1,2,3,4-tetrahydro-1,2,4-benzothiadiazine-1,1-dioxide;
3-Cyclohexyl-7-(1-methyl-1H-2-imidazolyl)-1,2,3,4-tetrahydro-1,2,4-benzothiadiazine-1,1-dioxide;
3-Cyclohexyl-7-(1',2',3'-triazol-4'-yl)-1,2,3,4-tetrahydro-1,2,4-benzothiadiazine-1,1-dioxide;
3-Cyclohexyl-7-(5'-phenyl-1',2',3'-triazol-4'-yl)-1,2,3,4-tetrahydro-1,2,4-benzothiadiazine-1,1-dioxide;
3-Cyclohexyl-7-(5'-methyl-1',2',4'-oxadiazol-3-yl)-1,2,3,4-tetrahydro-1,2,4-benzothiadiazine-1,1-dioxide;
3-Cyclohexyl-7-acetamido-1,2,3,4-tetrahydro-1,2,4-benzothiadiazine-1,1-dioxide;
3-Cyclohexyl-7-methylsulfonylamino-1,2,3,4-tetrahydro-1,2,4-benzothiadiazine-1,1-dioxide;
3-Cyclohexyl-7-nitro-1,2,3,4-tetrahydro-1,2,4-benzothiadiazine-1,1-dioxide;
3-Cyclohexyl-7-phenylsulfonyl-1,2,3,4-tetrahydro-1,2,4-benzothiadiazine-1,1-dioxide;
2-Cyclohexyl-1,2,3,4-tetrahydro-6-quinazoline sulfonamide;
3-Cyclohexyl-7-sulfamoyl-1,2,3,4-tetrahydro-1,2,4-benzothiadiazine-1,1-dioxide;
3-Cyclohexyl-7-sulfamoyl-1,2,3,4-tetrahydro-1,2,4-benzothiadiazine-1,1-dioxide;
3-Methyl-7-dimethylsulfamoyl-1,2,3,4-tetrahydro-1,2,4-benzothiadiazine-1,1-dioxide;
2-Cyclohexyl-1,2,3,4-tetrahydro-6-quinazoline N,N-dimethylsulfonamide;
3-Cyclohexyl-7-dimethylaminosulfonyl-1,2,3,4-tetrahydro-1,2,4-benzothiadiazine-1,1-dioxide;
3-Cyclohexyl-7-(N,N-diethylamino)sulfonyl-1,2,3,4-tetrahydro-1,2,4-benzothiadiazine-1,1-dioxide;
3-Cyclohexyl-7-pyrrolidinosulfonyl-1,2,3,4-tetrahydro-1,2,4-benzothiadiazine-1,1-dioxide;
3-Methyl-7-piperidinosulfonyl-1,2,3,4-tetrahydro-1,2,4-benzothiadiazine-1,1-dioxide;
3-Cyclopropyl-7-piperidinosulfonyl-1,2,3,4-tetrahydro-1,2,4-benzothiadiazine-1,1-dioxide;
3-Isopropyl-7-piperidinosulfonyl-1,2,3,4-tetrahydro-1,2,4-benzothiadiazine-1,1-dioxide;
3-propyl-7-piperidinosulfonyl-1,2,3,4-tetrahydro-1,2,4-benzothiadiazine-1,1-dioxide;
3-Benzyl-7-piperidinosulfonyl-1,2,3,4-tetrahydro-1,2,4-benzothiadiazine-1,1-dioxide;
3-Cyclopentyl-7-piperidinosulfonyl-1,2,3,4-tetrahydro-1,2,4-benzothiadiazine-1,1-dioxide;
3-Cyclohexyl-7-piperidinosulfonyl-1,2,3,4-tetrahydro-1,2,4-benzothiadiazine-1,1-dioxide;
3-Bicyclo[2.2.1]hept-5'-en-2'-yl-7-piperidinosulfonyl-1,2,3,4-tetrahydro-1,2,4-benzothiadiazine-1,1-dioxide;
3-Cyclohexyl-7-(1',2',3',6'-tetrahydropiperidino)sulfonyl-1,2,3,4-tetrahydro-1,2,4-benzothiadiazine-1,1-dioxide;
3-Cyclohexyl-7-(N-methyl-N-phenylamino)sulfonyl-1,2,3,4-tetrahydro-1,2,4-benzothiadiazine-1,1-dioxide;
3-Cyclohexyl-7-(1'-(1',2',3',4'-tetrahydroquinolinyl))sulfonyl-1,2,3,4-tetrahydro-1,2,4-benzothiadiazine-1,1-dioxide;
3-Cyclohexyl-7-(4'-methylpiperazino)sulfonyl-1,2,3,4-tetrahydro-1,2,4-benzothiadiazine-1,1-dioxide;
3-Cyclohexyl-7-(4'-methylsulfonylpiperazino)sulfonyl-1,2,3,4-tetrahydro-1,2,4-benzothiadiazine-1,1-dioxide;
3-Cyclohexyl-7-morpholinosulfonyl-1,2,3,4-tetrahydro-1,2,4-benzothiadiazine-1,1-dioxide;
3-Bicyclo[2.2.1]hept-5'-en-2'-yl-7-bromo-1,2,3,4-tetrahydro-1,2,4-benzothiadiazine-1,1-dioxide;
2-Methyl-4-oxo-3,4-dihydro-6-quinazoline-N,N-dimethylsulfonamide;
2-Trifluoromethyl-4-oxo-3,4-dihydro-6-quinazoline sulfonamide;
2-Trifluoromethyl-4-oxo-3,4-dihydro-6-quinazoline N,N-dimethylsulfonamide;
2-Trifluoromethyl-4-oxo-3,4-dihydro-6-quinazoline-1',2',3',6'-tetrahydropiperidinosulfonamide;
2-Trifluoromethyl-4-oxo-3,4-dihydro-6-quinazoline N-cyclohexylsulfonamide;
2-Trifluoromethyl-4-oxo-3,4-dihydro-6-quinazoline morpholinosulfonamide;
2-Cyclohexyl-4-oxo-3,4-dihydro-6-quinazoline-N,N-dimethylsulfonamide;
3-Methyl-7-sulfamoyl-1,2-dihydro-1,2,4-benzothiadiazine-1,1-dioxide;
3-Methyl-7-dimethylsulfamoyl-1,2-dihydro-1,2,4-benzothiadiazine-1,1-dioxide;
3-Methyl-7-(1',2',3',6'-tetrahydropiperidino)sulfonyl-1,2-dihydro-1,2,4-benzothiadiazine-1,1-dioxide;
3-Methyl-7-cyclohexylsulfamoyl-1,2-dihydro-1,2,4-benzothiadiazine-1,1-dioxide;
3-Trifluoromethyl-7-dimethylsulfamoyl-1,2-dihydro-1,2,4-benzothiadiazine-1,1-dioxide;
2-Trifluoromethyl-4-oxo-3,4-dihydro-6-quinazolinesulfonic acid;
3-Cyclohexyl-8-methyl-1,2,3,4-tetrahydro-1,2,4-benzothiadiazine-1,1-dioxide;
3-Cyclohexyl-8-hydroxymethyl-1,2,3,4-tetrahydro-1,2,4-benzothiadiazine-1,1-dioxide;
3-Cyclohexyl-8-(2-methoxyphenyl)-1,2,3,4-tetrahydro-1,2,4-benzothiadiazine-1,1-dioxide;

3-Cyclohexyl-8-(3-methoxyphenyl)-1,2,3,4-tetrahydro-1,2,4-benzothiadiazine-1,1-dioxide;
3-Cyclohexyl-8-(2-pyridyl)-1,2,3,4-tetrahydro-1,2,4-benzothiadiazine-1,1-dioxide;
3-Cyclohexyl-8-methoxy-1,2,3,4-tetrahydro-1,2,4-benzothiadiazine-1,1-dioxide;
5,7-Dibromo-1,2-dihydro-1,2,4-benzothiadiazine-1,1-dioxide;
3-Cyclohexyl-2-methyl-7-morpholinosulfonyl-1,2,3,4-tetrahydro-1,2,4-benzothiadiazine-1,1-dioxide;
3-Cyclohexyl-4-methyl-7-morpholinosulfonyl-1,2,3,4-tetrahydro-1,2,4-benzothiadiazine-1,1-dioxide;
7-Methylsulfonylamino-1,2,3,3a,4,5-hexahydrobenzo[e]pyrrolo[2,1-c]-1,2,4-thiadiazine-5,5-dioxide;
7-Sulfamoyl-1,2,3,3a,4,5-hexahydrobenzo[e]pyrrolo[2,1-c]-1,2,4-thiadiazine-5,5-dioxide;
7-Methylsulfamoyl-1,2,3,3a,4,5-hexahydrobenzo[e]pyrrolo[2,1-c]-1,2,4-thiadiazine-5,5-dioxide;
7-Cyclohexylsulfamoyl-1,2,3,3a,4,5-hexahydrobenzo[e]pyrrolo[2,1-c]-1,2,4-thiadiazine-5,5-dioxide;
7-Dimethylsulfamoyl-1,2,3,3a,4,5-hexahydrobenzo[e]pyrrolo[2,1-c]-1,2,4-thiadiazine-5,5-dioxide;
7-Methylsulfamoyl-1,2,3,5-tetrahydrobenzo[e]pyrrolo[2,1-c]-1,2,4-thiadiazine-5,5-dioxide;
7-Dimethylsulfamoyl-1,2,3,5-tetrahydrobenzo[e]pyrrolo[2,1-c]-1,2,4-thiadiazine-5,5-dioxide;
7-Cyclohexylsulfamoyl-1,2,3,5-tetrahydrobenzo[e]pyrrolo[2,1-c]-1,2,4-thiadiazine-5,5-dioxide;
7-(1',2',3',6'-Tetrahydropiperidino)sulfonyl-1,2,3,5-tetrahydrobenzo[e]pyrrolo[2,1-c]-1,2,4-thiadiazine-5,5-dioxide;
3-Bicyclo[2.2.1]hept-5'-en-2'-yl-5,7-dimethyl-1,2,3,4-tetrahydro-1,2,4-benzothiadiazine-1,1-dioxide;
3-Cyclohexyl-7-(N,N-diethylsulphamoyl)-5-methyl-1,2,3,4-tetrahydro-1,2,4-benzothiadiazine-1,1-dioxide;
3-Bicyclo[2.2.1]hept-5'-en-2'-yl-5,7-diphenyl-1,2,3,4-tetrahydro-1,2,4-benzothiadiazine-1,1-dioxide;
3-Bicyclo[2.2.1]hept-5'-en-2'-yl-5,7-disulfamoyl-1,2,3,4-tetrahydro-1,2,4-benzothiadiazine-1,1-dioxide;
3-Bicyclo[2.2.1]hept-5'-en-2'-yl-5,7-dichloro-1,2,3,4-tetrahydro-1,2,4-benzothiadiazine-1,1-dioxide;
5-Bromo-3-cyclohexyl-7-sulfamoyl-1,2,3,4-tetrahydro-1,2,4-benzothiadiazine-1,1-dioxide;
2-Bicyclo[2.2.1]hept-5'-en-2'-yl-6,8-dibromo-1,2,3,4-tetrahydroquinazoline;
2-Bicyclo[2.2.1]hept-5'-en-2'-yl-6,8-dibromo-4-oxo-1,2,3,4-tetrahydroquinazoline;
3-Bicyclo[2.2.1]hept-5'-en-2'-yl-5,7-dibromo-1,2,3,4-tetrahydro-1,2,4-benzothiadiazine-1,1-dioxide;
5,7-Dibromo-3-bicyclo[2.2.1]heptan-2'-yl-1,2,3,4-tetrahydro-1,2,4-benzothiadiazine-1,1-dioxide;
3-Cyclohexyl-5,7-dibromo-1,2,3,4-tetrahydro-1,2,4-benzothiadiazine-1,1-dioxide;
3-Adamantyl-5,7-dibromo-1,2,3,4-tetrahydro-1,2,4-benzothiadiazine-1,1-dioxide;
3-Phenyl-5,7-dibromo-1,2,3,4-tetrahydro-1,2,4-benzothiadiazine-1,1-dioxide;
3-Ethoxy-5,7-dibromo-1,2,3,4-tetrahydro-1,2,4-benzothiadiazine-1,1-dioxide;
3-Methyl-5,7-dibromo-1,2-dihydro-1,2,4-benzothiadiazine-1,1-dioxide;
3-Cyclohexyl-6-methyl-7-(2'-pyridyl)-1,2,3,4-tetrahydro-1,2,4-benzothiadiazine-1,1-dioxide;
3-Cyclohexyl-6-methyl-7-(4'-triazolyl)-1,2,3,4-tetrahydro-1,2,4-benzothiadiazine-1,1-dioxide;
3-Cyclohexyl-6-methyl-7-sulfamoyl-1,2,3,4-tetrahydro-1,2,4-benzothiadiazine-1,1-dioxide;
3-Cyclopentyl-6-methyl-7-piperidinosulfonyl-1,2,3,4-tetrahydro-1,2,4-benzothia-diazine-1,1-dioxide;
3-Cyclohexyl-6-methyl-7-morpholinosulfonyl-1,2,3,4-tetrahydro-1,2,4-benzothiadiazine-1,1-dioxide;
3-Cyclohexyl-6-(2-methoxyphenyl)-7-methyl-1,2,3,4-tetrahydro-1,2,4-benzothiadiazine-1,1-dioxide;
3-Cyclohexyl-6-methoxy-7-piperidinosulfonyl-1,2,3,4-tetrahydro-1,2,4-benzothia-diazine-1,1-dioxide;
3-Cyclohexyl-7,8-ethylenedioxy-1,2,3,4-tetrahydro-1,2,4-benzothiadiazine-1,1-dioxide;
3-cyclohexyl-6,7-ethylenedioxy-1,2,3,4-tetrahydro-1,2,4-benzothiadiazine-1,1-dioxide;
3-Cyclohexyl-6-chloro-7-sulfamoyl-1,2,3,4-tetrahydro-1,2,4-benzothiadiazine-1,1-dioxide;
3-Phenyl-6-chloro-7-sulfamoyl-1,2,3,4-tetrahydro-1,2,4-benzothiadiazine-1,1-dioxide;
3-Cyclohexyl-6-bromo-7-piperidinosulfonyl-1,2,3,4-tetrahydro-1,2,4-benzothia-diazine-1,1-dioxide;
2-cyclohexylmethylamino-5-N,N-dimethylsulfamoylbenzenesulfonamide;
2-Ethylamino-7-(1',2',3',6'-tetrahydropiperidino)sulfonylbenzene sulfonamide;
3-Isobutyl-8-(piperidinosulfonyl)-2,3,4,5-tetrahydro-1,2,5-benzothiadiazepine-1,1-dioxide;
3-Cyclohexyl-7-cyclopentylsulfinyl-1,2,3,4-tetrahydro-1,2,4-benzothiadiazine-1,1-dioxide;
3-Cyclohexyl-7-cyclopentylsulfinyl-1,2,3,4-tetrahydro-1,2,4-benzothiadiazine-1,1-dioxide;
3-Cyclohexyl-7-cyclopentylsulfinyl-1,2,3,4-tetrahydro-1,2,4-benzothiadiazine-1,1-dioxide; or
3-Cyclohexyl-7-cyclopentylsulfinyl-1,2,3,4-tetrahydro-1,2,4-benzothiadiazine-1,1-dioxide or a pharmaceutical acceptable salt thereof.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulfonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Definitions of Substituents

Halogen is fluorine, chlorine, bromine, or iodine.

Alkyl means a straight chain or branched chain of from one to six carbon atoms or cyclic alkyl of from three to seven carbon atoms, including but not limited to, methyl, ethyl, propyl, isopropyl, butyl, isobutyl, t-butyl, pentyl, hexyl; methyl, ethyl, propyl and isopropyl are preferred groups.

Haloalkyl means alkyl as above substituted one or more times with halogen as defined above. Preferred embodiments are $CF_3$, $C_2F_5$, $CH_2Cl$, $CHCl_2$, —$CHFCH_2F$, —$CHClCH_2Cl$;

Cycloalkyl means cyclic alkyl of from three to seven carbon atoms such as cyclopropyl, cyclobutyl, cyclopentyl, cyclohexyl, cycloheptyl.

Cycloalkylalkyl means cyclic alkyl as above and alkyl as above wherein the alkyl can be regarded as a substituent on the cycloalkyl and vice versa. Preferred groups are $C_{3-6}$-cycloalkyl and $C_{1-4}$-alkyl such as —($CH_2$)-cyclopropyl, -cyclopropyl-($C_{1-4}$-alkyl), —($CH_2$)$_n$-cyclohexyl, -cyclohexyl-($C_{1-4}$-alkyl), ($C_{1-4}$-alkyl)-cyclobutyl, -cyclobutyl($C_{1-4}$-alkyl)-($C_{1-4}$-alkyl)cyclopentyl, -cyclopentyl($C_{1-4}$-alkyl), —($C_{1-4}$-alkyl)cyclohexyl, cyclohexyl($C_{1-4}$-alkyl);

Halocycloalkyl means cyclic alkyl as above which is substituted with one or more halogen as above, including but not limited to chlorocyclopropyl, fluorocyclopropyl, iodocyclopropyl, dichlorocyclopropyl, difluorocyclopropyl, chlorocyclobutyl, fluorocyclobutyl, chlorocyclopentyl, fluorocyclopentyl, iodocyclopenyl, chlorocyclohexyl, fluorocyclohexyl, dichlorocyclohexyl, difluorocyclohexyl, iodocyclohexyl. Preferred embodiments are mono- and di-substituted cycloalkyl of 3 to 6 carbons, such as dichlorocyclopropyl, difluorocyclopropyl, chlorocyclohexyl, fluorocyclohexyl, iodocyclohexyl, chlorocyclopentyl, fluorocyclopentyl.

Alkenyl means a straight chain or branched chain of from two to six carbon atoms containing one double bond, including but not limited to ethenyl, 1-propenyl, 2-propenyl, 1-butenyl, 2-butenyl, and 3-butenyl.

Alkynyl means a straight chain or branched chain of from two to six carbon atoms containing one triple bond, including but not limited to ethynyl, 1-propynyl, 2-propynyl, 1-butynyl, 2-butynyl, and 3-butynyl.

Alkoxy is O-alkyl, wherein alkyl is as defined above.

Alkoxyalkyl is -alkyl-O-alkyl, wherein alkyl is as defined above.

Hydroxyalkyl is alkyl as defined above substituted with OH;

Amino is $NH_2$ or NH-alkyl or N-(alkyl)$_2$, wherein alkyl is as defined above.

Alkylamino is alkyl as defined above which is substituted with amino as defined above. Preferred embodiments are —$CH_2$—N(alkyl)$_2$, —CH—N(alkyl)$_2CH_3$, —$CH_2CH_2$N(alkyl)$_2$, —$CH_2$—$NH_2$, —CH—($NH_2$)—$CH_3$, —$CH_2CH_2$$NH_2$;

Cyano is CN;

Cyanoalkyl is alkyl as defined above substituted with CN;

Nitro is —$NO_2$;

Nitroalkyl is alkyl as defined above subsituted with nitro as defined above;

Thio is SH or S-alkyl, wherein alkyl is as defined above;

Alkylthio is alkyl as above substituted with a thio group which is as defined above.

Acyl is (C=O)—$R^o$ or (C=S)—$R^o$ wherein $R^o$ is alkyl; phenyl which may be substituted one or more times with substituents selected from the group consisting of halogen, $CF_3$, $NO_2$, amino, alkyl, alkoxy, phenyl and $SO_2NR'R''$ wherein R' and R'' each independently are hydrogen or alkyl or wherein R' and R'' together is $(CH_2)_m$ wherein m is 2, 3, 4, 5 or 6; or $R^o$ is benzyl; or $NR^{III}R^{IV}$ wherein $R^{III}$ and $R^{IV}$ each independently are hydrogen or alkyl or wherein $R^{III}$ and $R^{IV}$ together is $(CH_2)_p$ wherein p is 2, 3, 4, 5 or 6.

Acylamino is acyl-NH— wherein acyl is as defined above.

Aryl is aromatic carbocycles such as phenyl or biphenyl and fused carbocycles such as naphtyl;

HET is an 5- to 6-membered cyclic heteroaryl and includes for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, and 4-pyrazolyl, furanyl, tetrahydrofuranyl, pyrrolyl, pyrrolidyl, imidazolyl, oxadiazolyl, pyridyl, thienyl, isooxazolyl, pyrimidyl, pyrazole, triazolyl. Especially preferred heteroaryl of the invention are pyridyl, pyrimidyl, triazole, furyl, thienyl, oxadiazolyl, imidazolyl;

A carbocyclic 7- to 12-membered ring structure includes mono- bi- and tricyclic structures. Preferred embodiments are 7- to 10 membered ring structures such as

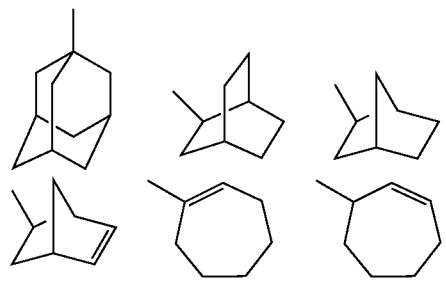

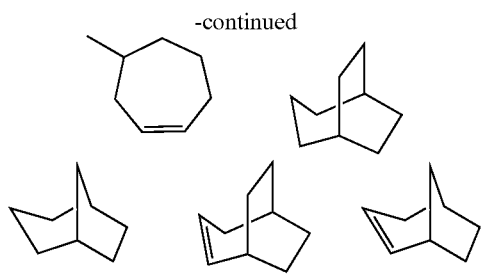

a heterocyclic 3- to 8 membered ring structure includes a partly or completely saturated heterocyclic ringstructure such as aziridine, pyrrolidine, piperidine, piperazine, homopiperidine, homopiperazine, azacyclooctane, 1,3-diazacyclooctane, 1,4-diazacyclooctane, tetrahydrofuran, tetrahydrothiophene, morpholine, tetrahydropyridine, and compounds such as

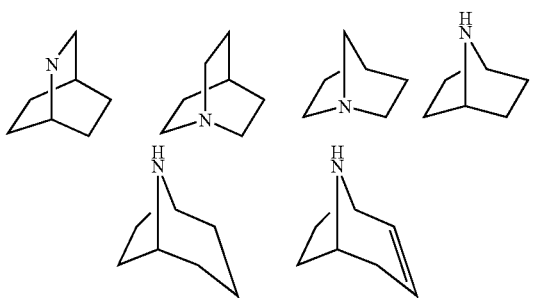

The preferred embodiments are 5- to 6-membered rings containing at least one nitrogen such as pyrrolidine, piperidine, piperazine, morpholine, tetrahydropyridine.

The described 4- to 7-membered rings fused to the ring structure of formula I, formed between the substituents $R^2$ and $R^3$ or $R^3$ and $R^4$ or $R^5$ and $R^6$ or $R^6$ and $R^7$ or $R^7$ and $R^8$ are carbocyclic rings optionally containing a heteroatom and optionally containing a carbonyl group. Preferred rings are 5- and 6-membered carbocyclic rings;

The rings formed between the substituents $R^7$ and $R^6$ or $R^8$ are 5- or 6-membered and containing O, C=O, S=O, or $SO_2$-groups and optionally containg nitrogen.

Preferred rings are —O—$(CH_2)$n-O—; wherein n is 1, 2 or 3; —$SO_2$—NR—$(CH_2)$n- wherein n is 1 or 2; —SO—NR—$(CH_2)$n- wherein n is 1 or 2; —$SO_2$—$(CH_2)$n- wherein n is 2 or 3; —SO—$(CH_2)$n- wherein n is 2 or 3; —CO—CH=CH—NH—; —CO—CH=CH—O—; —CO—$(CH_2)_n$—NH— wherein n is 1 or 2; —CO—NH—$(CH_2)_n$ wherein n is 1 or 2; —CO—$(CH_2)_2$—O—;

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

A compound of the invention includes endo- and exo-forms and tautomers where possible.

Pharmaceutical Compositions

An aspect of the invention provides novel pharmaceutical compositions comprising a therapeutically effective amount of the chemical compound of the invention and the use of compounds of the invention for the manufacture of a medicament for the treatment of specific diseases or disorders;

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, and intravenous injection) administration, or those in a form suitable for administration by inhalation or insufflation.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

The dose administered must of course be carefully adjusted to the age, weight and condition of the individual being treated, as well as the route of administration, dosage form and regimen, and the result desired.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Method of Treating

The compounds of the present invention are AMPA receptor stimulators and therefore useful for the treatment of a range of disorders or diseases responsive to AMPA receptor modulators. As en embodiment of the invention the disease are responsive to positive modulation of the AMPA receptor. The compounds may be used in the treatment, prevention, profylaxis or alleviation of a disease, disorder or condition of the central nervous system as for example: neurodegenerative disorders, cognitive or memory dysfunction, memory and learning disorders, attention disorder, learning and memory disorders resulting from ageing, trauma, stroke, epilepsy; Alzheimer's disease, depression, schizophrenia, memory loss, AIDS-dementia, senile dementia, learning deficit, cognition deficit, sexual dysfunctions, psychotic disorder, sexual dysfunction, intellectual impairment disorders, schizophrenia, depression or autism, attention deficit, or a disorder or disease resulting from neurotoxic agents, alcohol intoxication, substance abuse, cardiac bypass surgery or cerebral ischemia; Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

I.p. means intraperetoneally, which is a well known route of administration.

P.o. means peroral, which is a well known route of administration.

The invention then comprises the following alone or in combination:

The use of a compound as above wherein the disease to be treated is responsive to the AMPA receptor modulation.

The use of a compound as above for the manufacture of a medicament for the treatment of disease which are responsive to the AMPA receptor modulation.

The use as above wherein the disease is memory and learning disorders, psychotic disorder, sexual dysfunction, intellectual impairment disorders, schizophrenia, depression or autism; Alzheimer's disease, learning deficit, attention deficit, memory loss or senile dementia; or a disorder or disease resulting from trauma, stroke, epilepsy, Alzheimer's disease, neurotoxic agents, aging, neurodegenerative disorder, alcohol intoxication, substance abuse, cardiac bypass surgery or cerebral ischemia;

Biology

In Vitro Inhibition of $^3$H-AMPA Binding

L-glutamate (GLU) is the major excitatory neurotransmitter in the mammalian central nervous system. From electrophysiological- and binding studies, there appear to be at least three subtypes of GLU receptors, tentatively named N-methyl-D-aspartate (NMDA)-, quisqualate- and kainate receptors. GLU receptor subtypes sensitive to quisqualate and kainate as a group are often referred to as non-NMDA receptors. Receptor binding studies using the labelled agonists $^3$H-AMPA (α-amino-3-hydroxy-5-methyl-4-isoxazolepropionic acid) (for quisqualate receptors) and $^3$H-kainate (for kainate receptors) have shown different antagonist selectivities and regional distribution. AMPA has been known for several years to be a potent and selective agonist at the traditionally named quisqualate receptors. Activation of quisqualate receptors by AMPA is associated with $Na^+$ influx and $K^+$ efflux leading to depolarization.

The non-NMDA receptors have recently been reclassified to include the quisqualate activated metabotropic receptor type, linked to the inositol triphosphate and diacylglycerate metabolism. AMPA does not interact with the metabotropic quisqualate receptor but only the ionotropic quisqualate receptor. Selective activation of the metabotropic type has been claimed for trans-ACPD. Recently, the potent and competitive non-NMDA receptor antagonists CNQX and NBQX have been described, and CNQX have been reported not to block the effect of quisqualate at the metabotropic receptor subtype. $^3$H-AMPA is a selective radioligand for labelling the ionotropic quisqualate (AMPA) receptors.

Tissue Preparation

Preparations are performed at 0–4° C. unless otherwise indicated. Cerebral cortex from male Wistar rats (150–200 g) is homogenized for 5–10 sec in 20 ml Tris-HCl (30 mM, pH 7.4) using an Ultra-Turrax homogenizer. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous glutamate and then centrifuged for 10 min at 27,000×g. The pellet is then homogenized in buffer and centrifuged at for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g for 10 min. The pellet is washed twice with 20 ml 30 mM Tris-HCl containing 2.5 mM CaCl$_2$, pH 7.4 using an Ultra-Turrax homogenizer and centrifuged for 10 min at 27,000×g. The final pellet is resuspended in 30 mM Tris-HCl containing 2.5 mM CaCl$_2$ and 100 mM KSCN, pH 7.4 (100 ml per g of original tissue) and used for binding assays. Aliquots of 0.5 (0.2) ml are added to 25 (20) µl of test solution and 25(20) µl of $^3$H-AMPA (5 nM, final concentration), mixed and incubated for 30 min at 2° C. Non-specific binding is determined using L-glutamate (0.6 mM, final concentration). After incubation the 550 µl samples are added 5 ml of ice-cold buffer and poured directly onto Whatman GF/C glass fibre filters under suction and immediately washed with 5 ml of ice-cold buffer. The 240 µl samples are filtered over glass fibre filter using a Skatron cell harvrester. The filters are washed with 3 ml ice-cold buffer. The amount of radioactivity on the filters is determined by conventional liquid scintillation counting. Specific binding is total binding minus non-specific binding.

Results

The test value will be given as the IC$_{50}$ (the concentration (µM) of the test substance which inhibits the specific binding of $^3$H-AMPA by 50%)

Test Results

The compound numbers refer to the table below.

| Compound | IC$_{50}$ (µM) |
| --- | --- |
| 13 | 22.0 |
| 14 | 45.0 |
| 15 | 39.0 |
| 44 | 3.5 |
| 47 | 5.3 |
| 48 | 4.4 |
| 49 | 17.0 |
| 57 | 26.0 |
| 58 | 3.4 |
| 61 | 8.5 |
| 62 | 6.0 |
| 63 | 6.0 |
| 113 | 13.0 |
| 114 | 33.0 |
| 115 | 7.0 |

Potentiation of AMPA Induced [$^3$H]GABA Release from Cultured Cortical Neurons

Neurons which express receptors for excitatory amino acids can be depolarized by such compounds and this depolariztion will ultimately lead to a release of transmitter substance from the neurons. Cultured neurons obtained from 16-day-old mouse embryo cortex are mainly GABAergic and express all types of excitatory amino acid receptors. This means that they can be stimulated by high potassium (55 mM) or by the excitatory amino acids NMDA (20 µM), AMPA (5 µM) and kainate (5 µM) to release their neurotransmitter GABA.

$^3$H-GABA may be used to label the GABA transmitter pool in the neurons and the release of $^3$H-GABA from the neurons may be used as a simple functional model for studies of the effects of excitatory amino acid receptor agonists, antagonists, and modulators.

Methods

Cell Cultures

Cerebral cortices of 15–16 day-old NMRI mouse embryos are chopped in 0.4×0.4 mm cubes and the tissue is dissociated by mild trypsinization (0.1% (wt/vol) trypsin, 37° C., 10 min). Subsequently the cell suspension (3 mill/ml) is inoculated into poly-L-lysine-coated 30 mm Petri dishes (3 ml/dish) containing a slightly modified DMEM (24.5 mM KCl) supplemented with p-aminobenzoate (7 µM), insulin (100 mU/L) and 10% (vol/vol) horse serum. Cells are maintained in culture for 5–7 days with the addition of the antimitotic agent cytosine arbinoside (5 µM) from day 2 in vitro to prevent glial proliferation. For further details and references, see Drejer et al. (Exp. Brain Res. 47, 259 (1982)).

Release Experiments

Release experiments are performed using the model described by Drejer et al. (Life Sci. 38, 2077 (1986)). Cerebral cortex neurons cultured in Petri dishes (30 mm) are added 100 mM γ-vinyl-GABA one hour before the experiment in order to inhibit degradation of GABA in the neurons. 30 min before the experiment 5 µCi $^3$H-GABA is added to each culture. After this preloading period the cell monolayer at the bottom of the dish is covered with a piece of nylon mesh to protect the cells against mechanical damage and to facilitate dispersion of medium over the cell layer. The preloading medium is removed and the Petri dishes are placed in a superfusion system consisting of a peristaltic pump continuously delivering thermo-stated 37° C. superfusion medium (HEPES buffered saline (HBS): 10 mM HEPES, 135 mM NaCl, 5 mM KCl, 0.6 mM MgSO$_4$, 1.0 mM CaCl$_2$ and 6 mM D-glucose; pH 7.4) from a reservoir to the top of the slightly tilted Petri dish. The medium is continuously collected from the lower part of the dish and delivered to a fraction collector. Initially, the cells are superfused with HBS for 30 min (flow rate 2 ml/min). Then cells are stimulated for 30 sec every 4 min by changing the superfusion medium from HBS to a corresponding medium containing 5 µM AMPA in the absence or presence of modulators.

Test substances are dissolved in 50% DMSO, 48% ethanol. The final DMSO and ethanol concentration in the assay must not exceed 0.1%

Results

The induced release of $^3$H-GABA (cpm) is corrected for the mean basal release (cpm) before and after the stimulation and used for calculation of the test value.

The potentiation of the AMPA response by a test substance is expressed relative to the potentiation of the AMPA response induced by cyclothiazide (30 µM).

Results

The result of the test is shown in FIGS. 1 and 2. The results show significantly increased FIG. 1 shows potentiation of AMPA induced [$^3$H]GABA release from cultured cortical neurons by compound 115. The potentiation is expressed relative to the potentiation induced by 30 µM cyclothiazide.

FIG. 2 shows potentiation of AMPA induced [$^3$H]GABA release from cultured cortical neurons by compound 114. The potentiation is expressed relative to the potentiation induced by 30 µM cyclothiazide.

Voltage Clamp

Methods

Experiments were performed in voltage clamp using conventional whole cell patch clamp methods (Hamill et al., 1981), essentially as described previously (Mathiesen et al., 1998). The following salt solutions were used (mM): NaCl (140), KCl (4), $CaCl_2$ (2), $MgCl_2$ (1), Sucrose (30), Tetrodotoxin (0.0003), Bicuculline Methiodide (0.005) and HEPES (10, pH 7.4). Intracellular solution (mM): CsCl (120), CsF (20), $MgCl_2$ (2), EGTA (10), HEPES (10, pH=7.2).

Cell Cultures

Mouse neocortical neurons were cultured essentially as described by Drejer et al. (1987). Briefly, the forebrains from embryonic (E17) NMRI mice were removed under sterile conditions. The tissue was chopped in 0.4 mm cubes and the triturated with trypsin (12.5 μg/ml) and DNAse (2.5 μg/ml), 15 min, 37° C. The cells were suspended at a concentration of $1 \times 10^6$ cells/ml in a slightly modified DMEM which contained horse serum (10% (v/v)), penicillin (333 U/ml), paraaminobenzoic acid (1 mg/ml), L-glutamine (0.5 mM), insulin (0.08 U/ml) and KCl (23.8 mM). The cell suspension was subsequently inoculated into poly-L-lysine coated 35 mm Petri dishes (2 ml/dish). Glass coverslips (3.5 mm) were placed in the dishes before coating. After 24 hr in culture, the medium was replaced by freshly made medium containing 1% N2 supplement instead of serum.

The cells were kept in culture for 7–14 days at 37° C. (5% $CO_2$/95% $O_2$) before experiments were carried out.

Electronics, programs and data acquisition: The amplifier used was the EPC-9 (HEKA-electronics, Lambrect, Germany) run by a Power Macintosh G3 computer via an ITC-16 interface. Experimental conditions were set with the Pulse-software accompanying the amplifier. Data were low pass filtered and sampled directly to hard-disk at a rate of 3 times the cut-off frequency.

Pipettes and electrodes: Pipettes were pulled from borosilicate glass (Modulohm, Copenhagen, Denmark) using a horizontal electrode puller (Zeitz-Instrumente, Augsburg, Germany). The pipette resistances were 1.7–2.4 MW in the salt solutions used in these experiments. The pipette electrode was a chloridized silver wire, and the reference was a silverchloride pellet electrode (In Vivo Metric, Healdsburg, USA) fixed to the experimental chamber. The electrodes were zeroed with the open pipette in the bath just prior to sealing.

Experimental procedure: Coverslips were transferred to a 15 ml experimental chamber mounted on the stage of an inverted microscope (IMT-2, Olympus) supplied with Nomarski optics. The neurons were continuously superfused with extracellular saline at a rate of 2.5 ml/min. After giga-seal formation (1–5 GW, success-rate≈90%) the whole cell configuration was attained by suction.

The cells were held at a holding voltage of −60 mV and at the start of each experiment the current was continuously measured for at least 30 sec to ensure a stable leak current. AMPA-containing solutions were delivered to the chamber through a custom-made gravity-driven flowpipe, the tip of which was placed approximately 50 μm from the cell. Application was triggered when the tubing connected to the flow pipe was compressed by a valve controlled by the Pulse-software. AMPA (30 μM) was applied for 1 sec every 45 sec. After obtainment of responses of a repeatable amplitude the compound to be tested was included in both the chamber and in the AMPA-containing solution. The compound was present until responses of a new repeatable was obtained.

The sample interval in all experiments was 310 μsec.

All experiments were performed at room temperature (20–25° C.).

Materials

Pregnant (9 days) NMRI mice were obtained from Bomholtgaard Breeding and Research Center, Ry, Denmark.

Horse serum, N2 supplement and culture media were purchased from Life Technologies (GIBCO), Roskilde, Denmark.

AMPA (a-amino-3-hydroxy-5-methyl-4-isoxazolepropionic acid) was synthesized at NeuroSearch A/S. Tetrodotoxin was purchased from Alomone Labs, Jerusalem, Israel and Bicuculline Methiodide from RBI, MA, USA. Sucrose was from Fluka Chemie, Buchs, Switzerland. All other reagents were from SIGMA, USA.

Results

The results are shown in FIGS. 3–7.

The compounds 56 (FIG. 3), 63 (FIG. 4), 111 (FIG. 6), 114 (FIG. 7) and 115 (FIG. 5) all potentiated the current induced by application of 30 μM AMPA. An example for each compound is shown below. It is seen that the potentiation in every case is reversible, even though the effect of 56 and 63 persits for several minutes after wash out of the compounds. The time between AMPA stimulations was 45 sec. Scalebars: 63: 200 pA/2 sec; 56: 500 pA/5 sec; 115: 50 pA/2 sec; 111: 400 pA/3 sec; 114: 40 pA/3 sec. In the experiments shown the concentration of the compounds was 3 μM (56, 63 and 114) or 10 μM (111 and 115) The effect of the compounds were concentration-dependent, as exemplified for 114 below (scale bars 200 pA/5 sec).(FIG. 8)

REFERENCES

Drejer J., Honoré T. and Schousboe A. (1987) Excitatory amino acid-induced release of $^3$H-GABA from cultured mouse cerebral cortex interneurons. *J. Neurosci.* 7: 2910–2916.

Hamill O. P., Marty A., Neher E., Sakmann B. and Sigworth F. J. (1981) Improved patch-clamp techniques for high-resolution current recording from cells and cell-free membrane patches. *Pflügers Arch.* 39: 85–100.

Mathiesen C., Varming T. and Jensen L. H. (1998) In vivo and in vitro evaluation of AMPA receptor antagonists in rat hippocampal neurones and cultured mouse cortical neurones. *Eur. J. Pharmacol.* 353: 159–167.

Iontophoretic Application

Purpose

Evaluation of the in vivo effects of positive AMPA modulators (PAMs) on the AMPA evoked spike activity in rat hippocampus.

Principle

Hippocampal single neuron spike activity is strongly influenced by excitatory input, and iontophoretic application of AMPA induces spike activity in vivo in a dose-dependent manner (Mathiesen et al. 1998). The AMPA evoked spike activity is inhibited by intravenous (i.v.) administration of a wide range of AMPA receptor antagonists (Mathiesen et al. 1998), which indicated that the excitation is primarily mediated via AMPA receptors. PAMs potentate AMPA receptor activation in vitro, and if this mechanism also operates in vivo, the i.v. injection of an PAM should enhance AMPA evoked spike activity. Thus, the aim of this study was to test the in vivo effect of a group of in vitro active PAMs. This have been done by studying their ability to enhances AMPA evoked spike activity after i.v. administration.

PREPARATION

Experiments were performed on male Wistar rats (M & B, Denmark) weighing 280–380 g, housed in two per cage with free access to food and water. The rats were anaesthetised with mebumal (50 mg kg$^{-1}$ ip.) and the femoral artery was catheterised for the purpose of monitoring blood pressure and the vein for intravenous injection of drugs and continuous injection of 0.9% NaCl (0.5–1.0 ml h$^{-1}$) and mebumal (5–10 mg h$^{-1}$). Additional anaesthetic was given i.v. if the rat responded to a pinch of the back foot. The trachea was cannulated and the rats were placed in a stereotaxic frame and ventilated by a rodent ventilator (Ugo Basile, Comerio-Varese, Italy). Core body temperature was maintained at 37.5° C. by a DC heating pad. The left and dorsal part of the parietal bone was removed by craniotomy and the dura was withdrawn exposing the pia mater and underlying brain, covered with 0.9% NaCl.

Compounds/Reagents

AMPA (Sigma, USA) was dissolved at 10 mM in 0.2 M NaCl. NMDA (Sigma, USA) was dissolved at 100 mM in 100 mM NaCl. Both solutions were adjusted to pH 7.5–8.0 with NaOH. COMPOUND 61 was dissolved in 200 mM CH$_3$SO$_3^-$ Na$^+$ at a contration of 10 mM for iontophoretic application (pH 5.7) and in isotonic glucose (278 mM) for i.v. administration. Cyclothiazide, COMPOUND 63, COMPOUND 56, COMPOUND 115 and COMPOUND 114 were all dissolved at in 5% chremophore solution at a concentration of 5 mg ml$^{-1}$.

Parameters

Evoked neuronal spike activity was analyzed on-line by a computer, saving single spikes and time of event. Neuronal spike activity (number of action potentials s$^{-1}$) was monitored on a pulse rate histogram together with indicators for AMPA, COMPOUND 61 and vehicle application.

Procedure

Extracellular recordings of single hippocampal neuron spikes were made with five-barrel glass microelectrodes (5B120F-6, World Precision Instruments Inc., Sarasota, Fla., USA) with a tip diameter of 10–12 µm. The individual barrels were filled with 5 M NaCl (recording), 400 mM NaCl (current balancing), 10 mM COMPOUND 61 in 200 mM CH$_3$SO$_3^-$ Na$^+$ (pH 4.7), 200 mM CH$_3$SO$_3^-$ Na$^+$ (pH 4.7, Vehicle), and the last barrel was filled with the AMPA.

Experiments were performed on hippocampal neurons (A=5.5–6.5 mm, L=1.5–2.0 mm, H=2.0–3.0 mm, according to Paxinos & Watson, 1986). Neuronal spike activity was evoked by iontophoretic application of AMPA for periods of 10 to 15 s with 1.5 min intervals. Single neuron spike activity was amplified 5000 times with a bandwidth of 0.3 and 3 kHz (CyberAmp 320 with a A1 402 x50 smartprobe, Axon Instruments, California, USA). On-line and off-line analyses were performed by the Spike2 program with a 1401 plus interface (Cambridge Electronic Design Limited, England). The computer program also recorded mean arterial blood pressure and monitored and controlled iontophoretic application.

AMPA was ejected into hippocampus in regular cycles of 100–105 s. When neuronal responses were stable (when the AMPA responses did not vary more than 10%, measured over a 10 s time period) for at least ½ hour, then a single dose of either cyclothiazide, COMPOUND 63, COMPOUND 56, COMPOUND 115, COMPOUND 61 or COMPOUND 114 (10 mg kg$^{-1}$) was injected into the femoral vein. Recording of neuronal spike activity was continued for at least 45 min after intravenous injection. The PAM reactivity was tested by microiontophoretic application of COMPOUND 61 (20 nA, FIG.).

Results

FIG. 8 shows that iontophoretic application of COMPOUND 61 enhanced AMPA evoked spike activity, whereas the vehicle did not influence the evoked spike activity. Intravenous administration cyclothiazide (10 mg kg$^{-1}$) did not enhance AMPA evoked spike activity (FIG. 10).

FIG. 9. Iontophoretic application of COMPOUND 61 enhanced AMPA evoked single neuron spike activity. The iontophoretic application of the vehicle did not influence AMPA evoked spike activity.

FIG. 10. Cyclothiazide (10 m kg$^{-1}$ i.v.) did not affect AMPA evoked spike activity in hippocampus. Shaded box above the AMPA1 trace indicate time of administration (1500 s after onset of registrating).

The in vivo effects of the PAMs on AMPA evoked spike activity was dependent on the control spike activity level. COMPOUND 63 enhanced small AMPA responses, evoked by low intensity AMPA stimulation, but had only marginal effect on large AMPA responses, evoked by high intensity AMPA stimulation (FIG. 11). There was an initial inhibition of the AMPA responses and the onset of the enhancement occur 15 to 30 min after i.v. administration (FIG. 11). FIG. shows an example of enhancement of AMPA responses by COMPOUND 56 (10 mg kg$^{-1}$). The onset occurred approximately 10 min after administration (FIG. 12).

FIG. 11. COMPOUND 63 (10 mg kg–1 i.v.) enhanced the low intensity AMPA responses (12 nA), but had only marginal effect on high intensity AMPA responses (17 nA). 10 mg kg–1 COMPOUND 63 was given 1500 s after onset of recording. The time of injection is marked by a shaded box above the AMPA2 trace.

FIG. 12. COMPOUND 56 (10 mg kg$^{-1}$ i.v.) enhanced AMPA evoked spike activity. The compound was injected 1250 s after onset of registration. The time of injection is marked with a shaded box above the AMPA trace.

FIG. 13 shows an example of enhancement of AMPA spike activity after i.v. administration of COMPOUND 115 (10 mg kg$^{-1}$). The effect started 2 min after i.v. administration and lasted for more than 2 hours. COMPOUND 61 (10 mg kg$^{-1}$) also enhanced AMPA responses in hippocampus. The 3-fold increase in AMPA evoked spike activity induced by COMPOUND 61 started 20 minutes after administration and lasted for more than 2 hours (FIG. 14). COMPOUND 114 (10 mg kg$^{-1}$) induced a 10-fold increase of the AMPA responses, when control level of the AMPA responses were low (from 21 to 209 spikes response$^{-1}$, mean response,FIG. 15), while only smaller enhancement observed with larger control responses (from 124 to 204 spikes response$^{-1}$, FIG. 16).

FIG. 13. COMPOUND 115 (10 mg kg$^{-1}$ i.v.) enhances AMPA evoked spike activity in hippocampus. The shaded box indicate the time in i.v. injection, 1900 s after onset of registration. The effect of COMPOUND 115 lasted for more than 2 hours.

FIG. 14. COMPOUND 61 enhanced AMPA responses in hippocampus. 10 mg kg$^{-1}$ i.v. was given 1000 s after onset of registration (marked by a shaded box above the trace). The effect of COMPOUND 61 lasted for more than 2.5 hour.

FIG. 15. COMPOUND 114 (10 mg kg$^{-1}$ i.v.) enhanced AMPA evoked spike activity. The compound was given 1730 s after onset of registration, which is marked by a shaded box above the AMPA trace.

FIG. 16. COMPOUND 114 (10 mg kg$^{-1}$ i.v.) approximately doubled the AMPA responses. The i.v. administration occurred at time 3900 s and is indicated by shaded box above the AMPA trace The results show that Cyclothiazide did not show any in vivo effects after i.v. administration. However, COMPOUND 63, COMPOUND 56, COMPOUND 115, COMPOUND 61 and COMPOUND 114 enhanced AMPA evoked spike activity in an activity-dependent manner.

REFERENCES

MATHIESEN, C., VARMING, T. & JENSEN, L. H. (1998). In vivo and in vitro evaluation of AMPA receptor antagonists in rat hippocampal neurones and cultured mouse cortical neurones. *European Journal of Pharmacology* 353,159–167.

PAXINOS, G. & WATSON, C. (1986). *The rat brain in stereotaxic coordinates*. Second Edition.

Passive Avoidance

PURPOSE: To test the pharmacological effect of compounds on associative memory.

PRINCIPLE: A Mouse is placed in a light compartment with access to a dark compartment. If it enter the dark compartment it will receive a foot-shock (0.4 mA). After a delay (24 hours) the association to risk an unpleasant foot-shock by re-entering the dark compartment is tested.

ANIMALS: Female NMRI mice (Bomholdtgaard, DK) weighing 22–25 g were used. The mice were kept in Macrolon plastic cages with free access to food (Altromin, DK) and tap water. The mice were habituated to the laboratory for at least 3 days before testing (light on 7:00am/light off 7:00 pm).

EQUIPMENT: The passive avoidance apparatus consisted of a modular test chambers (ENV-307, MED-Associates, US). The light and the dark compartment consisted of plexiglas boxes of equal size (15×17×13 cm; width×length× height) with metal grid floors. A sliding guillotine door was located at the aperture (4×4 cm) connecting the two compartments. A manual grid scrambler (ENV-412, MED-Associates, US) was used to provide the 0.4 mA foot-shock.

PARAMETERS: Entry latency (sec) to re-enter the dark compartment was measured.

PROCEDURE: The mice are pre-treated (usually 30 min) before training with the test compound.

Training: One mouse is placed in the light compartment and the guillotine door to the dark compartment is opened. When the mouse has entered the dark compartment with all 4 paws it will receive one foot-shock (0.4 mA) and it will be taken to its home cage. Test: After a delay (24 hours) the mouse will re-enter the light compartment and time latency to enter the dark compartment is measured with a time limit at 2 minutes. Time latency is noted as 2 minutes if the mouse has not entered the dark compartment within maximal test time (2 minutes).

Vehicle: 10% Tween 80.
Dosis vol.: 10 ml/kg
n=10;

RESULTS: Mean (±SEM) entry latency for each group is presented.

The result in FIG. 17 shows the memory enhancing effect of different concentrations of the compound 61;

BRIEF DESCRIPTION OF THE DRAWINGS

FIG. 8 shows the concentration-dependent effect of a compound of the invention (114).

FIG. 9. Iontophoretic application of COMPOUND 61 and the iontophoretic application of the vehicle;

FIG. 10. Cyclothiazide is applied in hippocampus.

FIG. 11. COMPOUND 63 is applied;

FIG. 12. COMPOUND 56 is applied.

FIG. 13 COMPOUND 115 is applied.;

FIG. 13. COMPOUND 115 in hippocampus.

FIG. 14. COMPOUND 61 in hippocampus;

FIG. 15. COMPOUND 114;

FIG. 16. COMPOUND 114;

EXAMPLES

General Transformation Methods

Figure 1:
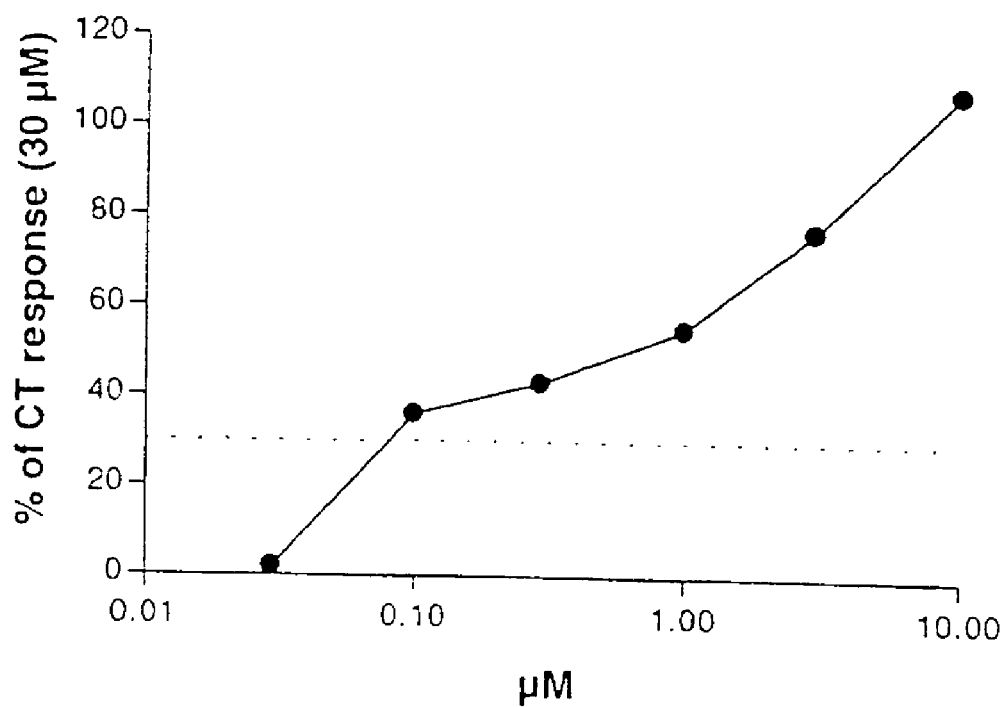
FIG. 1 and FIG. 2 shows the potentiation of AMPA induced [$^3$H]GABA release from cultured cortical neurons by compounds of the invention.
Figure 2:
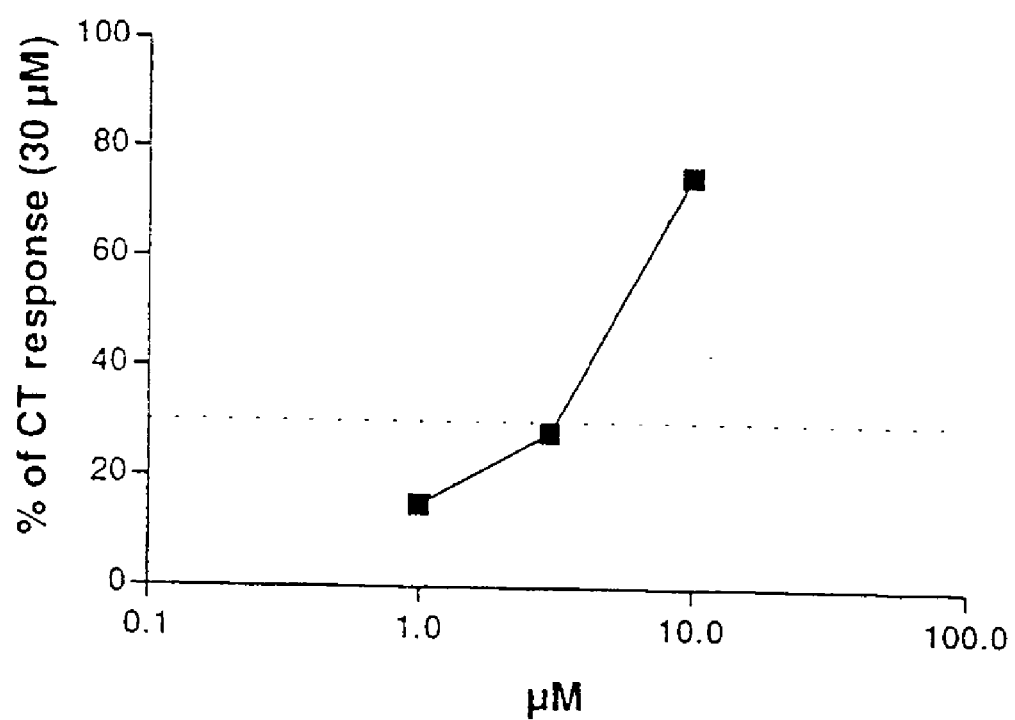
Figure 3:
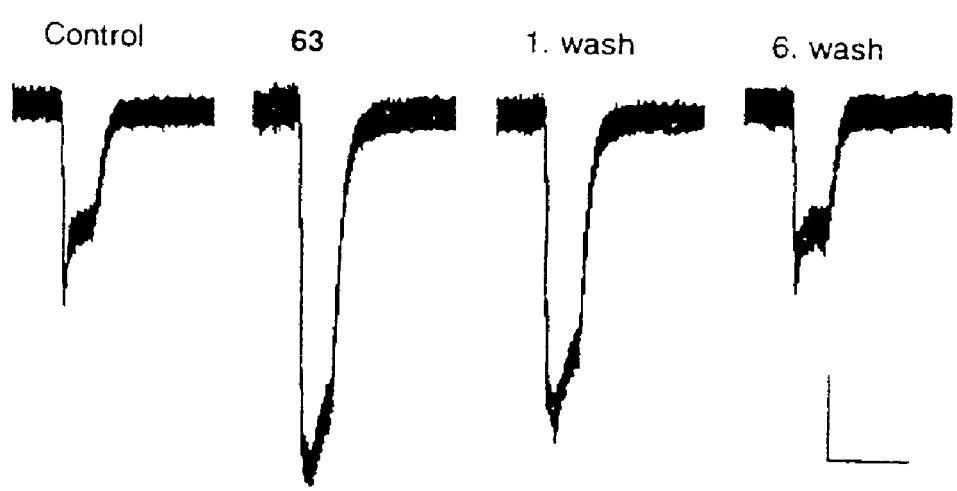
FIGS. 3–8 shows the voltage clamp experiments on compounds of the invention. The compounds 56 (FIG. 3), 63 (FIG. 4), 111 (FIG. 6), 114 (FIG. 7) and 115 (FIG. 5) all potentiated the current induced by application of 30 μM AMPA.
Figure 4:
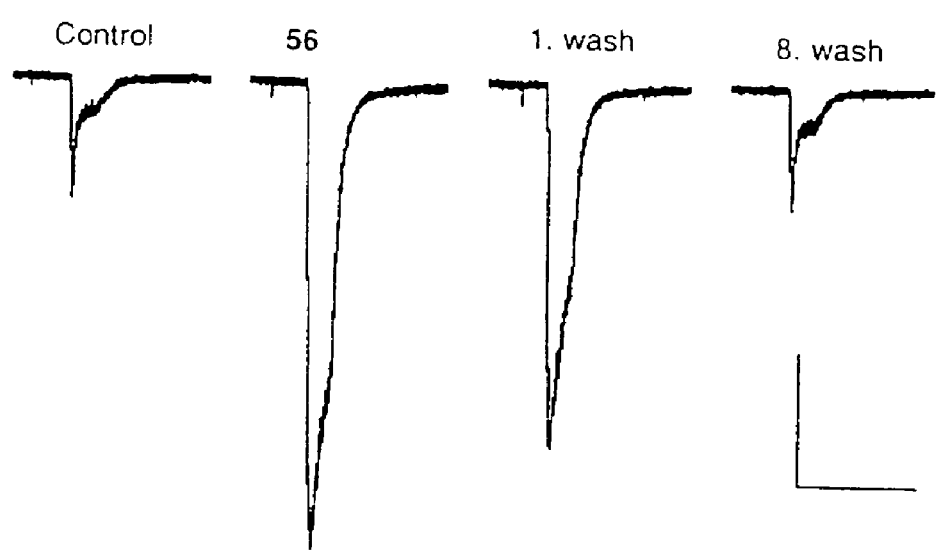
Figure 5:
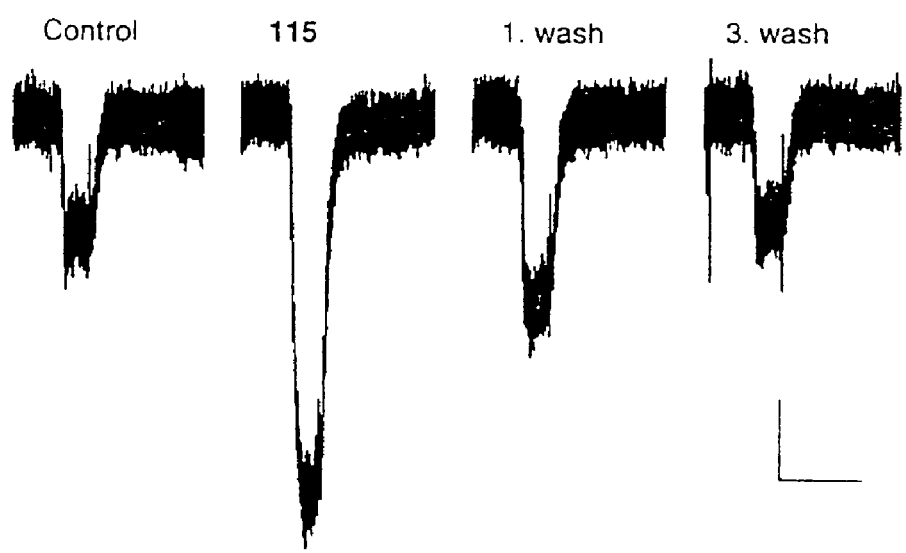
Figure 6:
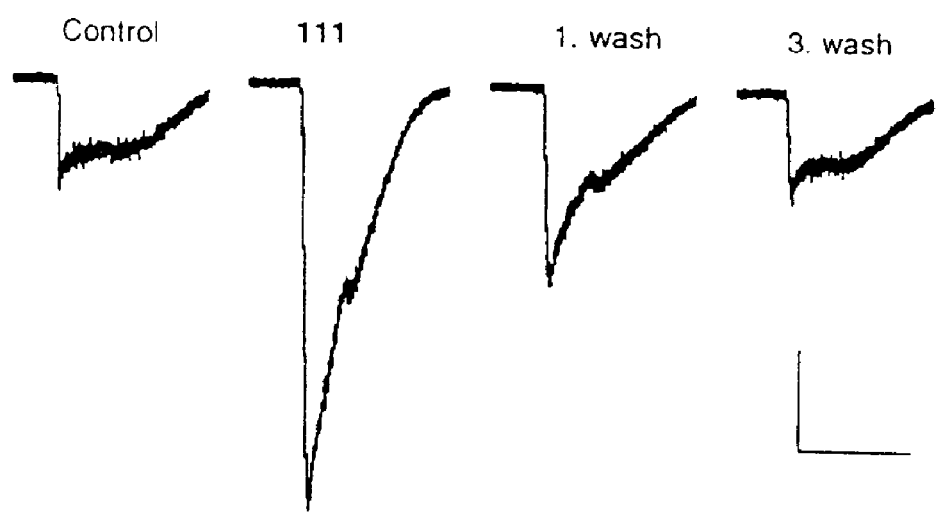
Figure 7:
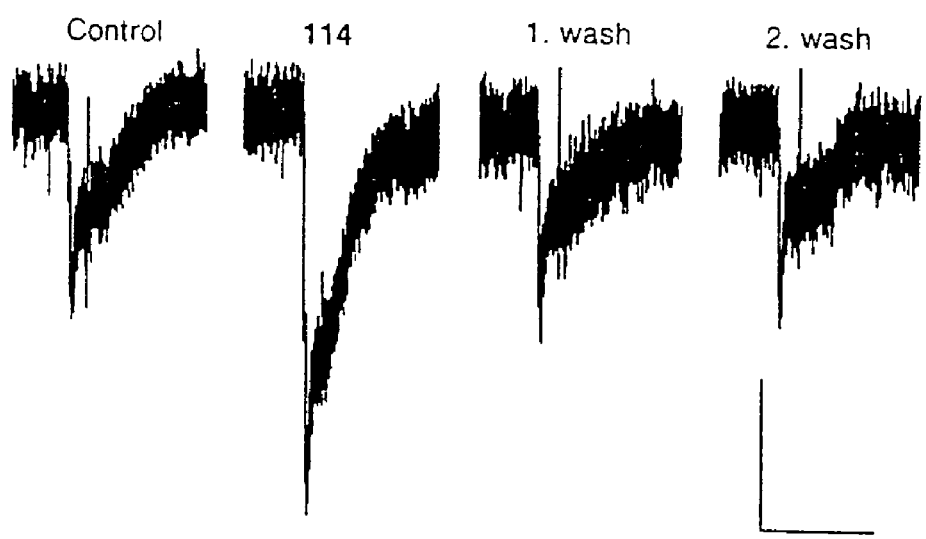
Figure 8:
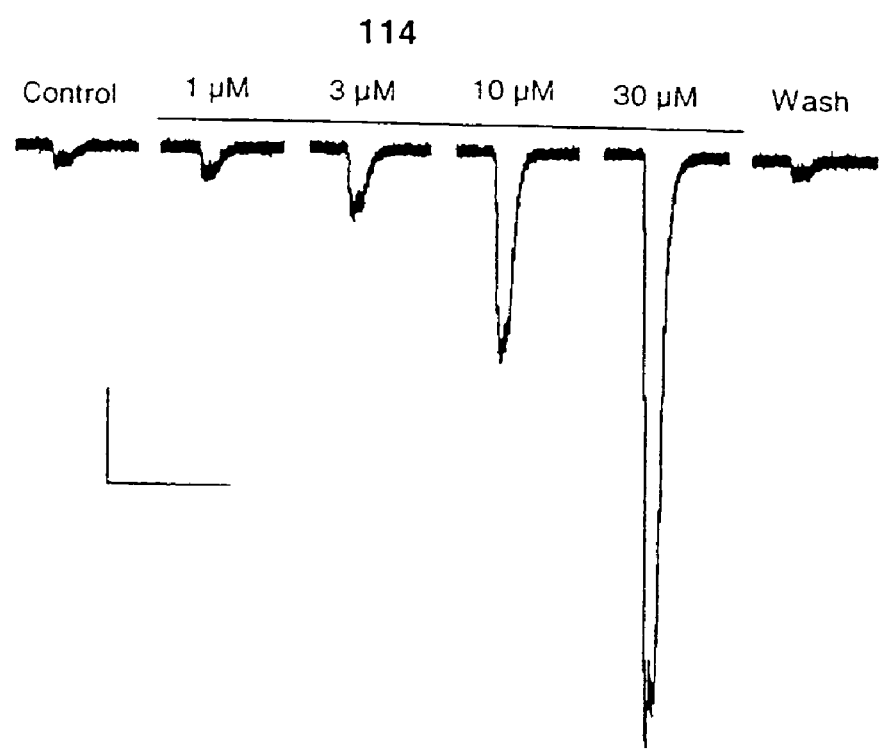
Figure 9:
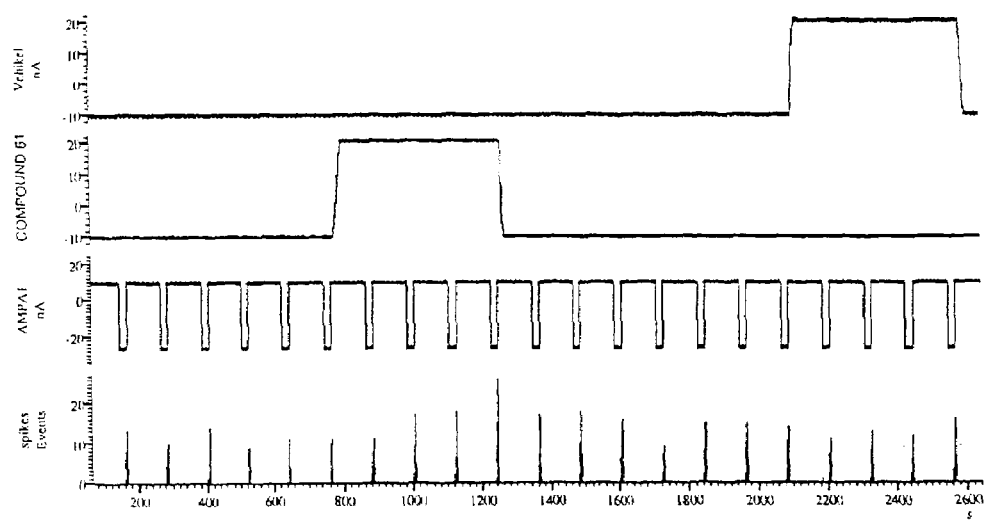
FIG. 9–FIG. 16 are experiments of iontophoresis.
Figure 10:
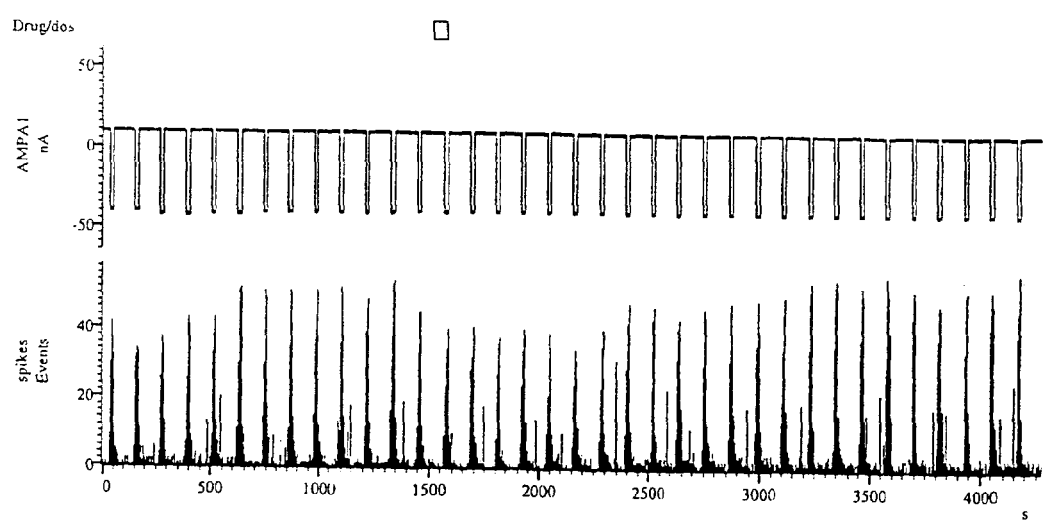
Figure 11:
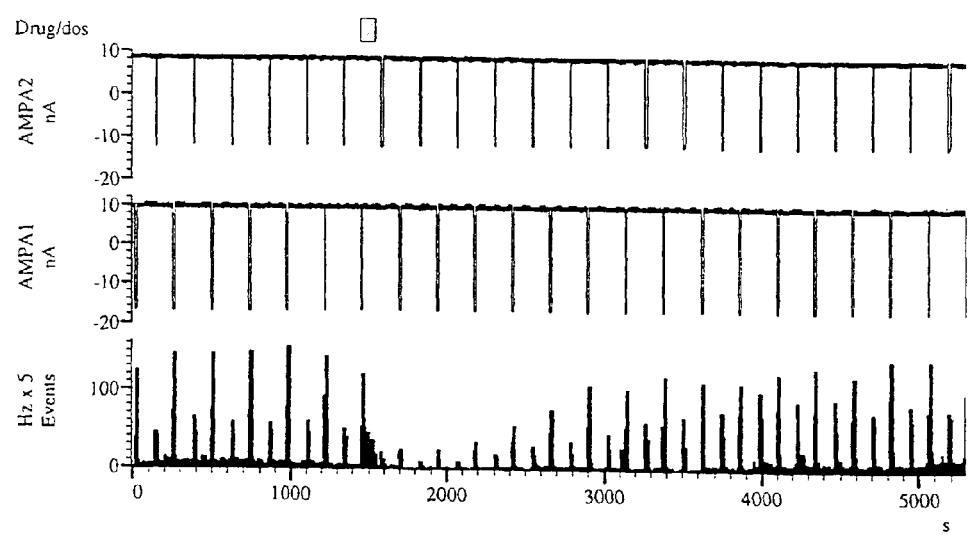
Figure 12:
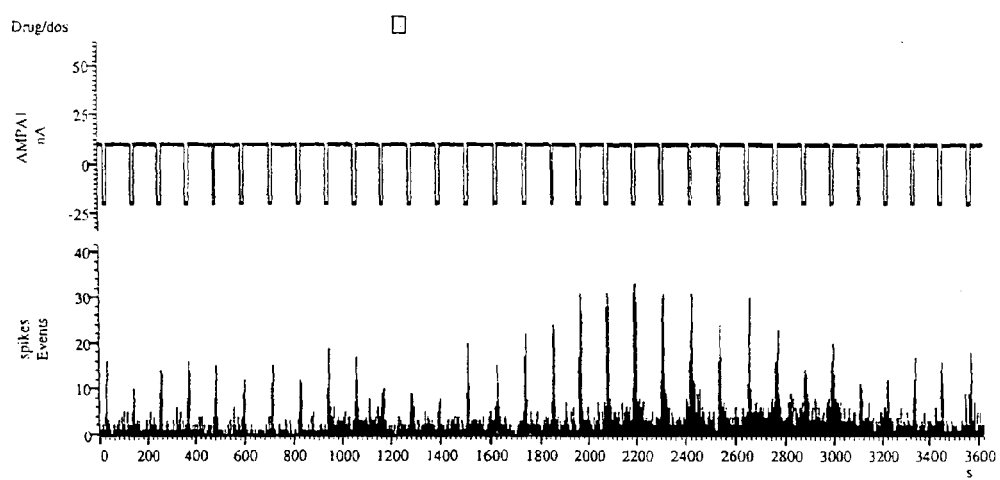
Figure 13:
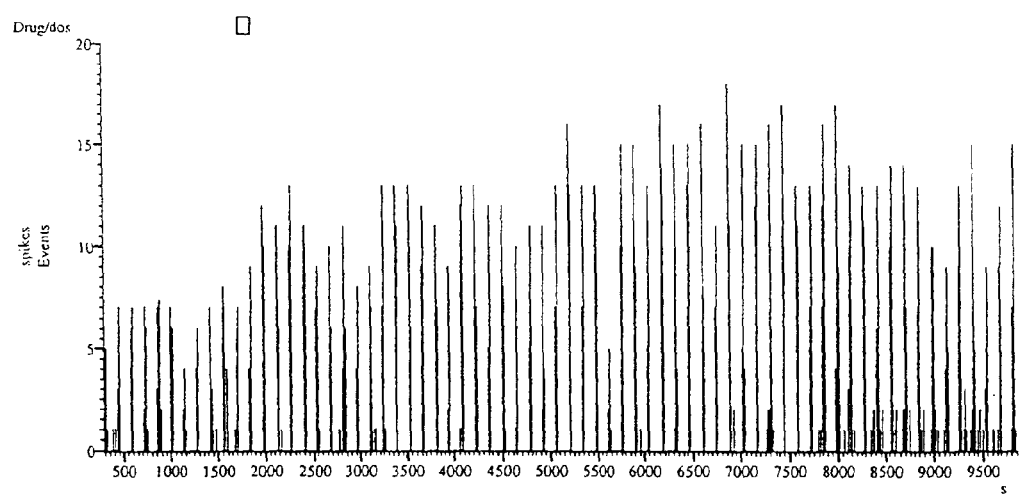
Figure 14:
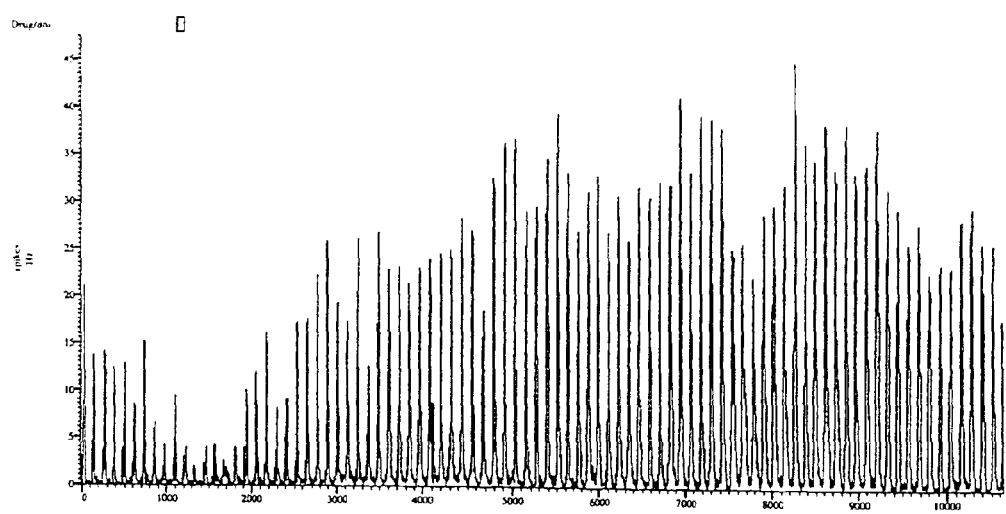
Figure 15:
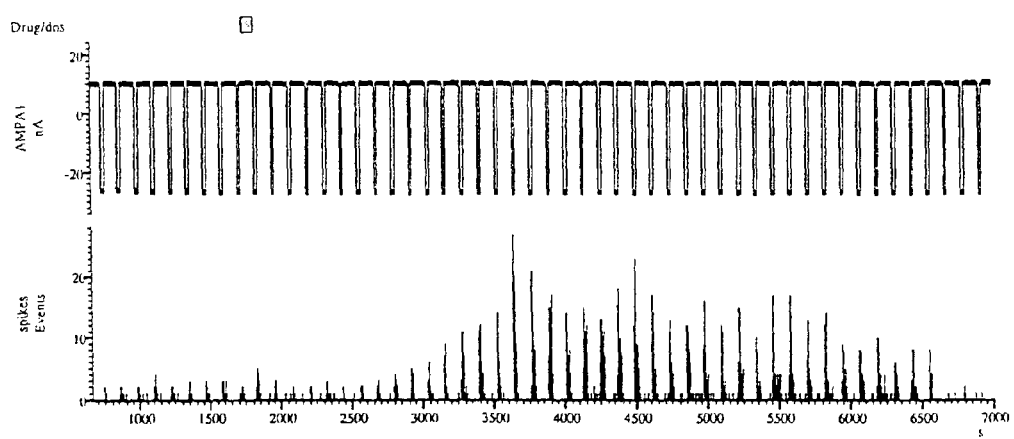
Figure 16:
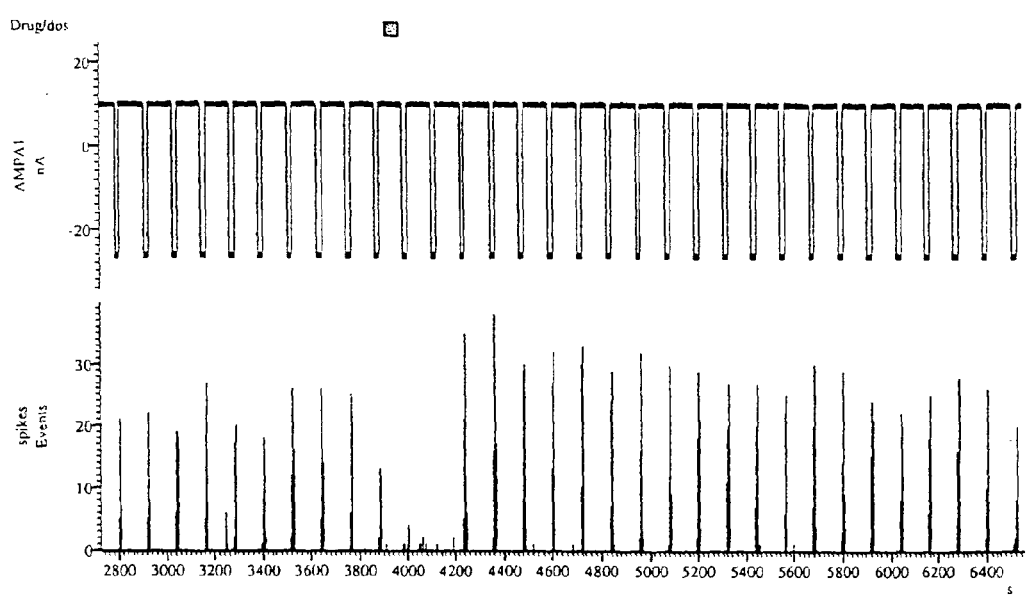
Figure 17:
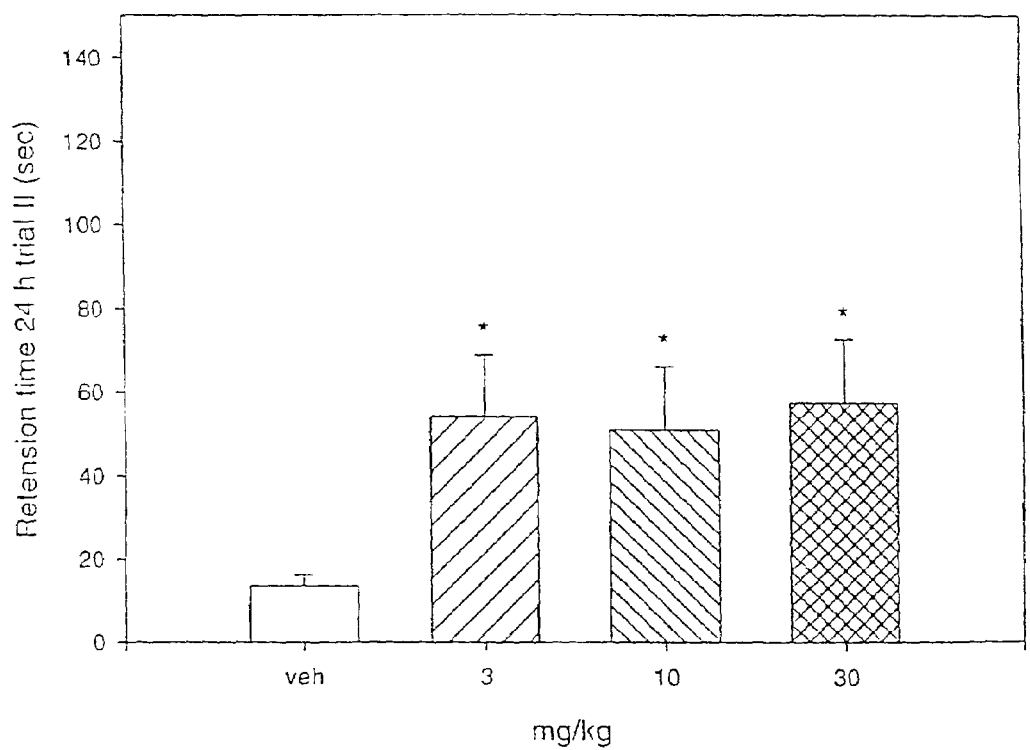
FIG. 17. Passive avoidence test of compound 61.

Method A.

Sulfamoylation in General.

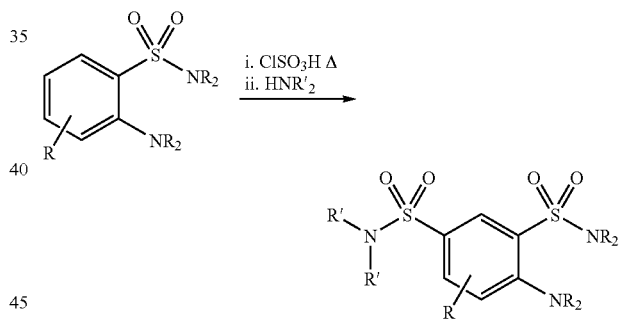

The compound (32.5 mmol) to be chlorosulfonated was dissolved in chlorosulfonic acid (75 ml) and heated in an oil bath at 110° C., until TLC indicated that the reaction had gone to completion*. The reaction mixture was poured onto ice and the precipitate formed, was isolated by filtration. The isolated solid was washed with a small amount of water and dried on the filter. The solid was dissolved in dry THF (200 ml) and added an excess of the amine (230 mmol) and the reaction mixture was left over night with stirring at rt. The reaction mixture was evaporated to dryness, then stirred with water to afford a solid which was isolated by filtration and washed with EtOAc on the filter. Further purification was possible either by column chromatography or recrystallization from EtOAc/hexane. Yields were typically: 60–90%.

[a small aliquot was taken out, added to ice in a test tube, neutralized with Na$_2$CO$_3$ and then extracted with EtOAc. The aqueous phase was removed and the organic phase was added piperidine (xs) and left for some time. TLC was taken from this small scale reaction mixture].

Method B.

o-Sulfamoylation of Anilines.†

† see also Girard Y., Atkinson J. G. and Rokach J., *J. Chem. Soc., Perkin I*, (1979) 1043.

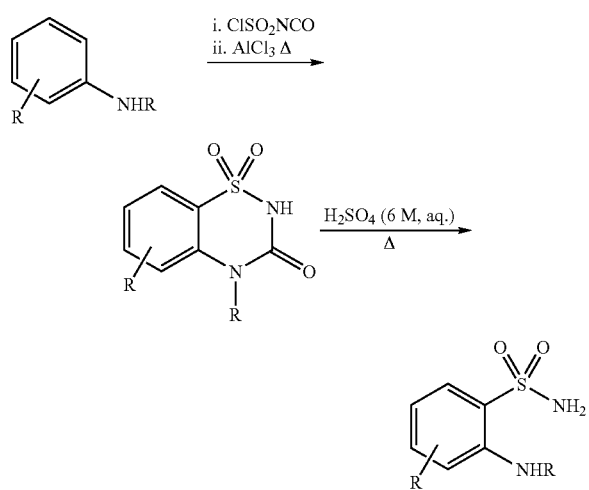

To a stirred solution of the aminobenzene derivative (250 mmol) in nitroethane or nitromethane (100 ml) at −50° C., was added a solution of ClSO₂NCO (275 mmol) in nitroethane or nitromethane (75 ml) so that the reaction temperature did not exceed −30° C. The cooling bath was removed and the thick reaction mixture allowed to heat up to 0° C. Solid AlCl₃ (300 mmol) was added in one portion. The clear brown reaction mixture was heated in an oil bath at 120° C. for 20 min, then cooled to rt. and poured into a beaker with stirred ice water (1 l). The precipitate formed, was isolated by filtration.* The urea intermediate (98 mmol) was suspended in a mixture of dioxane (250 ml) and 6 M H₂SO₄ (or only conc. HCl) (500 ml) and heated to reflux over night. The reaction mixture was cooled to rt., filtered and dioxane was removed from the filtrate by evaporation. The aqueous remanense was neutralized to pH=7–8 using 4 M NaOH. The precipitate formed, was isolated by filtration and washed with water and EtOAc.* Overall yields ranged from 10% to 75%.

*[Meta substituted anilines gives rice to a mixture of the two possible isomers which at the stage of the urea intermediate may be separated by crystallization from MeOH or at the stage of end product by crystallization from EtOAc/hexane or chromatography.]

Method C.

Trifluoroacetyl Protection.

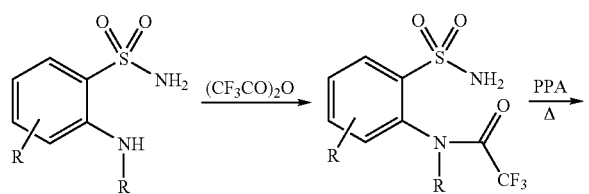

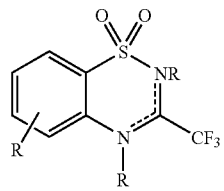

To a stirred solution of the 2-aminobenzenesulfonamide derivative (27 mmol) in dry THF (75 ml) at 0° C. was added trifluoroacetic anhydride such that the reaction mixture did not exceed +10° C. The reaction mixture was stirred at rt. until all starting material was consumed. The reaction mixture was evaporated to dryness, stirred with water, filtered and washed with hexane. The isolated solid was added PPA (250 g) and heated in an oil bath at 140° C. for 2½ h. The reaction mixture was cooled to 60–70° C. and poured onto a mechanically stirred ice water solution. The precipitated formed was isolated by filtration and air dried. Overall yields were typically 85–90%.

Method D.

Trifluoroacetyl Deprotection.

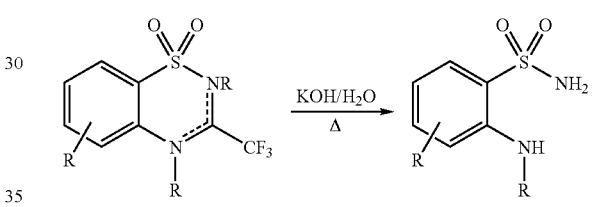

A stirred solution of the trifluoroacetyl protected compound (3.6 mmol) dissolved in 1 M KOH (30 ml) was heated to 80° C. for 1 h. The reaction mixture was cooled to rt. and pH adjusted to 7 using conc. HCl (aq.). The reaction mixture was cooled to 0° C. and filtered. The isolated solid was washed with water and air dried. Yields typically ranged from 85–95%.

Method E.

Formation of dihydrobenzothiadiazines-1,1-dioxide from 2-aminobenzene-sulfonamides.

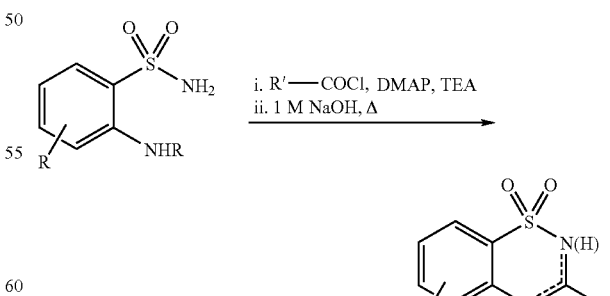

To a stirred solution of the 2-aminobenzenesulfonamide derivative (148 mmol), triethylamine (150 mmol), 4-(N,N-dimethylamino)pyridine (7.5 mmol) in 600 ml THF at 5° C. was added the carboxylic acid chloride. The reaction mixture was left with stirring over night and then evaporated to dryness. The crude material was stirred with water and filtered. The isolated solid was dissolved in 1 M NaOH (250 ml) and heated to 80° C. for 3 h. The reaction mixture was cooled to rt. and pH adjusted to 7 using conc. HCl. The precipitate formed was isolated and recrystallized from i-PrOH. Overall yields ranged from 80–90%.

Method F.

Reduction of dihydrobenzothiadiazines-1,1-dioxide to tetrahydrobenzo-thiadiazines-1,1-dioxide.

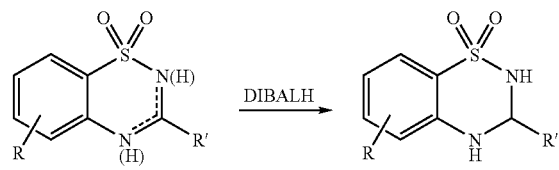

To a stirred solution of the dihydrobenzothiadiazine-1,1-dioxide (19.4 mmol) in dry THF (200 ml) at −70° C. was added a solution of DIBALH 1.5 M in toluene (33 ml; 50 mmol). The reaction mixture was left with stirring over night while the temperature slowly increases from −70° C. to −15° C.*. Water (10 ml) was added to the reaction mixture followed by 1 M NaOH (5 ml). The reaction mixture was then warmed to rt. and extracted with EtOAc. The combined organic fractions were dried with MgSO$_4$ and evaporated to dryness. In some cases the product was further purified by column chromatography. Yields ranged from 45–85%.

[The product aminal is further reduced to the ring opened alkylamine if the temperature is not controlled carefully].

Method G.

Formation of tetrahydrobenzothiadiazines-1,1-dioxides from 2-aminobenzenesulfonamides.

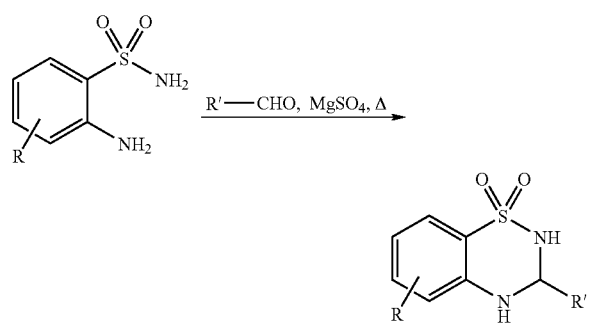

A stirred solution of the 2-aminobenzenesulfonamide derivative (7 mmol), an aldehyde (10 mmol) and MgSO$_4$ (20 mmol) in dry THF or dry dioxane (40 ml) was refluxed under N$_2$ until TLC indicated complete consumption of the 2-aminobenzenesulfonamide derivative (typically 12–36 h). The reaction mixture was filtered, at the precipitate washed thoroughly with THF or dioxane. The filtrate was evaporated to dryness, added water and extracted with EtOAc. The combined organic fractions were dried with MgSO$_4$ and evaporated to dryness. Column chromatography (EtOAc/hexane) afforded the pure product. Yields typically ranged from 25–75%.

Method H.

Formation of Aryl or Hetaryl Substituted Compounds by Use of Pd Catalyzed Cross Coupling.

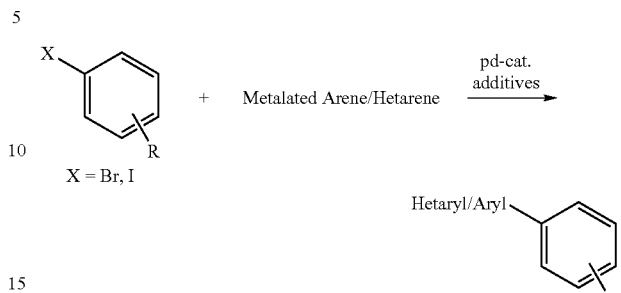

Suzuki coupling: A stirred mixture of an arylhalide (2 mmol), an aryl or hetarylboronic acid, boronic acid ester or dialkylborane (6 mmol), K$_2$CO$_3$ (10 mmol), Pd(PPh$_3$)$_4$ (30 mg), 1,3-propanediol (10 mmol), dimethoxyethane (50 ml) and H$_2$O (25 ml) under N$_2$ was heated to 70° C. for 3 h. The reaction mixture was cooled to rt. Further water was added and the reaction mixture was extracted with EtOAc. The combined organic fractions were dried with MgSO$_4$ and evaporated to dryness. Column chromatography afforded the pure product. Yields ranged from 40–100%.

Method I.

Formation of Compounds Containing Triazolyl Substitution.

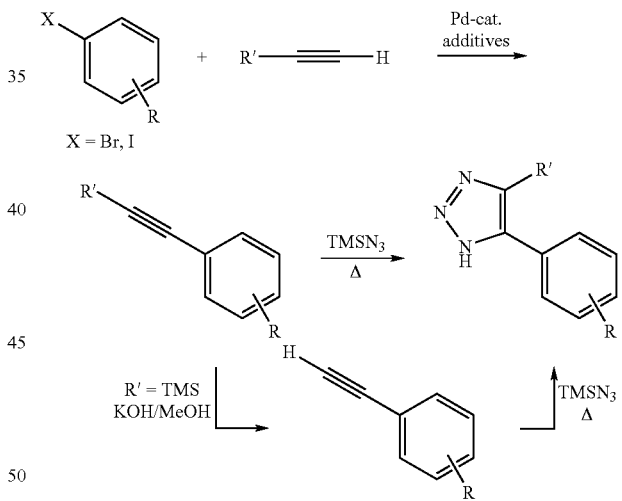

Sonogashira coupling: A mixture of an aryliodide or arylbromide (2 mmol); an acetylene (10 mmol); Pd(PPh$_3$)$_2$Cl$_2$ (140 mg; 0.2 mmol); CuI (40 mg; 0.1 mmol) and triethylamine (10 ml) under N$_2$ was stirred at rt. (in the case of arylbromides prolonged heating at 60° C. was necessary) over night. THF was added and the reaction mixture filtered through celite and the filtrate evaporated to dryness. Column chromatography gave the ethynylated arene. Yields ranged from 40–53% for arylbromides to 97% for aryliodides.

Detrimethylsilylation for R'=TMS: A solution of the ethynylated arene (1.7 mmol) in MeOH (8 ml) was added a solution of 1M KOH in MeOH (2 ml; 2 mmol) and stirred at rt. for 2 h. The reaction mixture was diluted with THF, adsorbed onto silica and chromatographed to give the desilylated ethynyl arene. Yields ranged from 61% to 73%.

Formation of trizoles: The ethynylarene (0.7 mmol) and TMS—N$_3$ (2 ml; 15 mmol) was heated to 170° C. in an ampule for 50 h. The reaction mixture was cooled to rt. and evaporated to nearly dryness (CAUTION! Evaporation to dryness may lead to explosion due to the presence of some HN$_3$) and added MeOH. The reaction mixture was stirred for 1 h (to remove the TMS-group in the TMS-triazole), then adsorbed onto silica, and purified by chromatography. Yields ranged from 20–72%.

Synthesis of Individual Compounds

Compound 1

2-Cyclohexyl-4-oxo-1,2,3,4-tetrahydroquinazoline

Anthranilamide was transformed by Method G (using cyclohexanecarboxaldehyde). M.p. 172–174° C.

Compound 2

2-Phenyl-4-oxo-1,2,3,4-tetrahydroquinazoline

Anthranilamide was transformed by Method G (using benzaldehyde). M.p. 221–222° C.

Compound 3

2-Methyl-3,4-dihydro-1,3-benzoxazine-4-one

2-Hydroxybenzamide was transformed by Method G (using paraldehyde). M.p. 124–126° C.

Compound 4

2-Phenyl-3,4-dihydro-1,3-benzoxazine-4-one

2-Hydroxybenzamide was transformed by Method G (using benzaldehyde). M.p. 157–160° C.

Compound 5

3-Bicyclo[2.2.1]hept-5'-en-2'-yl-1,2,3,4-tetrahydro-1,2,4-benzothiadiazine-1,1-dioxide 2-Aminobenzenesulfonamide was transformed by Method G (using a racemic endo/exo mixture of 2-norbornencarboxaldehyde). M.p. 206–209° C.

Compound 6

3-Phenyl-1,2,3,4-tetrahydro-1,2,4-benzothiadiazine-1,1-dioxide

2-Aminobenzenesulfonamide was transformed by Method G (using benzaldehyde). M.p. 125.5–128.5° C.

Compound 7

1,2,3,5,10,10a-Hexahydrobenzo[e]pyrrolo[1,2-b]-1,2,4-thiadiazine-5,5-dioxide

2-Aminobenzenesulfonamide was used as starting material for the following transformation sequence: Method E (using 4-chlorobutanoyl chloride. The reaction mixture was NOT subjected to NaOH catalyzed ring closure, but dissolved in H$_2$SO$_4$ and heated at 100° C. for 72 h and precipitated on ice). M.p. 149–154° C.

Compound 8

2-Ethyl-2-methyl-3,4-dihydro-1,3-benzoxazine-4-one

2-Hydroxybenzamide was transformed by Method G (using 2-butanone). M.p. 76–78° C.

Compound 9

3-Cyclohexyl-6-(2-methoxyphenyl)-1,2,3,4-tetrahydro-1,2,4-benzothiadiazine-1,1-dioxide 3-Bromo-aniline was transformed by Method B (see compound 121) to give 4-bromo-2-aminobenzenesulfonamide.

A mixture of 4-bromo-2-aminobenzenesulfonamide (140 mg, 0.56 mmol), 2-methoxyphenylboronic acid (106 mg, 0.70 mmol), Pd(PPh$_3$)$_2$Cl$_2$ (20 mg, 5 mol %) in 1,2-dimethoxyethane (30 ml) and Na$_2$CO$_3$ (2M, 3 ml, 6 mmol) was refluxed under N$_2$ for 4 h. The solvents were removed under reduced pressure and the residue was treated with saturated NaHCO$_3$ (20 ml) and extracted with EtOAc (2×40 ml). The organic layer was washed with brine (20 ml), dried (Na$_2$SO$_4$) and the solvent was removed under reduced pressure. The product was purified by flash chromatography on SiO$_2$ using EtOAc:n-hexane (1:1, v/v) as eluent, yielding 155 mg (100%) of 2-amino-4-(2-methoxyphenyl)-benzenesulfonamide as colorless powder. The product was further transformed by Method G (using cyclohexanecarboxaldehyde). M.p. 219–221° C.

Compound 10

3-Cyclohexyl-6-(2-pyridyl)-1,2,3,4-tetrahydro-1,2,4-benzothiadiazine-1,1-dioxide 3-Aminophenylboronic acid hemisulphate (5.58 g, 30 mmol), 2-bromopyridine (2.7 ml, 28 mmol), Pd(PPh$_3$)$_2$Cl$_2$ (100 mg, 0.5 mol %), 2M K$_2$CO$_3$ (50 ml) were refluxed in 1,2-dimethoxyethane (50 ml) for 24 h under N$_2$. The mixture was diluted with CH$_2$Cl$_2$ (100 ml) and washed with sat. NaHCO$_3$ (50 ml). The organic layer was dried (Na$_2$SO$_4$) and the solvent was removed under reduced pressure. Flash-chromatography with CH$_2$Cl$_2$ as eluent gave 3-(2-pyridyl) aniline as a yellow oil, 1.0 g (21%). 3-(2-Pyridyl)aniline was transformed by Method B and Method G (using cyclohexanecarboxaldehyde). M.p. 213–216° C.

Compound 11

3-Cyclohexyl-6-(3-pyridyl)-1,2,3,4-tetrahydro-1,2,4-benzothiadiazine-1,1-dioxide 3-Bromo-aniline was transformed by Method B (see compound 121) to give 4-bromo-2-aminobenzenesulfonamide.

A mixture of 4-bromo-2-aminobenzenesulfonamide (250 mg, 1.0 mmol), diethyl-3-pyridylborane (225 mg, 1.5 mmol), Pd(PPh$_3$)$_2$Cl$_2$ (35 mg, 5 mol %) in 1,2-dimethoxyethane (30 ml) and Na$_2$CO$_3$ (2M, 3 ml, 6 mmol) were refluxed under N$_2$ for 4 h. The solvents were removed under reduced pressure and the residue was treated with saturated NaHCO$_3$ (20 ml) and extracted with EtOAc (2×40 ml). The organic layer was washed with brine (20 ml), dried (Na$_2$SO$_4$) and the solvent was removed under reduced pressure. The product was purified by flash chromatography on SiO$_2$ using EtOAc:n-hexane (1:1, v/v) as eluent, yielding 240 mg (96%) of 2-amino-4-(3-pyridyl)-benzenesulfonamide as colorless powder. The product was further transformed by Method G (using cyclohexanecarboxaldehyde). M.p. 240–243° C.

Compound 12

3-Cyclohexyl-7-(1-hydroxyethyl)-1,2,3,4-tetrahydro-1,2,4-benzothiadiazine-1,1-dioxide 2-Amino-5-(1-hydroxyethyl)benzenesulfonamide: 5-Acetyl-2-aminobenzenesulfonamide (see compound 13) (0.95 g, 4.4 mmol) was suspended in 96% EtOH (50 ml) and NaBH$_4$ (0.46 g, 12 mmol) was added in one portion. The mixture was stirred at 25° C. for 4 h and filtered through Celite and the solvent was removed under reduced pressure. The residue was treated with sat. NaHCO$_3$ (50 ml) and extracted with EtOAc (2×50 ml), dried (Na$_2$SO$_4$) and evaporated to dryness. Flash-chromatography with EtOAc:n-hexane:Et$_3$N (200:100:4, v/v/v) as eluent gave 0.35 g (37%) of 2-amino-5-(1-hydroxyethyl)benzenesulfonamide as light-brown powder. M.p. 160–162° C.

Compound 13

3-Cyclohexyl-7-acetyl-1,2,3,4-tetrahydro-1,2,4-benzothiadiazine-1,1-dioxide

To a solution of ethylvinylether (5.8 ml, 60 mmol) in dry THF (50 ml) at −78° C. was added t-BuLi (1.7 M in pentane, 25 ml, 40 mmol) and the yellow mixture was stirred for 1 h at −78° C. The cooling bath was removed and the mixture was warmed slowly to 0° C. and stirred for another 30 min. The mixture was recooled to −78° C. and a solution of ZnCl$_2$ (2M in THF, 20 ml, 40 mmol) was added slowly and the cooling bath was removed and varmed to 20° C. 5-Iodo-2-aminobenzenesulfonamide (see compound 37) (1.8 g, 6 mmol) and Pd(PPh$_3$)$_4$ (0.2 g, 3 mol %) was added and the mixture was refluxed for 6 h. The THF was evaporated and the residue was boiled in 1 M hydrochloric acid (30 ml) and MeOH (30 ml) for 30 min. EDTA (14.6 g, 50 mmol) was added and made slightly basic (pH≈8–9) with 1 M NaOH followed by extraction with EtOAc (3×150 ml), drying (Na$_2$SO$_4$) and evaporation of the solvent gave a brown solid. Trituration with n-hexane gave 0.95 g (74%) of 5-acetyl-2-aminobenzenesulfonamide as off-white powder. The product was further transformed by Method G (using cyclohexanecarboxaldehyde). M.p. 224–226° C. (decomp).

Compound 14

3-Cyclohexyl-7-(1-hydroxyiminoethyl)-1,2,3,4-tetrahydro-1,2,4-benzothiadiazine-1,1-dioxide To a suspension of 5-acetyl-2-aminobenzenesulfonamide (see compound 13) (0.45 g, 2.1 mmol) in 96% EtOH (40 ml) was added H$_2$NOH.HCl (0.28 g, 4 mmol) and 2M NaOH (2 ml). The mixture was boiled for 2 h and the solvent was evaporated. The residue was triturated with water (25 ml) and the product was filtered off and dried, yielding 0.39 g (81%) of 2-amino-5-(1-hydroxyiminoethyl)benzenesulfonamide as yellow powder. The product was further transformed by Method G (using cyclohexanecarboxaldehyde). M.p. 230–233° C.

Compound 15

3-Cyclohexyl-7-carbamoyl-1,2,3,4-tetrahydro-1,2,4-benzothiadiazine-1,1-dioxide A mixture of 5-cyano-2-aminobenzenesulfonamide (see compound 37) (2 g; 10 mmol), conc. H$_2$SO$_4$ (4 ml) and abs. EtOH (4 ml) was heated to 80° C. for 5 h and over night at 50° C. The reaction mixture was poured onto ice and extracted with EtOAc (1×)*. The organic phase was discarded and the aqueous phase neutralized with Na$_2$CO$_3$ and extracted with EtOAc (3×). The organic phase was evaporated to dryness and subjected to column chromatography (EtOAc/hexane=2/1) to give 200 mg (9%) of the carboxamide. The carboxamide was further transformed by use of Method G (using cyclohexanecarboxaldehyde). M.p. 235–237° C.

*[The first extraction contains the nitrile (starting material) and another biproduct].

Compound 16

3-Cyclohexyl-7-ethoxycarbonyl-1,2,3,4-tetrahydro-1,2,4-benzothiadiazine-1,1-dioxide A mixture of 5-cyano-2-aminobenzenesulfonamide (see compound 37) (3 g; 15 mmol), conc. H$_2$SO$_4$ (5 ml) and abs. EtOH (15 ml) was heated to 80° C. over night. The reaction mixture was poured onto ice. The precipitate formed was isolated by filtration. The precipitate was washed with EtOAc to give 2.01 g (55%) of the pure ethyl ester. The ester was further transformed by use of Method G (using cyclohexanecarboxaldehyde). M.p. 234–236° C.

Compound 17

3-Cyclohexyl-7-cyano-1,2,3,4-tetrahydro-1,2,4-benzothiadiazine-1,1-dioxide

5-Cyano-2-aminobenzenesulfonamide (see compound 37) was transformed by Method G (using cyclohexanecarboxaldehyde). M.p. 234–237.

Compound 18

3-Bicyclo[2.2.1]hept-5'-en-2'-yl-7-phenyl-1,2,3,4-tetrahydro-1,2,4-benzothiadiazine-1,1-dioxide 5-Bromo-2-aminobenzenesulfonamide: A stirred solution of 2-aminobenzenesulfonamide (1.72 g; 10 mmol) in AcOH (15 ml) was added a solution of Br$_2$ (0.55 ml; 10.5 mmol) in AcOH (5 ml). The reaction mixture was poured into H$_2$O (100 ml) and filtered. The isolated solid was adsorbed onto silica and subjected to flash chromatography to give 1.428 g (57%) product (and 650 mg (20%) of the 3,5-dibromo derivative).

3-Bicyclo[2.2.1]hept-5'-en-2'-yl-7-phenyl-1,2,3,4-tetrahydro-1,2,4-benzothiadiazine-1,1-dioxide (18): 5-Bromo-2-aminobenzenesulfonamide was transformed by Method H (using phenylboronic acid) and Method G (using a racemic endo/exo mixture of bicyclo[2.2.1]hept-5-ene-2-carboxaldehyde). M.p. 190.5–195.0° C.

Compound 19

3-Cyclohexyl-7-(2'-acetamidophenyl)-1,2,3,4-tetrahydro-1,2,4-benzothiadiazine-1,1-dioxide 2-Nitrophenylboronic acid: A solution of phenylboronic acid (10 g; 82 mmol) in acetic acid anhydride (100 ml) at −15° C. was added fuming HNO₃ (5 ml; 120 mmol) over 30 min such that reaction temperature was kept below −10° C. The reaction mixture was allowed to warm up to rt. and left with stirring over night. The reaction mixture was poured onto ice and concentrated to 50 ml. The remanense was then re-evaporated 5 times from additional H₂O (100 ml) and finally filtered to give 7.1 g crude product as a mixture of isomers. Column chromatography (CH₂Cl₂/EtOH=10/0.5) gave 4.8 g (35%) pure product as an oil.

2-Acetamidophenylboronic acid: A mixture of 2-nitrophenylboronic acid (2 g; 12 mmol) and 5% Pd/C (100 mg) in EtOH (100 ml) was hydrogenated at 1 bar until TLC indicated complete conversion of starting material. The reaction mixture was filtered through celite and the filtrate evaporated to dryness. The remanense was washed with hexane and filtered to give 900 mg of (55%) 2-aminophenylboronic acid.

A mixture of 2-aminophenylboronic acid (900 mg; 6.6 mmol), triethylamine (0.57 ml; 7 mmol) and acetylchloride (0.5 ml; 7 mmol) was stirred at rt. for 1 h. The reaction mixture was evaporated to dryness, stirred with H₂O and filtered to give 750 mg (63%) product.

3-Cyclohexyl-7-(2'-acetamidophenyl)-1,2,3,4-tetrahydro-1,2,4-benzothiadiazine-1,1-dioxide (19): 5-Iodo-2-aminobenzenesulfonamide (see compound 37) was transformed by Method H (using 2-Acetamidophenylboronic acid) and Method G (using cyclohexanecarboxaldehyde). M. p. 245–249° C.

Compound 20

3-Cyclohexyl-7-(2'-nitrophenyl)-1,2,3,4-tetrahydro-1,2,4-benzothiadiazine-1,1-dioxide 5-Iodo-2-aminobenzenesulfonamide (see compound 37) was transformed by Method H (using 2-nitrophenylboronic acid (see compound 19)) and Method G (using cyclohexanecarboxaldehyde). M.p. 204–207° C.

Compound 21

3-Cyclohexyl-7-(2'-methoxyphenyl)-1,2,3,4-tetrahydro-1,2,4-benzothiadiazine-1,1-dioxide 5-Iodo-2-aminobenzenesulfonamide (see compound 37) was transformed by Method H (using 2-methoxyphenylboronic acid) and Method G (using cyclohexanecarboxaldehyde). M.p. 219–222° C.

Compound 22

3-Cyclohexyl-7-(2'-methoxy-4'-trifluoromethylphenyl)-1,2,3,4-tetrahydro-1,2,4-benzothiadiazine-1,1-dioxide 4-Trifluoromethylanisole: Sodium (12.78 g; 555 mmol) was added to dry MeOH (100 ml). When the gas evolution ceased, the reaction mixture was evaporated to dryness and dry NMP (250 ml) followed by Cu (s) (35.3; 555 mmol) and 4-bromo-trifluoromethylbenzene (25 g; 111 mmol) was added. The reaction mixture was heated to 130° C. for 4 h, cooled to rt. and filtered. Water (500 ml) was added to the filtrate and it was extracted with Et₂O (2×200 ml). The combined organic fractions were washed with H₂O (2×100 ml), dried (MgSO₄) and evaporated to dryness. Column chromatography gave 8.05 g (41%) of product.

2-Methoxy-5-trifluoromethylphenylboronic acid: A solution of 4-trifluoromethylanisole (8 g; 45 mmol) in dry THF (80 ml) at −30° C. under N₂ was added a solution of 2.5 M n-BuLi in hexane (20 ml; 50 mmol). The reaction mixture was stirred for 1 h at −30° C., then cooled to −70° C. and added B(Oi-Pr)₃ (14.1 ml; 64 mmol). The reaction mixture was allowed to slowly warm up to rt. over night. The reaction mixture was added 2 M HCl (40 ml) and THF was removed by evaporation. The aqueous remanense was extracted with Et₂O (4×20 ml) and the combined organic fractions were extracted with 1 M NaOH (5×17 ml). The combined aqueous fractions were neutralized by 10 M HCl. The precipitate formed was isolated by filtration and washed with 1 M HCl to give 8.1 g (81%) product.

3-Cyclohexyl-7-(2'-methoxy-4'-trifluoromethylphenyl)-1,2,3,4-tetrahydro-1,2,4-benzothiadiazine-1,1-dioxide (22): 5-Iodo-2-aminobenzenesulfonamide (see compound 37) was transformed by Method H (using 2-methoxy-5-trifluoromethylphenylboronic acid) and Method G (using cyclohexanecarboxaldehyde). M.p. 255–257° C.

Compound 23

3-Cyclohexyl-7-(2',4'-dimethoxyphenyl)-1,2,3,4-tetrahydro-1,2,4-benzothiadiazine-1,1-dioxide 5-Iodo-2-aminobenzenesulfonamide (see compound 37) was transformed by Method H (using 2,4-dimethoxyphenylboronic acid) and Method G (using cyclohexanecarboxaldehyde). M.p. 208–213° C.

Compound 24

3-Cyclohexyl-7-(2'-(N,N-dimethylsulfamoyl)phenyl)-1,2,3,4-tetrahydro-1,2,4-benzothiadiazine-1,1-dioxide 2-(N,N-dimethylsulfamoyl)phenylboronic acid: A solution of benzenesulfonylchloride (10 ml; 78 mmol) in THF (100 ml) was added a 40% solution of dimethylamine in H₂O (20 ml; 160 mmol) such that the reaction temperature was kept below 50° C. The reaction mixture was stirred 1 h at rt. The reaction mixture was added H₂O and THF removed by evaporation. The precipitate formed was isolated by filtration and air dried to give 14 g (97%) of N,N-dimethylbenzenesulfonamide.

A solution of N,N-dimethylbenzenesulfonamide (9.25 g; 50 mmol) in dry Et₂O (150 ml) under N₂ was cooled to −70° C. and added a solution of 2.5 M n-BuLi in hexane (24 ml; 60 mmol) such that the reaction temperature was kept below −60° C. The cooling bath was removed and the reaction mixture allowed to slowly warm up to +20° C. The reaction mixture was re-cooled to −70° C. and B(Oi-Pr)₃ (16.1 ml; 70 mmol) was added. The reaction mixture was left cold and allowed to warm up over night, 1 M HCl (100 ml) was added and stirring was continued at rt. for 1 h. The reaction mixture was then extracted with Et₂O (2×50 ml) and the combined organic fractions extracted with 1 M NaOH (4×50 ml). The combined aqueous fractions were neutralized with 1 M HCl and extracted with Et₂O (4×100 ml). The combined organic fractions were dried (Na₂SO₄) and evaporated to dryness, washed with Et₂O/hexane to give 3.4 g (30%) product.

3-Cyclohexyl-7-(2'-(N,N-dimethylsulfamoyl)phenyl)-1,2,3,4-tetrahydro-1,2,4-benzothiadiazine-1,1-dioxide (24): 5-Iodo-2-aminobenzenesulfonamide (see compound 37) was transformed by Method H (using 2-(N,N-dimethylsulfamoyl)phenylboronic acid) and Method G (using cyclohexanecarboxaldehyde). M.p. 290–300° C.

Compound 25

3-Cyclohexyl-7-(2'-chlorophenyl)-1,2,3,4-tetrahydro-1,2,4-benzothiadiazine-1,1-dioxide 5-Iodo-2-aminobenzenesulfonamide (see compound 37) was transformed by Method H (using 2-chlorophenylboronic acid) and Method G (using cyclohexanecarboxaldehyde). M.p. 233–236° C.

Compound 26

3-Cyclohexyl-7-(2'-fluorophenyl)-1,2,3,4-tetrahydro-1,2,4-benzothiadiazine-1,1-dioxide 5-Iodo-2-aminobenzenesulfonamide (see compound 37) was transformed by Method H (using 2-fluorophenylboronic acid) and Method G (using cyclohexanecarboxaldehyde). M.p. 249–250° C.

Compound 27

3-Cyclohexyl-7-(3'-hydroxyphenyl)-1,2,3,4-tetrahydro-1,2,4-benzothiadiazine-1,1-dioxide 3-hydroxyphenylboronic acid: A stirred solution of 3-aminophenylboronic acid hemisulfate (6.2 g; 33.3 mmol) and 50% $H_2SO_4$ (3.7 ml; 33.3 mmol) in $H_2O$ (100 ml) at −2° C. was added a solution of $NaNO_2$ (2.5 g; 36.3 mmol) in $H_2O$ (20 ml) over 1 h. The reaction mixture was slowly added to a stirred solution of conc. $H_2SO_4$ (25 ml) in $H_2O$ (20 ml) at reflux. After complete addition, the reaction mixture was refluxed for 30 min., cooled, added activated charcoal, heated to reflux, cooled and filtered through celite. The filtrate was saturated with NaCl (s), filtered and extracted with $Et_2O$ (5×100 ml). The combined organic fractions were dried ($Na_2SO_4$) and evaporated to dryness to give 4.3 g (94%) product.

3-Cyclohexyl-7-(3'-hydroxyphenyl)-1,2,3,4-tetrahydro-1,2,4-benzothiadiazine-1,1-dioxide (27): 3-Hydroxyphenylboronic acid was transformed by Method H and Method G (using cyclohexanecarboxaldehyde). M.p. 238–246° C.

Compound 28

3-Cyclohexyl-7-(2'-pyridyl)-1,2,3,4-tetrahydro-1,2,4-benzothiadiazine-1,1-dioxide 4-(2'-Pyridyl)-2-aminobenzenesulfonamide: A stirred mixture of 5-iodo-2-aminobenzenesulfonamide (1 g; 3.3 mmol), 2-tributylstannylpyridine (5.5 g; 15 mmol), Pd(PPh$_3$)$_4$ (240 mg, 0.34 mmol) and Ag$_2$O (780 mg; 3.36 mmol) in DMF (50 ml) under $N_2$ was heated at 100° C. for 6 h and over night at rt. The reaction mixture was evaporated to dryness and resuspended and stirred in $H_2O$/EtOAc and finally filtered. The organic phase was isolated and the aqueous phase extracted with EtOAc (2×aq. vol.). The combined organic fractions were dried ($Na_2SO_4$), evaporated to dryness and subjected to column chromatography to give 200 mg (24%) product.

3-Cyclohexyl-7-(2'-pyridyl)-1,2,3,4-tetrahydro-1,2,4-benzothiadiazine-1,1-dioxide (28): 4-(2'-Pyridyl)-2-aminobenzenesulfonamide was transformed by Method G (using cyclohexanecarboxaldehyde). M.p. 222–224° C.

Compound 29

3-Cyclohexyl-7-(3'-pyridyl)-1,2,3,4-tetrahydro-1,2,4-benzothiadiazine-1,1-dioxide 5-Iodo-2-aminobenzenesulfonamide (see compound 37) was transformed by Method H (using diethyl-3-pyridylborane) and Method G (using cyclohexanecarboxaldehyde). M.p. 240–242° C.

Compound 30

3-Cyclohexyl-7-(2'-pyrimidinyl)-1,2,3,4-tetrahydro-1,2,4-benzothiadiazine-1,1-dioxide 4-((2,2-Dimethylpropanoyl)amino)phenylboronic acid: To a solution of 4-bromo-N-pivaloylaniline (1.56 g, 6 mmol) in dry THF (50 ml) at −78° C. was added t-BuLi (1.5 M in pentane, 13.3 ml, 20 mmol) and the yellow mixture was stirred for 1 h at −78° C. under $N_2$. The reaction was quenched with B(OCH$_3$)$_3$ (1.7 ml, 15 mmol) and stirred for another 1 h at −78° C. The reaction mixture was then warmed to room temperature and hydrolysed with 0.5 M hydrochloric acid (50 ml) and extracted with EtOAc (3×80 ml), dried ($Na_2SO_4$) and concentrated to ca. 40 ml. n-Hexane (120 ml) was added slowly and the colorless crystalline product was filtered off and dried, yielding 1.26 g (95%).

N-(4-(2-pyrimidinyl)phenyl)-2,2-dimethylpropanamide: A mixture of 4-((2,2-dimethylpropanoyl)amino)phenylboronic acid (2.0 g, 9 mmol), 2-chloropyrimidine (0.8 g, 7 mmol), Pd(PPh$_3$)$_2$Cl$_2$ (100 mg, 2 mol %) 1,2-dimethoxyethane (40 ml) and $Na_2CO_3$ (2M, 7 ml, 14 mmol) were refluxed under $N_2$ for 5 h. The mixture was diluted with 10% $Na_2CO_3$ (20 ml) and extracted with EtOAc (3×50 ml). The organic layer was dried ($Na_2SO_4$) and the solvent was removed in vacuo. The crude product was recrystallised from MeOH/water (1:1) yielding 0.52 g (85%) of N-(4-(2-pyrimidinyl)phenyl)-2,2-dimethylpropanamide as colorless crystals.

4-(2-Pyrimidinyl)aniline: N-(4-(2-pyrimidinyl)phenyl)-2,2-dimethylpropanamide (1.41 g, 5.48 mmol) was boiled in 6 M hydrochloric acid (40 ml) for 2 h. The mixture was cooled and made strongly basic with NaOH (s) and extracted with CH$_2$Cl$_2$ (2×50 ml), dried ($Na_2SO_4$) and the solvent was removed in vacuo. Trituration with n-hexane gave 0.83 g (88%) of 4-(2-pyrimidinyl)aniline as a light-yellow powder. The product was further transformed by Method B and Method G (using cyclohexanecarboxaldehyde). M.p. 236–238° C.

Compound 31

3-Cyclohexyl-7-(2'-furyl)-1,2,3,4-tetrahydro-1,2,4-benzothiadiazine-1,1-dioxide

5-Iodo-2-aminobenzenesulfonamide (see compound 37) was transformed by Method H (using furyl-2-boronic acid) and Method G (using cyclohexanecarboxaldehyde). M.p. 226–228° C.

Compound 32

3-Cyclohexyl-7-(3'-furyl)-1,2,3,4-tetrahydro-1,2,4-benzothiadiazine-1,1-dioxide

5-Iodo-2-aminobenzenesulfonamide (see compound 37) was transformed by Method H (using furyl-3-boronic acid) and Method G (using cyclohexanecarboxaldehyde). M.p. 204–205° C.

Compound 33

3-Cyclohexyl-7-(2'-thienyl)-1,2,3,4-tetrahydro-1,2,4-benzothiadiazine-1,1-dioxide 5-Iodo-2-aminobenzenesulfonamide (see compound 37) was transformed by Method H (using thienyl-2-boronic acid) and Method G (using cyclohexanecarboxaldehyde). M.p. 234–236° C.

Compound 34

3-Cyclohexyl-7-(1-methyl-1H-2-imidazolyl)-1,2,3,4-tetrahydro-1,2,4-benzothiadiazine-1,1-dioxide To a solution of 1-methylimidazole (4.8 ml, 60 mmol) in dry THF (120 ml) at −78° C. was added n-BuLi (2.5 M in hexane, 26 ml, 65 mmol) and the yellow mixture was stirred for 45 min at −78° C. A solution of $ZnCl_2$ (2M in THF, 75 ml, 150 mmol) was added slowly and the cooling bath was removed. The colorless solution was stirred for another 10 min at 0° C. 5-Iodo-2-aminobenzenesulfonamide (see compound 37) (2.1 g, 7 mmol) and $Pd(PPh_3)_4$ (0.5 g, 5 mol %) was added and the mixture was refluxed for 6 h. The THF was evaporated and the residue was treated with EDTA (53 g, 0.18 mol) and made slightly basic (pH g 8–9) with 1 M NaOH followed by extraction with EtOAc (3×150 ml), drying ($Na_2SO_4$) and evaporation of the solvent gave a dark oil. Flash-chromatography with 5% MeOH in $CH_2Cl_2$ as eluent gave 1.33 g (75%) of 2-amino-5-(1-methyl-1H-2-imidazolyl)-1-benzenesulfonamide as colorless crystals. The product was further transformed by Method G (using cyclohexanecarboxaldehyde). M.p. >250° C. (decomp).

Compound 35

3-Cyclohexyl-7-(1',2',3'-triazol-4'-yl)-1,2,3,4-tetrahydro-1,2,4-benzothiadiazine-1,1-dioxide 5-Iodo-2-aminobenzenesulfonamide (see compound 37) was transformed by Method I (using trimethylsilylacetylene) and Method G (using cyclohexanecarboxaldehyde). M.p. 230–234° C. (dec.).

Compound 36

3-Cyclohexyl-7-(5'-phenyl-1',2',3'-triazol-4'-yl)-1,2,3,4-tetrahydro-1,2,4-benzothiadiazine-1,1-dioxide 5-Iodo-2-aminobenzenesulfonamide (see compound 37) was transformed by Method I (using phenylacetylene) and Method G (using cyclohexanecarboxaldehyde). M.p. 231–232° C. (dec.).

Compound 37

3-Cyclohexyl-7-(5'-methyl-1',2',4'-oxadiazol-3-yl)-1,2,3,4-tetrahydro-1,2,4-benzothiadiazine-1,1-dioxide 5-Iodo-2-aminobenzenesulfonamide: To a cold (0° C.) stirred solution of 2-aminobenzenesulfonamide (17.2 g; 100 mmol) in $CHCl_3$ (200 ml) was added a solution of iodine monochloride (17.1 g; 105 mmol) in $CHCl_3$ (50 ml) over 1 h. The reaction mixture was slowly warmed up to rt. and left with stirring over night. The reaction mixture was filtered and the isolated solid was washed on the filter with $CHCl_3$ (3×20 ml), $NaHCO_3$ (sat. aq., 1×20 ml), $H_2O$ (4×50 ml). The isolated solid was air dried to give 27.3 g (92%) of product.

5-Cyano-2-aminobenzenesulfonamide: A mixture of 5-iodo-2-aminobenzene-sulfonamide (17.9 g; 60 mmol), $Zn(CN)_2$ (4.9 g; 41.9 mmol) and $Pd(PPh_3)_4$ (2.5 g; 2.2 mmol) in DMF (150 ml) under $N_2$ was heated to 80° C. for 2 h. The reaction mixture was poured into $NaHCO_3$ (sat. aq., 600 ml) and extracted with EtOAc (9×200 ml). The combined organic fractions were washed with $NaHCO_3$ (sat. aq.) and NaCl (sat. aq.), dried ($Na_2SO_4$), filtered and evaporated to dryness. The remanense was washed with water and hexane and filtered of to give 10.9 g (92%) of product.

5-(N-hydroxyamidino)-2-aminobenzenesulfonamide: A mixture of hydroxylamine hydrochloride (764 mg; 11 mmol) and NaOMe (616 mg; 11.4 mmol) in MeOH (10 ml) was stirred at rt. for 1 h and then added 5-cyano-2-aminobenzenesulfonamide (1 g; 5 mmol). The reaction mixture was left with stirring for 48 h and poured into water and extracted with EtOAc (2×50 ml). The combined organic fractions were dried ($Na_2SO_4$), evaporated to dryness and purified by column chromatography to give 200 mg (17%) of product.

3-Cyclohexyl-7-(5'-methyl-1',2',4'-oxadiazol-3-yl)-1,2,3,4-tetrahydro-1,2,4-benzothiadiazine-1,1-dioxide (37): A mixture of 5-(N-hydroxyamidino)-2-aminobenzenesulfonamide (200 mg; 0.9 mmol), NaOMe (50 mg; 1 mmol), EtOAc (5 ml), crushed MS3A (2 g) in anhydrous EtOH (20 ml) was heated over night at 70° C. The reaction mixture was evaporated to dryness, stirred with water and extracted with EtOAc. The combined organic fractions were dried ($Na_2SO_4$) and evaporated to dryness to a brown oil, which was subjected to transformation by Method G (using cyclohexanecarboxaldehyde) to give 8 mg product after chromatography. M.p. 249–251° C.

Compound 38

3-Cyclohexyl-7-acetamido-1,2,3,4-tetrahydro-1,2,4-benzothiadiazine-1,1-dioxide 7-Amino-3-cyclohexyl-1,2,3,4-tetrahydro-1,2,4-benzothiadiazine-1,1-dioxide: To a stirred solution of 7-amino-3-cyclohexyl-1,2-dihydro-1,2,4-benzothiadiazine-1,1-dioxide (0.5 g; 2 mmol) in dry THF (10 ml) at −70° C. was added a solution of 1.5 M DIBALH in toluene (2.7 ml; 4 mmol) under $N_2$. The reaction mixture was stirred for 2 h at −70° C.; 2 h at −40° C. and then warmed to 0° C. The reaction was quenched with $H_2O$ and stirred for 30 min. at 0° C. and left over night without stirring at +5° C. The mixture was evaporated to dryness, resuspended in MeOH and filtered. The isolated solid was washed thoroughly with MeOH and filtered. The combined filtrates was adsorped onto silica gel. Column chromatography (EtOAc) gave 200 mg of product.

7-Acetylamino-3-cyclohexyl-1,2,3,4-tetrahydro-1,2,4-benzothiadiazine-1,1-dioxide (38): A mixture of 7-amino-3-cyclohexyl-1,2,3,4-tetrahydro-1,2,4-benzothiadiazine-1,1-dioxide (100 mg; 0.26 mmol), acetylchloride (20 μl; 0.29 mol) and triethylamine (42 μl; 0.3 mmol) was stirred for 2 h at r.t. The reaction mixture was resuspended in $H_2O$ and filtered. The isolated solid was purified by column chromatography (EtOAc) to give 22 mg 27a. M.p. 202–206° C.

Compound 39

3-Cyclohexyl-7-methylsulfonylamino-1,2,3,4-tetrahydro-1,2,4-benzothiadiazine-1,1-dioxide 3-Cyclohexyl-1,2-dihydro-1,2,4-benzothiadiazine-1,1-dioxide: 2-Aminobenzenesulfonamide was transformed by Method E (using cyclohexanecarbonyl chloride).

3-Cyclohexyl-7-nitro-1,2-dihydro-1,2,4-benzothiadiazine-1,1-dioxide: To a stirred solution of $KNO_3$ (1.2 g; 11.5 mmol) and conc. $H_2SO_4$ (8 ml) at 5° C. was added a solution of 3-cyclohexyl-1,2-dihydro-1,2,4-benzothiadiazine-1,1-dioxide in conc. $H_2SO_4$ (8 ml). The reaction mixture was allowed to warm up to r.t. and left with stirring over night. The product was precipitated by slow addition of ice and isolated by filtration. The crude product (4.3 g) was used without further purification.

7-Amino-3-cyclohexyl-1,2-dihydro-1,2,4-benzothiadiazine-1,1-dioxide: A stirred suspension of 3-cyclohexyl-7-nitro-1,2-dihydro-1,2,4-benzothiadiazine-1,1-dioxide (4.2 g; 14 mmol) and 10% Pd/C (400 mg) in abs. EtOH (100 ml) was hydrogenated at 1 bar. After consumption of the calculated amount of $H_2$, the reaction mixture was filtered through celite. The celite was washed twice with DMF (75 ml) and the combined organic fractions were evaporated to dryness. The remanense was resuspended in EtOAc/i-PrOH and the precipitate formed, was isolated by filtration. The isolated solid was dissolved in 0.5 M NaOH (aq.) and reprecipitated with 4 M HCl (aq.). Filtration gave 1.6 g product.

7-Methylsulfonylamino-3-cyclohexyl-1,2-dihydro-1,2,4-benzothiadiazine-1,1-dioxide: A stirred solution of 7-amino-3-cyclohexyl-1,2-dihydro-1,2,4-benzothiadiazine-1,1-dioxide (1 g; 3.6 mmol) and triethylamine (1.2 ml; 8 mmol) in dry THF (25 ml) was added methanesulfonylchloride (0.6 ml; 8 mmol) and stirred at rt. for 2 h. The reaction mixture was evaporated to dryness, resuspended in $H_2O$/EtOAc and filtered. The filtrate was adsorbed onto silica gel. Column chromatography ($CH_2Cl_2$:acetone=9:1) gave 210 mg of product.

3-Cyclohexyl-7-methylsulfonylamino-1,2,3,4-tetrahydro-1,2,4-benzothiadiazine-1,1-dioxide (39): 7-Methylsulfonylamino-3-cyclohexyl-1,2-dihydro-1,2,4-benzothiadiazine-1,1-dioxide was transformed by Method F. M.p. 255–258° C.

Compound 40

3-Cyclohexyl-7-nitro-1,2,3,4-tetrahydro-1,2,4-benzothiadiazine-1,1-dioxide

3-Trifluoromethyl-1,2,4-benzothiadiazine-1,1-dioxide: 2-Aminobenzenesulfonamide was trifluoroacetyl protected by using Method C. A solution of this (1 g; 4 mmol) in $H_2SO_4$ (16 ml) at 0° C. was added solid $KNO_3$ (4.4 mmol). The reaction mixture was allowed to warm up to rt. and stirred over night. The reaction mixture was poured into ice water (150 ml), filtered and air dried to give 1.11 g (94%) of pure product as a yellow solid.

3-Cyclohexyl-7-nitro-1,2,3,4-tetrahydro-1,2,4-benzothiadiazine-1,1-dioxide (40): 3-Trifluoromethyl-1,2,4-benzothiadiazine-1,1-dioxide was subjected to the following transformation scheme: Method D and Method F (using cyclohexanecarboxaldehyde). M.p. 209–211° C.

Compound 41

3-Cyclohexyl-7-phenylsulfonyl-1,2,3,4-tetrahydro-1,2,4-benzothiadiazine-1,1-dioxide 4-Phenylsulfonylaniline was used as starting material for the following transformation sequence: Method B and Method G (using cyclohexanecarboxaldehyde). M.p. 243–245° C.

Compound 42

2-Cyclohexyl-1,2,3,4-tetrahydro-6-quinazoline sulfonamide

A solution of 2-aminobenzylamine (3 g; 25 mmol) in THF (50 ml) was added trifluoroacetic acid anhydride (3.8 ml; 27 mmol) and stirred at rt. for 2 h. The reaction mixture was evaporated to dryness, stirred with $H_2O$ and filtered. The crude product was transformed by Method A (using 25% $NH_3$ (aq.) as amine) and Method G (using cyclohexanecarboxaldehyde). M.p. 178–180° C.

Compound 43

3-Cyclohexyl-7-sulfamoyl-1,2,3,4-tetrahydro-1,2,4-benzothiadiazine-1,1-dioxide

4-Sulfamoylanthranilamide: A stirred solution of $ClSO_3H$ (20 ml) was added anthranilamide (7.5 g; 55 mmol) in small portions. The reaction mixture was heated to 100° C. for 1 h and then poured into ice water (300 ml). A precipitate formed, which was isolated by filtration and dried on the filter. The isolated solid was dissolved in 25% $NH_3$ (aq.) and stirred at rt. over night. The aqueous phase was washed with EtOAc and concentrated to 20 ml. The aqueous phase was saturated with NaCl (s) and extracted with THF (3×50 ml). The combined organic fractions were evaporated to dryness and subjected to column chromatography to yield 13 mg product.

3-Cyclohexyl-7-sulfamoyl-1,2,3,4-tetrahydro-1,2,4-benzothiadiazine-1,1-dioxide (43): 4-Sulfamoylanthranilamide was transformed by Method G (using cyclohexanecarboxaldehyde). Fab+ 310. $^1$H-NMR (DMSO-$d_6$): 8.1 (1H; br.), 8.0 (1H; d), 7.58 (1H; dd), 7.3 (1H; br.), 7.05 (2H; br.), 6.79 (1H; d), 4.5 (1H; m), 1.8–1.5 (6H; m), 1.2–1.0 (5H; m).

Compound 44

3-Cyclohexyl-7-sulfamoyl-1,2,3,4-tetrahydro-1,2,4-benzothiadiazine-1,1-dioxide

2-Amino-5-sulfamoylbenzenesulfonamide (see compound 101) was transformed by Method G (using cyclohexanecarboxaldehyde). M.p. 252–254° C.

Compound 45

3-Methyl-7-dimethylsulfamoyl-1,2,3,4-tetrahydro-1,2,4-benzothiadiazine-1,1-dioxide 3-Methyl-7-dimethylsulfamoyl-1,2-dihydro-1,2,4-benzothiadiazine-1,1-dioxide was reduced by use of Method F. M.p. 210–212° C.

Compound 46

2-Cyclohexyl-1,2,3,4-tetrahydro-6-quinazoline N,N-dimethylsulfonamide

A solution of 2-aminobenzylamine (3 g; 25 mmol) in THF (50 ml) was added trifluoroacetic acid anhydride (3.8 ml; 27 mmol) and stirred at rt. for 2 h. The reaction mixture was evaporated to dryness, stirred with $H_2O$ and filtered. The crude product was transformed by Method A (using dimethylamine as amine), Method D and Method G (using cyclohexanecarboxaldehyde). M.p. >300° C. MS (electrospray) M⁺ 323. ¹H-NMR (DMSO-d₆): 7.2 (1H; dd); 7.1 (1H; d); 6.68 (1H; br); 6.62 (1H; d); 3.85 (1H; s); 3.8 (2H; s); 2.2 (1H; br); 1.8–1.0 (11H; m).

Compound 47

3-Cyclohexyl-7-dimethylaminosulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using dimethylamine as amine), Method F. M.p. 243–245° C.

Compound 48

3-Cyclohexyl-7-(N,N-diethylamino)sulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using diethylamine as amine), Method F. M.p. 207–209° C.

Compound 49

3-Cyclohexyl-7-pyrrolidinosulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using pyrrolidine as amine), Method F. M.p. 244–246° C.

Compound 50

3-Methyl-7-piperidinosulfonyl-1,2,3,4-tetrahydro-1,2,4-benzothiadiazine-1,1-dioxide 2-Aminobenzenesulfonamide was used as starting material for the following transformation sequence: Method C, Method A (using piperidine as amine), Method D, Method G [using paraldehyde and a cat. amount of TsOH]. M.p. 255–256° C.

Compound 51

3-Cyclopropyl-7-piperidinosulfonyl-1,2,3,4-tetrahydro-1,2,4-benzothiadiazine-1,1-dioxide 2-Aminobenzenesulfonamide was used as starting material for the following transformation sequence: Method C, Method A (using piperidine as amine), Method D, Method G [using cyclopropancarboxaldehyde]. M.p. 228–231° C.

Compound 52

3-Isopropyl-7-piperidinosulfonyl-1,2,3,4-tetrahydro-1,2,4-benzothiadiazine-1,1-dioxide 2-Aminobenzenesulfonamide was used as starting material for the following transformation sequence: Method C, Method A (using piperidine as amine), Method D, Method G [using isobutyraldehyde]. M.p. 237–239° C.

Compound 53

3-propyl-7-piperidinosulfonyl-1,2,3,4-tetrahydro-1,2,4-benzothiadiazine-1,1-dioxide 2-Aminobenzenesulfonamide was used as starting material for the following transformation sequence: Method C, Method A (using piperidine as amine), Method D, Method G [using butyraldehyde]. M.p. 147.4–151.2° C.

Compound 54

3-Benzyl-7-piperidinosulfonyl-1,2,3,4-tetrahydro-1,2,4-benzothiadiazine-1,1-dioxide 2-Aminobenzenesulfonamide was used as starting material for the following transformation sequence: Method C, Method A (using piperidine as amine), Method D, Method G [using phenylacetaldehyde]. M.p. 242–244° C.

Compound 55

3-Cyclopentyl-7-piperidinosulfonyl-1,2,3,4-tetrahydro-1,2,4-benzothiadiazine-1,1-dioxide Cyclopentanecarboxaldehyde: A stirred solution of cyclopentanecarboxylic acid (2.16 ml; 20 mmol) in dry THF (50 ml) at rt. under N₂ was added NaBH₄ (2.28 g; 60 mmol) and left with stirring for 20 min. The reaction mixture was cooled to 0° C. and added BF₃OEt₂ (10 ml; 80 mmol) over 1 h, while the reaction temperature was kept below +3° C. The reaction mixture was allowed to warm up to rt. and left with stirring over night. The reaction mixture was added NaHCO₃ (sat., aq.), H₂O and extracted with EtOAc. The combined organic fractions were washed with NaCl (sat., aq.), dried (Na₂SO₄) and evaporated to dryness to give 1.4 g of an oil which was used without further purification.

The oil (1.4 g) was dissolved in CH₂Cl₂ (75 ml) and added PCC on Al₂O₃ (30 g; 30 mmol)* and left with stirring for 1 h at rt. The reaction mixture was filtered and the filtrate evaporated onto silica. Column chromatography afforded the pure aldehyde which was used as a solution in CH₂Cl₂.
*[see Cheng Y.-S, Liu W.-L. and Chen S.-H., *Synthesis*, (1980) 223.]

3-Cyclopentyl-7-piperidinosulfonyl-1,2,3,4-tetrahydro-1,2,4-benzothiadiazine-1,1-dioxide (55): 2-Aminobenzenesulfonamide was used as starting material for the following transformation sequence: Method C, Method A (using piperidine as amine), Method D, Method G [using cyclopentanecarboxaldehyde]. M.p. 258–260° C.

Compound 56

3-Cyclohexyl-7-piperidinosulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using piperidine as amine), Method F. M.p. 262–264° C.

Compound 57

3-Bicyclo[2.2.1]hept-5'-en-2'-yl-7-piperidinosulfonyl-1,2,3,4-tetrahydro-1,2,4-benzothiadiazine-1,1-dioxide 2-Aminobenzenesulfonamide was used as starting material for the following transformation sequence: Method C, Method A (using piperidine as amine), Method D, Method G [using a racemic endo/exo mixture of 2-norbornencarboxaldehyde]. Two separate diastereomeric mixtures were isolated with m.p. (A) 240–242° C. and m.p. (B) 234–238° C.

Compound 58

3-Cyclohexyl-7-(1',2',3',6'-tetrahydropiperidino)sulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using 1,2,3,6-tetrahydropyridine as amine), Method F. M.p. 237–239° C.

Compound 59

3-Cyclohexyl-7-(N-methyl-N-phenylamino)sulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using N-methylaniline as amine), Method F. M.p. 210–212° C.

Compound 60

3-Cyclohexyl-7-(1'-(1',2',3',4'-tetrahydroquinolinyl))sulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using 1,2,3,4-tetrahydroquinoline as amine), Method F. M.p. 218–220° C.

Compound 61

3-Cyclohexyl-7-(4'-methylpiperazino)sulfonyl-1,2,3,4-tetrahydro-1,2,4-benzothiadiazine-1,1-dioxide 2-Aminobenzenesulfonamide was used as starting material for the following transformation sequence: Method C, Method A (using N-methylpiperazine as amine), Method D, Method G (using cyclohexanecarboxaldehyde). M.p. 227–229° C.

61 methane sulfonate salt: 61 (0.6 g; 1.4 mmol) was dissolved in 99% EtOH (30 ml) and added a solution of 1 M $CH_3SO_3H$ in 99% EtOH. The mixture was left for precipitation for 2 h and the salt isolated by filtration. The composition of the salt was checked by HPLC for stability compared to the free base. The salt was found to be stable towards hydrolysis under these conditions and had a water solubility of 10 mg/ml.

Compound 62

3-Cyclohexyl-7-(4'-methylsulfonylpiperazino)sulfonyl-1,2,3,4-tetrahydro-1,2,4-benzothiadiazine-1,1-dioxide N-Mesylpiperazinium chloride: To a stirred solution of piperazine (4.3 g; 50 mmol) in $CH_2Cl_2$ (50 ml) at +5 C. was added a solution of $CH_3SO_2Cl$ (4.25 ml; 55 mmol) in $CH_2Cl_2$ (15 ml). The thick reaction mixture was stirred at rt. for 12 h, added $CH_2Cl_2$ (100 ml), and extracted with 1 M HCl (300 ml). A precipitate formed in the aqueous phase was filtered of to give 2.66 g of N-mesylpiperazinium chloride (32%).

3-Cyclohexyl-7-(4'-methylsulfonylpiperazino)sulfonyl-1,2,3,4-tetrahydro-1,2,4-benzothiadiazine-1,1-dioxide (62): 2-Aminobenzenesulfonamide was used as starting material for the following transformation sequence: Method E (using cyclohexanecarbonyl chloride), Method A (using N-Mesylpiperazinium chloride as amine (1.5 eq.), 3 eq. $K_2CO_3$ was used for neutralization), Method F. M.p. 272–274° C.

Compound 63

3-Cyclohexyl-7-morpholinosulfonyl-1,2,3,4-tetrahydro-1,2,4-benzothiadiazine-1,1-dioxide 2-Aminobenzenesulfonamide was used as starting material for the following transformation sequence: Method E (using cyclohexanecarbonyl chloride), Method A (using morpholine as amine), Method F. M.p. 262–264° C.

Compound 64

3-Bicyclo[2.2.1]hept-5'-en-2'-yl-7-bromo-1,2,3,4-tetrahydro-1,2,4-benzothiadiazine-1,1-dioxide 5-Bromo-2-aminobenzenesulfonamide (see compound 18) was transformed by Method G (using a racemic endo/exo mixture of bicyclo[2.2.1]hept-5-ene-2-carboxaldehyde). M.p. 200–204° C.

Compound 65

2-Methyl-4-oxo-3,4-dihydro-6-quinazoline-N,N-dimethylsulfonamide

2-Methyl-4-oxo-3,4-dihydroquinazoline: A solution of anthranilamide (13.6 g; 100 mmol) in acetic acid (100 ml) was refluxed for 60 h. The reaction mixture was evaporated to dryness, suspended in $H_2O$, filtered and washed thoroughly with $NaHCO_3$ until the filtrate had a pH of 8–8.5.

2-Methyl-4-oxo-3,4-dihydro-6-quinazoline-N,N-dimethylsulfonamide: 2-Methyl-4-oxo-3,4-dihydroquinazoline was transformed by Method A (using dimethylamine as amine). M.p. 264–266° C.

Compound 66

2-Trifluoromethyl-4-oxo-3,4-dihydro-6-quinazoline sulfonamide

2-Trilfluoroacetamidobenzamide (see compound 68) was transformed by Method A (Using 0.5 M $NH_3$ in THF as amine). M.p. 311–314° C.

Compound 67

2-Trifluoromethyl-4-oxo-3,4-dihydro-6-quinazoline N,N-dimethylsulfonamide

2-Trilfluoroacetamidobenzamide (see compound 68) was transformed by Method A (Using dimethylamine as amine). M.p. 257–258° C.

Compound 68

2-Trifluoromethyl-4-oxo-3,4-dihydro-6-quinazoline-1',2',3',6'-tetrahydropiperidinosulfonamide A stirred mixture of anthranilamide (13.6 g; 100 mmol) in THF (100 ml) at 100° C. was added trifluoroacetic acid anhydride (15.2 ml; 110 mmol) and allowed to warm up to rt. and left with stirring over night. The reaction mixture was evaporated to dryness, suspended in $H_2O$ and filtered. The isolated solid was air dried to give 21.6 g (93%) 2-trilfluoroacetamidobenzamide. 2-Trifluoroacetamidobenzamide was transformed by Method A (using 1,2,3,6-tetrahydropyridine as amine). M.p. 227–230° C.

Compound 69

2-Trifluoromethyl-4-oxo-3,4-dihydro-6-quinazoline N-cyclohexylsulfonamide

2-Trilfluoroacetamidobenzamide (see compound 68) was transformed by Method A (Using cyclohexylamine as amine). M.p. 261–263° C.

Compound 70

2-Trifluoromethyl-4-oxo-3,4-dihydro-6-quinazoline morpholinosulfonamide

2-Trilfluoroacetamidobenzamide (see compound 68) was transformed by Method A (Using morpholine as amine). M.p. 282–285° C.

Compound 71

2-Cyclohexyl-4-oxo-3,4-dihydro-6-quinazoline-N,N-dimethylsulfonamide

Antranilamide was used as starting material for the following transformation sequence: Method A (Using 25% $NH_3$ (aq.) as amine. The reaction mixture contained both the 5-mono and 5,7-disulfonamide, which were separated by chromatography), Method G (using cyclohexanecarboxaldehyde. The aminal auto oxidizes to the aromatic hydroxyquinazoline). M.p. 306–310° C.

Compound 72

3-Methyl-7-sulfamoyl-1,2-dihydro-1,2,4-benzothiadiazine-1,1-dioxide

3-Methyl-1,2-dihydro-1,2,4-benzothiadiazine-1,1-dioxide (see compound 73) was transformed by Method A (using 0.5M $NH_3$ in THF as amine). M.p. 295–297° C.

Compound 73

3-Methyl-7-dimethylsulfamoyl-1,2-dihydro-1,2,4-benzothiadiazine-1,1-dioxide

2-Aminobenzenesulfonamide (17.2 g; 100 mmol) was refluxed in AcOH for 5 days. The precipitate formed was isolated by filtration and washed with water to give 17.8 g (91%) of 3-methyl-1,2-dihydro-1,2,4-benzothiadiazine-1,1-dioxide. 3-Methyl-1,2-dihydro-1,2,4-benzothiadiazine-1,1-dioxide was transformed by Method A (using dimethylamine as amine). M.p. 260–261° C.

Compound 74

3-Methyl-7-(1',2',3',6'-tetrahydropiperidino)sulfonyl-1,2-dihydro-1,2,4-benzothiadiazine-1,1-dioxide 3-Methyl-1,2-dihydro-1,2,4-benzothiadiazine-1,1-dioxide (see compound 73) was transformed by Method A (using 1,2,3,6-tetrahydropiperidine as amine). M.p. 265–268° C.

Compound 75

3-Methyl-7-cyclohexylsulfamoyl-1,2-dihydro-1,2,4-benzothiadiazine-1,1-dioxide 3-Methyl-1,2-dihydro-1,2,4-benzothiadiazine-1,1-dioxide (see compound 73) was transformed by Method A (using cyclohexylamine as amine). M.p. 239–242° C.

Compound 76

3-Trifluoromethyl-7-dimethylsulfamoyl-1,2-dihydro-1,2,4-benzothiadiazine-1,1-dioxide 2-Aminobenzenesulfonamide was used as starting material for the following transformation sequence: Method C and Method A (using dimethylamine as amine). M.p. 240–242° C.

Compound 77

2-Trifluoromethyl-4-oxo-3,4-dihydro-6-quinazoline-sulfonic acid

2-Aminobenzenesulfonamide was used as starting material for the following transformation sequence: Method C and Method A (using NaOH instead of an amine). M.p. >330° C.

Compound 78

3-Cyclohexyl-8-methyl-1,2,3,4-tetrahydro-1,2,4-benzothiadiazine-1,1-dioxide m-Toluidine was used as starting material for the following transformation sequence: Method B [2-amino-6-methylbenzenesulfonamide was separated from 2-amino-4-methylbenzenesulfonamide by recrystallization (EtOAc/hexane)]. 2-Amino-6-methylbenzenesulfonamide was further purified by column chromatography and transformed by Method G (using cyclohexanecarboxaldehyde). M.p. 228–230° C.

Compound 79

3-Cyclohexyl-8-hydroxymethyl-1,2,3,4-tetrahydro-1,2,4-benzothiadiazine-1,1-dioxide 5-Chloro-3-cyclohexyl-1,2-dihydro-1,2,4-benzothiadiazine-1, 1-dioxide-8-carboxylic acid: To a solution of 5-chloro-3-cyclohexyl-1,2-dihydro-1,2,4-benzothiadiazine-1,1-dioxide (see compound 80) (0.30 g, 1.0 mmol) in dry THF (15 ml) at −78° C. was added s-BuLi in cyclohexane (1.3 M, 1.6 ml, 2.1 mmol) under $N_2$. The yellow mixture was stirred for 15 min at −78° C. and dry gaseous $CO_2$ was bubbled through the solution for 30 min. The cooling bath was removed and the mixture was allowed to warm to 0° C. The solvent was removed under reduced pressure and the residue was triturated with hydrochloric acid (0.2 M, 12 ml). The crude product was recrystallised from 50% MeOH yielding 300 mg (82%) of 5-chloro-3-cyclohexyl-1,2-dihydro-1,2,4-benzothiadiazine-1,1-dioxide-8-carboxylic acid as colorless crystals.

3-Cyclohexyl-1,2-dihydro-1,2,4-benzothiadiazine-1,1-dioxide-8-carboxylic acid: 5-Chloro-3-cyclohexyl-1,2-dihydro-1,2,4-benzothiadiazine-1,1-dioxide-8-carboxylic acid (160 mg, 0.47 mmol) was dissolved in 99% EtOH (50 ml) and hydrogenated using Pd/C (10%, 10 mg) at 1 bar pressure for 24 h. NaOH (1 M, 12 ml) was added and the mixture was filtered through a pad of Celite™ and concentrated to 10 ml and concentrated hydrochloric acid was added slowly to precipitate the product yielding 110 mg (76%) of 3-cyclohexyl-1,2-dihydro-1,2,4-benzothiadiazine-1,1-dioxide-8-carboxylic acid as colorless powder.

3-Cyclohexyl-8-hydroxymethyl-1,2,3,4-tetrahydro-1,2,4-benzothiadiazine-1,1-dioxide (79): $NaBH_4$ in triglyme (2M, 0.75 ml, 1.5 mmol) was dissolved in dry THF (20 ml) and cooled to −50° C. under $N_2$. $BF_3$-etherate (0.25 ml, 2.0 mmol) was added and the mixture was stirred for 10 min at −50° C. Solid 3-cyclohexyl-1,2-dihydro-1,2,4-benzothiadiazine-1,1-dioxide-8-carboxylic acid (170 mg, 0.55 mmol) was added in one portion and the suspension was stirred for 6 h at −50° C. and overnight at 20° C. The mixture was hydrolysed with hydrochloric acid (1M, 2 ml) and the solvent was removed under reduced pressure. The residue was extracted with EtOAc (50 ml) and the organic layer was washed with brine (10 ml), dried ($Na_2SO_4$) and the evaporated to dryness. The product was purified by flash chromatography on $SiO_2$ using EtOAc:n-hexane (2:1, v/v) as eluent, yielding 100 mg (62%) of 3-cyclohexyl-8-hydroxymethyl-1,2-dihydro-1,2,4-benzothiadiazine-1,1-dioxide as colorless needles. The product was further transformed by Method F. M.p. 220–223° C.

Compound 80

3-Cyclohexyl-8-(2-methoxyphenyl)-1,2,3,4-tetrahydro-1,2,4-benzothiadiazine-1,1-dioxide 5-Chloro-3-cyclohexyl-1,2-dihydro-1,2,4-benzothiadiazine-1,1-dioxide: 3-Chloroaniline was used as starting material for the following transformation sequence: Method B followed by Method E (using cyclohexylcarbonyl chloride).

5-Chloro-3-cyclohexyl-8-iodo-1,2-dihydro-1,2,4-benzothiadiazine-1,1-dioxide: To a solution of 5-chloro-3-cyclohexyl-1,2-dihydro-1,2,4-benzothiadiazine-1,1-dioxide (596 mg, 2 mmol) in dry THF (20 ml) at −78° C. was added s-BuLi in cyclohexane (1.3 M, 3.8 ml, 5 mmol) under $N_2$. The yellow mixture was stirred for 15 min at −78° C. and a solution of $I_2$ (1.27 g, 5 mmol) in dry THF (5 ml) was added. The cooling bath was removed and the mixture was allowed to warm to 0° C. $NaHSO_3$ (5%, 20 ml) was added and extracted with EtOAc (2×30 ml), dried ($Na_2SO_4$) and evaporated to dryness to give 0.76 g (90%) of 5-chloro-3-cyclohexyl-8-iodo-1,2-dihydro-1,2,4-benzothiadiazine-1,1-dioxide.

5-Chloro-3-cyclohexyl-8-(2-methoxyphenyl)-1,2-dihydro-1,2,4-benzothiadiazine-1,1-dioxide: A mixture of 5-chloro-3-cyclohexyl-8-iodo-1,2-dihydro-1,2,4-benzothiadiazine-1,1-dioxide (290 mg, 0.68 mmol), 2-methoxyphenylboronic acid (122 mg, 0.80 mmol), $Pd(PPh_3)_2Cl_2$ (10 mg, 2 mol %) in 1,2-dimethoxyethane (50 ml) and $Na_2CO_3$ (2M, 2 ml, 4 mmol) were refluxed under $N_2$ for 2 h. The solvents were removed under reduced pressure and the residue was extracted with EtOAc (2×40 ml) and the organic layer was washed with saturated $NaHCO_3$ (20 ml), dried ($Na_2SO_4$) and the solvent was removed under reduced pressure. The product was purified by flash chromatography on $SiO_2$ using EtOAc:n-hexane (1:2, v/v) as eluent, yielding 200 mg (73%) of 5-chloro-3-cyclohexyl-8-(2-methoxyphenyl)-1,2-dihydro-1,2,4-benzothiadiazine-1,1-dioxide as colorless crystals.

3-Cyclohexyl-8-(2-methoxyphenyl)-1,2,3,4-tetrahydro-1,2,4-benzothiadiazine-1,1-dioxide (80): 5-Chloro-3-cyclohexyl-8-(2-methoxyphenyl)-1,2-dihydro-1,2,4-benzothiadiazine-1,1-dioxide (190 mg, 0.47 mmol) was dissolved in 99% EtOH (30 ml) and hydrogenated using Pd/C (10%, 10 mg) at 1 bar pressure. The mixture was filtered through a pad of Celite™ and the solvent was removed under reduced pressure yielding 174 mg (100%) of 5-chloro-3-cyclohexyl-8-(2-methoxyphenyl)-1,2-dihydro-1,2,4-benzothiadiazine-1,1-dioxide as colorless crystals. The product was transformed by Method F. M.p. 100–105° C.

Compound 81

3-Cyclohexyl-8-(3-methoxyphenyl)-1,2,3,4-tetrahydro-1,2,4-benzothiadiazine-1,1-dioxide Synthesis as for compound 80 (using 3-methoxyphenylboronic acid for the Pd-cat. cross coupling). M.p. 108–115° C.

Compound 82

3-Cyclohexyl-8-(2-pyridyl)-1,2,3,4-tetrahydro-1,2,4-benzothiadiazine-1,1-dioxide 5-Chloro-3-cyclohexyl-8-(dihydroxyboryl)-1,2-dihydro-1,2,4-benzothiadiazine-1,1-dioxide: To a solution of 5-chloro-3-cyclohexyl-1,2-dihydro-1,2,4-benzothiadiazine-1,1-dioxide (see compound 80) (0.60 g, 2.0 mmol) in dry THF (15 ml) at −78° C. was added s-BuLi in cyclohexane (1.3 M, 3.8 ml, 5 mmol) under $N_2$. The yellow mixture was stirred for 15 min at −78° C. and $B(OCH_3)_3$ (0.57 ml, 5 mmol) was added. The cooling bath was removed and the mixture was allowed to warm to 0° C. and stirred for another 1 h. The mixture was hydrolysed with hydrochloric acid (0.5 M, 12 ml) and extracted with EtOAc (2×50 ml), dried ($Na_2SO_4$) and evaporated to dryness to give 0.65 g (95%) of 5-chloro-3-cyclohexyl-8-(dihydroxyboryl)-1,2,4-benzothiadiazine-1,1-dioxide.

5-Chloro-3-cyclohexyl-8-(2-pyridyl)-1,2-dihydro-1,2,4-benzothiadiazine-1,1-dioxide: A mixture of 5-chloro-3-cyclohexyl-8-(dihydroxyboryl)-1,2-dihydro-1,2,4-benzothiadiazine-1,1-dioxide (440 mg, 1.28 mmol), 2-bromopyridine (0.14 ml, 1.50 mmol), $Pd(PPh_3)_2Cl_2$ (10 mg, 2 mmol %) in 1,2-dimethoxyethane (30 ml) and $Na_2CO_3$ (2M, 3 ml, 6 mmol) were refluxed under $N_2$ for 24 h. The solvents were removed under reduced pressure and the residue was treated with saturated $NH_4Cl$ (10 ml) and extracted with EtOAc (2×40 ml). The organic layer was washed with water (20 ml), dried ($Na_2SO_4$) and the solvent was removed under reduced pressure. The product was purified by flash chromatography on $SiO_2$ using EtOAc:n-hexane (2:1, v/v) as eluent, yielding 280 mg (58%) of 5-chloro-3-cyclohexyl-8-(2-pyridyl)-1,2-dihydro-1,2,4-benzothiadiazine-1,1-dioxide as colorless crystals.

3-Cyclohexyl-8-(2-pyridyl)-1,2,3,4-tetrahydro-1,2,4-benzothiadiazine-1,1-dioxide (82): 5-chloro-3-cyclohexyl-8-(2-pyridyl)-1,2-dihydro-1,2,4-benzothiadiazine-1,1-dioxide (0.268 g, 0.713 mmol) was dissolved in 99% EtOH (50 ml) and hydrogenated using Pd/C (10%, 10 mg) at 4 bar pressure for 24 h. The mixture was filtered through a pad of Celite™ and the solvent was removed under reduced pressure. The residue was dissolved in EtOAc (50 ml) and washed with phosphate buffer (pH=7, 10 ml), dried ($Na_2SO_4$) and the solvent was removed under reduced pressure, yielding 200 mg (82%) of 3-cyclohexyl-8-(2-pyridyl)-1,2-dihydro-1,2,4-benzothiadiazine-1,1-dioxide as colorless crystals. The product was further transformed by Method F. M.p. 200–203° C.

Compound 83

3-Cyclohexyl-8-methoxy-1,2,3,4-tetrahydro-1,2,4-benzothiadiazine-1,1-dioxide m-Anisidine was used as starting material for the following transformation sequence: Method B [2-amino-6-methoxybenzenesulfonamide was separated from 2-amino-4-methoxybenzenesulfonamide by flash chromatography (EtOAc/hexane)] and then Method G (using cyclohexanecarboxaldehyde). M.p. 221–223° C.

Compound 84

5,7-Dibromo-1,2-dihydro-1,2,4-benzothiadiazine-1,1-dioxide

2-Amino-3,5-dibromobenzenesulfonamide (see compound 125) was transformed by Method G (using ethylformiat and a catalytic amount of triethylamine). M.p. 289–292° C.

Compound 85 and Compound 86

3-Cyclohexyl-2-methyl-7-morpholinosulfonyl-1,2,3,4-tetrahydro-1,2,4-benzothiadiazine-1,1-dioxide (85) and 3-Cyclohexyl-4-methyl-7-morpholinosulfonyl-1,2,3,4-tetrahydro-1,2,4-benzothiadiazine-1,1-dioxide (86)

3-Cyclohexyl-7-morpholinosulfonyl-1,2-dihydro-1,2,4-benzothiadiazine-1,1-dioxide: 2-Aminobenzenesulfonamide was used as starting material for the following transformation sequence: Method E (using cyclohexanecarbonyl chloride) and Method A (using morpholine as amine) which gave 3-cyclohexyl-7-morpholinosulfonyl-1,2-dihydro-1,2,4-benzothiadiazine-1,1-dioxide.

3-Cyclohexyl-2-methyl-7-morpholinosulfonyl-1,2-dihydro-1,2,4-benzothiadiazine-1,1-dioxide and 3-cyclohexyl-4-methyl-7-morpholinosulfonyl-1,2-dihydro-1,2,4-benzothiadiazine-1,1-dioxide: A mixture of 3-cyclohexyl-7-morpholinosulfonyl-1,2-dihydro-1,2,4-benzothiadiazine-1,1-dioxide (2 g; 5 mmol), DEAD (2.35 ml; 15 mmol), $PPh_3$ (4 g; 15 mmol) in dry THF (30 ml) as cooled to 0° C. and added MeOH (1.25 ml; 30 mmol). The reaction mixture was stirred over night at rt., evaporated to dryness, stirred with EtOAc and filtered. The isolated precipitate was stirred with $CH_2Cl_2$ and filtered to leave the 2-methyl isomer in the filtrate and the 4-methyl isomer as the precipitate.

The 4-methyl was purified by recrystalization from DMSO/$H_2O$. The 2-methyl isomer was purified by column chromatography (EtOAc).

3-Cyclohexyl-2-methyl-7-morpholinosulfonyl-1,2,3,4-tetrahydro-1,2,4-benzothiadiazine-1,1-dioxide (85): 3-Cyclohexyl-2-methyl-7-morpholinosulfonyl-1,2-dihydro-1,2,4-benzothiadiazine-1,1-dioxide was reduced by use of method F. M.p. 243–245° C.

3-Cyclohexyl-4-methyl-7-morpholinosulfonyl-1,2,3,4-tetrahydro-1,2,4-benzothiadiazine-1,1-dioxide (86): 3-Cyclohexyl-4-methyl-7-morpholinosulfonyl-1,2-dihydro-1,2,4-benzothiadiazine-1,1-dioxide was reduced by use of method F. M.p. 207–210° C.

Compound 87

7-Methylsulfonylamino-1,2,3,3a,4,5-hexahydrobenzo[e]pyrrolo[2,1-c]-1,2,4-thiadiazine-5,5-dioxide 1,2,3,5-tetrahydrobenzo[e]pyrrolo[2,1-c]-1,2,4-thiadiazine-5,5-dioxide: 2-Aminobenzene-sulfonamide was transformed by Method E (using 4-chlorobutanoyl chloride).

7-Nitro-1,2,3,5-tetrahydrobenzo[e]pyrrolo[2, 1-c]-1,2,4-thiadiazine-5,5-dioxide: A stirred solution of 1,2,3,5-tetrahydrobenzo[e]pyrrolo[2,1-c]-1,2,4-thiadiazine-5,5-dioxide (222 mg; 1 mmol) in $H_2SO_4$ (2 ml) at 5° C. was added a solution of $KNO_3$ (122 mg; 1.2 mmol) in $H_2SO_4$ (2 ml). The reaction mixture was allowed to warm up to rt. and stirred for 2 h. The reaction mixture was poured into ice water, filtered and air dried to give 190 mg (71%) product.

7-Amino-1,2,3,5-tetrahydrobenzo[e]pyrrolo[2, 1-c]-1,2,4-thiadiazine-5,5-dioxide: A stirred solution of 7-nitro-1,2,3,3a,4,5-hexahydrobenzo[e]pyrrolo[2,1-c]-1,2,4-thiadiazine-5,5-dioxide (167 mg; 0.6 mmol) in dry THF (2 ml) at –50° C. was added $LiAlH_4$ (115 mg; 3 mmol) in one portion. The reaction mixture was allowed to warm up to rt. and stirred over night. The reaction mixture was quenched by addition of $H_2O$ and 10 M NaOH, stirred, filtered through celite and evaporated to dryness to give 150 mg product.

7-Methylsulfonylamino-1,2,3,3a,4,5-hexahydrobenzo[e]pyrrolo[2,1-c]-1,2,4-thiadiazine-5,5-dioxide (87): A stirred solution of 7-amino-1,2,3,3a,4,5-hexahydrobenzo[e]pyrrolo[2,1-c]-1,2,4-thiadiazine-5,5-dioxide (150 mg; 0.5 mmol) and triethylamine (70 µl; 0.5 mmol) in THF (1 ml) was added a solution of $CH_3SO_2Cl$ (40 µl; 0.5 mmol) in THF (1 ml) and stirred at rt. over night. The reaction mixture was evaporated to dryness, suspended in $H_2O$ and extracted by EtOAc. The combined organic fractions were evaporated to dryness. Column chromatography gave 40 mg product. M.p. 177–180° C.

Compound 88

7-Sulfamoyl-1,2,3,3a,4,5-hexahydrobenzo[e]pyrrolo[2,1-c]-1,2,4-thiadiazine-5,5-dioxide 2-Aminobenzenesulfonamide was used as starting material for the following transformation sequence: Method E (using 4-chlorobutanoyl chloride), Method A (using 0.5 M $NH_3$ in THF as amine), Method F (using $LiAlH_4$ and rt.). M.p. 260–262° C.

Compound 89

7-Methylsulfamoyl-1,2,3,3a,4,5-hexahydrobenzo[e]pyrrolo[2,1-c]-1,2,4-thiadiazine-5,5-dioxide 2-Aminobenzenesulfonamide was used as starting material for the following transformation sequence: Method E (using 4-chlorobutanoyl chloride), Method A (using methylamine as amine), Method F (using $LiAlH_4$ and rt.). M.p. 244–245° C.

Compound 90

7-Cyclohexylsulfamoyl-1,2,3,3a,4,5-hexahydrobenzo[e]pyrrolo[2,1-c]-1,2,4-thiadiazine-5,5-dioxide 2-Aminobenzenesulfonamide was used as starting material for the following transformation sequence: Method E (using 4-chlorobutanoyl chloride), Method A (using cyclohexylamine as amine), Method F (using LiAlH$_4$ and rt.). M.p. 195–197° C.

Compound 91

7-Dimethylsulfamoyl-1,2,3,3a,4,5-hexahydrobenzo[e]pyrrolo[2,1-c]-1,2,4-thiadiazine-5,5-dioxide 2-Aminobenzenesulfonamide was used as starting material for the following transformation sequence: Method E (using 4-chlorobutanoyl chloride), Method A (using dimethylamine as amine), Method F (using LiAlH$_4$ and rt.). M.p. 240–243° C.

Compound 92

7-Methylsulfamoyl-1,2,3,5-tetrahydrobenzo[e]pyrrolo[2,1-c]-1,2,4-thiadiazine-5,5-dioxide 2-Aminobenzenesulfonamide was used as starting material for the following transformation sequence: Method E (using 4-chlorobutanoyl chloride), Method A (using methylamine as amine). M.p. 244–247° C.

Compound 93

7-Dimethylsulfamoyl-1,2,3,5-tetrahydrobenzo[e]pyrrolo[2,1-c]-1,2,4-thiadiazine-5,5-dioxide 2-Aminobenzenesulfonamide was transformed by Method E (using 4-chlorobutanoyl chloride) and Method A (using dimethylamine). M.p. 251–253° C.

Compound 94

7-Cyclohexylsulfamoyl-1,2,3,5-tetrahydrobenzo[e]pyrrolo[2,1-c]-1,2,4-thiadiazine-5,5-dioxide 2-Aminobenzenesulfonamide was used as starting material for the following transformation sequence: Method E (using 4-chlorobutanoyl chloride), Method A (using cyclohexylamine as amine). M.p. 151–153° C.

Compound 95

7-(1',2',3',6'-Tetrahydropiperidino)sulfonyl-1,2,3,5-tetrahydrobenzo[e]pyrrolo[2,1-c]-1,2,4-thiadiazine-5,5-dioxide 2-Aminobenzenesulfonamide was used as starting material for the following transformation sequence: Method E (using 4-chlorobutanoyl chloride), Method A (using 1,2,3,6-tetrahydropyridine as amine). M.p. 204–206° C.

Compound 96

3-Bicyclo[2.2.1]hept-5'-en-2'-yl-5,7-dimethyl-1,2,3,4-tetrahydro-1,2,4-benzothiadiazine-1,1-dioxide 2,4-Dimethylaniline was used as starting material for the following transformation sequence: Method B, Method G [using a racemic endo/exo mixture of bicyclo[2.2.1]hept-5-ene-2-carboxaldehyde. Column chromatography gave two diastereomeric fractions each being a mixture of two diastereomers]. Isomeric mixture A, m.p. 160–165° C; isomeric mixture B, m.p. 182–187° C.

Compound 97

3-Cyclohexyl-7-(N,N-diethylsulphamoyl)-5-methyl-1,2,3,4-tetrahydro-1,2,4-benzothiadiazine-1,1-dioxide 3-Cyclohexyl-7-(N,N-diethylsulphamoyl)-5-formyl-1,2-dihydro-1,2,4-benzothiadiazine-1,1-dioxide: 2-Aminobenzenesulfonamide was used as starting material for the following transformation sequence: Method E (using cyclohexanecarbonyl chloride) and Method A (using diethylamine as amine). The product from this transformation (0.60 g, 1.5 mmol) dissolved in dry THF (15 ml) at −78° C. was added s-BuLi in cyclohexane (1.3 M, 2.5 ml, 3.2 mmol) under N$_2$. The yellow mixture was stirred for 25 min at −78° C. The reaction was quenched with dry DMF (0.3 ml, 4 mmol) and the mixture was stirred for 20 min at −78° C. The cooling bath was removed and the mixture was allowed to warm to 0° C. Hydrochloric acid (0.5 M, 10 ml) was added and the mixture was extracted with EtOAc (40 ml). The organic layer was washed with brine (10 ml), dried (Na$_2$SO$_4$) and evaporated to dryness. The residue was dissolved in acetone (8 ml). Et$_2$O (30 ml) was added and within few minutes the product crystallises, yielding 0.41 g (64%) of 3-cyclohexyl-7-(N,N-diethylsulphamoyl)-5-formyl-1,2-dihydro-1,2,4-benzothiadiazine-1,1-dioxide as colorless crystals.

3-Cyclohexyl-7-(N,N-diethylsulphamoyl)-5-methyl-1,2,3,4-tetrahydro-1,2,4-benzothiadiazine-1,1-dioxide (97): 3-Cyclohexyl-7-(N,N-diethylsulphamoyl)-5-formyl-1,2-dihydro-1,2,4-benzothiadiazine-1,1-dioxide (0.20 g, 0.46 mmol) was dissolved in 99% EtOH (60 ml). One small drop of concentrated hydrochloric acid was added to ensure fully hydrogenation. The mixture was hydrogenated using Pd/C (10%, 10 mg) at 4 bar pressure for 24 h. The mixture was filtered through a pad of Celite T and evaporated to dryness. The residue was dissolved in EtOAc (50 ml) and washed with water (10 ml), dried (Na$_2$SO$_4$) and evaporated to dryness yielding 0.18 mg (95%) of 3-cyclohexyl-7-(N,N-diethylsulphamoyl)-5-methyl-1,2-dihydro-1,2,4-benzothiadiazine-1,1-dioxide as colorless powder. The product was further transformed by Method F. M.p. 206–208° C.

Compound 98

3-Bicyclo[2.2.1]hept-5'-en-2'-yl-5,7-diphenyl-1,2,3,4-tetrahydro-1,2,4-benzothiadiazine-1,1-dioxide 3,5-Dibromo-2-aminobenzenesulfonamide (see compound 125) was transformed by Method H (using phenylboronic acid) and Method G (using a racemic endo/exo mixture of bicyclo[2.2.1]hept-5-ene-2-carboxaldehyde). M.p. 222–225° C.

Compound 99

3-Bicyclo[2.2.1]hept-5'-en-2'-yl-5,7-disulfamoyl-1,2,3,4-tetrahydro-1,2,4-benzothiadiazine-1,1-dioxide 2-Aminobenzenesulfonamide was transformed by Method A (using 25% NH$_3$ (aq.) as amine) and Method G (using using a racemic endo/exo mixture of bicyclo[2.2.1]hept-5-ene-2-carboxaldehyde). M.p. 172–180° C.

Compound 100

3-Bicyclo[2.2.1]hept-5'-en-2'-yl-5,7-dichloro-1,2,3,4-tetrahydro-1,2,4-benzothiadiazine-1,1-dioxide 2,4-Dichloroaniline was transformed by Method B and Method G (using a racemic endo/exo mixture of bicyclo[2.2.1]hept-5-ene-2-carboxaldehyde. The product was isolated as a diastereomeric mixture). M.p. 149–151° C.

Compound 101

5-Bromo-3-cyclohexyl-7-sulfamoyl-1,2,3,4-tetrahydro-1,2,4-benzothiadiazine-1,1-dioxide 2-Amino-5-sulfamoylbenzenesulfonamide: A stirred suspension of 2-amino-4-chloro-5-sulfamoylbenzenesulfonamide (11.4 g; 40 mmol) and 10% Pd/C (750 mg) in EtOH (300 ml) was hydrogenated at 1 bar until hydrogen consumption ceased (24 h). The reaction mixture was evaporated to dryness, resuspended in THF and filtered through celite. The filtrate was evaporated to dryness and the isolated solid washed with boiling EtOAc (2×150 ml) to give 9.58 g (95%) product.

2-Amino-3-bromo-5-sulfamoylbenzenesulfonamide: A stirred solution of 2-amino-5-sulfamoylbenzenesulfonamide (3.77 g; 15 mmol) in AcOH (50 ml) was added a solution of $Br_2$ (0.78 ml; 15 mmol) in AcOH (10 ml). The reaction mixture was heated to 70° C. for 6 days, evaporated to dryness, resuspended in MeOH (85 ml) and added solid KOH (3.8 g; 68 mmol). The reaction mixture was heated to 60° C. for 2.5 h (hydrolysis of 3-methyl-, 3-bromomethyl-, 3-dibromomethyl and 3-tribromomethyl-1,2-dihydro-1,2,4-benzothiadiazine isomers formed in situ), filtered, neutralized and evaporated to dryness. Column chromatography gave 3.1 g (63%) product.

5-Bromo-3-cyclohexyl-7-sulfamoyl-1,2,3,4-tetrahydro-1,2,4-benzothiadiazine-1,1-dioxide (101): 2-Amino-3-bromo-5-sulfamoylbenzenesulfonamide was transformed by Method G (using cyclohexanecarboxaldehyde). M.p. 254–258° C.

Compound 102

2-Bicyclo[2.2.1]hept-5'-en-2'-yl-6,8-dibromo-1,2,3,4-tetrahydroquinazoline

2-Amino-3,5-dibromobenzylamine: A mixture of 2-aminobenzylamine (6.1 g; 50 mmol) in $CHCl_3$ (100 ml) at 0°C. was added a solution $Br_2$ (5.1 ml; 100 mmol) in $CHCl_3$ (45 ml) such that the reaction temperature was kept below +2° C. Cooling was then removed and the reaction mixture was stirred at rt. over night. The reaction mixture was filtered and the precipitate washed with EtOAc and purified by column chromatography.

2-Bicyclo[2.2.1]hept-5'-en-2'-yl-6,8-dibromo-1,2,3,4-tetrahydroquinazoline (102): 2-Amino-3,5-dibromobenzylamine was transformed by Method G (using a racemic endo/exo mixture of 2-norbornencarboxaldehyde). M.p. 240° C.

Compound 103

2-Bicyclo[2.2.1]hept-5'-en-2'-yl-6,8-dibromo-4-oxo-1,2,3,4-tetrahydroquinazoline 3,5-Dibromoanthranilamide: A stirred suspension of anthranilamide (13.6 g; 0.1 mol) in AcOH (350 ml) was added a solution of $Br_2$ (10.3 ml; 0.2 mol). The reaction mixture was stirred at 45° C. for 120° C., poured into $H_2O$ (1.5 l) and filtered. Recrystalization (including a warm filtration) from 96% EtOH (approx. 1 l) gave 23.6 g (80%) product.

2-Bicyclo[2.2.1]hept-5'-en-2'-yl-6,8-dibromo-4-oxo-1,2,3,4-tetrahydroquinazoline (103): 3,5-Dibromoanthranilamide was transformed by Method G (using using a racemic endo/exo mixture of bicyclo[2.2.1]hept-5-ene-2-carboxaldehyde). The product was separated into to individual diastereomeric mixtures. M.p. (A) 213–215° C., M.p. (B) 209–210° C.

Compound 104

3-Bicyclo[2.2.1]hept-5'-en-2'-yl-5,7-dibromo-1,2,3,4-tetrahydro-1,2,4-benzothiadiazine-1,1-dioxide 2-Amino-3,5-dibromobenzenesulfonamide (see compound 125) was transformed by Method G (using a racemic endo/exo mixture of bicyclo[2.2.1]hept-5-ene-2-carboxaldehyde). The diastereomeric mixture was purified by column chromatography to give three of the theoretically four possible diastereomers. M.p. (A) 202–206° C., M.p. (B) 196–199° C., M.p. (C) 180–184° C.

Compound 105

5,7-Dibromo-3-bicyclo[2.2.1]heptan-2'-yl-1,2,3,4-tetrahydro-1,2,4-benzothiadiazine-1,1-dioxide Bicyclo[2.2.1]heptane-2-carboxaldehyde: A stirred suspension of 2-norbornylmethanol (0.5 ml; 5.8 mmol) and PCC on $Al_2O_3$* in $CH_2Cl_2$ (25 ml) was stirred at 2–3° C. for 1 h and then allowed to slowly warm up to rt. The reaction mixture was filtered and the solid material washed with $CH_2Cl_2$ (2×25 ml). The combined organic fractions were adsorbed onto silica and chromatographed to give 300 mg (42%) product as an oil.

*[see Cheng Y.-S, Liu W.-L. and Chen S.-H., *Synthesis*, (1980) 223.]

5,7-Dibromo-3-norbornanyl-1,2,3,4-tetrahydro-1,2,4-benzothiadiazine-1,1-dioxide (105): 2-Amino-3,5-dibromobenzenesulfonamide (see compound 125) was transformed by Method G (using bicyclo[2.2.1]heptane-2-carboxaldehyde). M.p. 182–183° C.

Compound 106

3-Cyclohexyl-5,7-dibromo-1,2,3,4-tetrahydro-1,2,4-benzothiadiazine-1,1-dioxide

2-Amino-3,5-dibromobenzenesulfonamide (see compound 125) was transformed by Method G (using cyclohexanecarboxaldehyde). M.p.166–167° C.

Compound 107

3-Adamantyl-5,7-dibromo-1,2,3,4-tetrahydro-1,2,4-benzothiadiazine-1,1-dioxide

1-Adamantanecarboxaldehyde: 1-Adamantylmethanol was oxidized by the method used for 2-norbornylmethanol (see compound 105)*.

*[see Cheng Y.-S, Liu W.-L. and Chen S.-H., *Synthesis*, (1980) 223.]

3-Adamantyl-5,7-dibromo-1,2,3,4-tetrahydro-1,2,4-benzothiadiazine-1,1-dioxide (107): 2-Amino-3,5-dibromobenzenesulfonamide (see compound 125) was transformed by Method G (using 1-adamantylcarboxaldehyde). M.p. 270–273° C.

Compound 108

3-Phenyl-5,7-dibromo-1,2,3,4-tetrahydro-1,2,4-benzothiadiazine-1,1-dioxide

2-Amino-3,5-dibromobenzenesulfonamide (see compound 125) was transformed by Method G (using benzaldehyde). M.p. 186–189° C.

Compound 109

3-Ethoxy-5,7-dibromo-1,2,3,4-tetrahydro-1,2,4-benzothiadiazine-1,1-dioxide

A stirred mixture of 2-amino-3,5-dibromobenzenesulfonamide (see compound 125) (666 mg; 2 mmol), ethylorthoformiate (15 ml; 90 mmol) and $H_2SO_4$ (0.05 ml) was refluxed over night. The reaction mixture was evaporated to dryness and subjected to column chromatography. M.p. 96–98° C.

Compound 110

3-Methyl-5,7-dibromo-1,2-dihydro-1,2,4-benzothiadiazine-1,1-dioxide

A stirred solution of 2-amino-3,5-dibromobenzenesulfonamide (see compound 125) (660 mg; 2 mmol) was refluxed in $Ac_2O$ (25 ml; 265 mmol) over night. The reaction mixture was poured onto ice and filtered. The isolated solid was washed with $Et_2O$. M.p. 287–289° C.

Compound 111

3-Cyclohexyl-6-methyl-7-(2'-pyridyl)-1,2,3,4-tetrahydro-1,2,4-benzothiadiazine-1,1-dioxide To a solution of t-BuLi (1.7 M in pentane, 25 ml, 42 mmol) in dry THF at −78° C. was added 2-bromopyridine (1.9 ml, 20 mmol) in such a rate that the temperature did not exceed −70° C. The mixture was stirred for another 30 min at −78° C. A solution of $ZnCl_2$ (2M in THF, 30 ml, 60 mmol) was added slowly and the cooling bath was removed and warmed to 20° C. 5-Iodo-2-aminobenzenesulfonamide (see compound 37) (1.0 g, 3.2 mmol) and $Pd(PPh_3)_4$ (0.3 g, 8 mol %) was added and the mixture was refluxed for 6 h. The THF was evaporated and the residue was treated with EDTA (53 g, 0.18 mol) and made slightly basic (pH≈8–9) with 1 M NaOH followed by extraction with EtOAc (3×100 ml), drying ($Na_2SO_4$). The organic layer was concentrated to ca. 40 ml and n-hexane was added slowly. The product was filtered off, yielding 0.72 g (87%) of 2-amino-4-methyl-5-(2-pyridyl)-1-benzenesulfonamide as light-yellow crystals. The product was further transformed by Method G (using cyclohexanecarboxaldehyde). M.p. 229–231° C.

Compound 112

3-Cyclohexyl-6-methyl-7-(4'-triazolyl)-1,2,3,4-tetrahydro-1,2,4-benzothiadiazine-1,1-dioxide 5-Iodo-4-methyl-2-aminobenzenesulfonamide: m-Toluidine was transformed by method B and the two isomers separated by column chromatography to give 4-methyl-2-aminobenzenesulfonamide.
A stirred suspension of 4-methyl-2-aminobenzenesulfonamide (620 mg; 3.3 mmol) in $CHCl_3$ (7 ml) at 0° C. was added a solution of iodine monochloride (1.6 g; 9.9 mmol) in $CHCl_3$ (7 ml). The reaction mixture was stirred at 0° C. until H-NMR indicated full conversion of starting material. The reaction mixture was filtered and the isolated solid washed with small volumes of $CHCl_3$, $NaHCO_3$ (sat. aq.), $H_2O$ and air dried to give 640 mg (62%) of product.

3-Cyclohexyl-6-methyl-7-(4'-triazolyl)-1,2,3,4-tetrahydro-1,2,4-benzothiadiazine-1,1-dioxide (112): 5-Iodo-4-methyl-2-aminobenzenesulfonamide was transformed by Method I (using trimethylsilylacetylene) and Method G (using cyclohexanecarboxaldehyde). FAB+ 348. $^1$H-NMR (DMSO-$d_6$): 8.0 (1H; br); 7.65 (1H; br); 7.25 (1H; s); 7.22 (1H; s); 6.95 (1H; br); 6.8 (1H; s); 4.45 (1H; dd); 2.35 (3H; s); 1.95–1.8 (2H; m); 1.8–1.6 (3H; m); 1.3–1.0 (6H; m).

Compound 113

3-Cyclohexyl-6-methyl-7-sulfamoyl-1,2,3,4-tetrahydro-1,2,4-benzothiadiazine-1,1-dioxide N-Acetyl-3-methylaniline: m-Toluidine (10 ml; 93 mmol) was added to a stirred solution of acetic anhydride (30 ml). The reaction mixture was stirred for 1.5 h at rt., evaporated to dryness, stirred with $H_2O$ and filtered to give 13 g product (94%).
3-Cyclohexyl-6-methyl-7-sulfamoyl-1,2,3,4-tetrahydro-1,2,4-benzothiadiazine-1,1-dioxide: N-Acetyl-3-methylaniline was transformed by Method A (using 25% $NH_3$ (aq.) as amine. Deacetylation was complete) and Method G (using cyclohexanecarboxaldehyde). M.p. 231–233° C.

Compound 114

3-Cyclopentyl-6-methyl-7-piperidinosulfonyl-1,2,3,4-tetrahydro-1,2,4-benzothia-diazine-1,1-dioxide Cyclopentanecarbonyl chloride: Cyclopentanecarboxylic acid (0.55 ml; 5 mmol) was refluxed in thionylchloride (1 ml) for 3 h. The reaction mixture was cooled to rt., evaporated to dryness and used directly without any purification.
3-Cyclopentyl-6-methyl-7-piperidinosulfonyl-1,2,3,4-tetrahydro-1,2,4-benzothia-diazine-1,1-dioxide (114): m-Toluidine was used as starting material for the following transformation sequence: Method B [2-amino-6-methylbenzenesulfonamide was separated from 2-amino-4-methylbenzenesulfonamide by recrystallization (EtOAc/hexane)], Method E (using cyclopentanecarbonyl chloride), Method A (using piperidine as amine), Method F. M.p. 229–230° C.

Compound 115

3-Cyclohexyl-6-methyl-7-morpholinosulfonyl-1,2,3,4-tetrahydro-1,2,4-benzothiadiazine-1,1-dioxide m-Toluidine was used as starting material for the following transformation sequence: Method B [2-amino-6-methylbenzenesulfonamide was separated from 2-amino-4-methylbenzenesulfonamide by recrystallization (EtOAc/hexane)], Method E (using cyclohexanecarbonyl chloride), Method A (using morpholine as amine), Method F. M.p. 268–271° C.

Compound 116

3-Cyclohexyl-6-(2-methoxyphenyl)-7-methyl-1,2,3,4-tetrahydro-1,2,4-benzothiadiazine-1,1-dioxide 3-Bromo-4-methylaniline was transformed by Method B (The isomers were separated by fractional crystallization from MeOH) to give 2-amino4-bromo-5-methylbenzenesulfonamide. A mixture of 2-amino-4-bromo-5-methylbenzenesulfonamide (100 mg, 0.38 mmol), 2-methoxyphenylboronic acid (76 mg, 0.50 mmol), Pd(PPh$_3$)$_2$Cl$_2$ (13 mg, 5 mol %) in 1,2-dimethoxyethane (20 ml) and Na$_2$CO$_3$ (2M, 1 ml, 2 mmol) were refluxed under N$_2$ for 4 h. The solvents were removed under reduced pressure and the residue was treated with saturated NaHCO$_3$ (10 ml) and extracted with EtOAc (2×25 ml). The organic layer was washed with brine (20 ml), dried (Na$_2$SO$_4$) and the solvent was removed under reduced pressure. The product was purified by flash chromatography on SiO$_2$ using EtOAc:n-hexane (1:1, v/v) as eluent, yielding 100 mg (90%) of 2-amino-4-(2-methoxyphenyl)-5-methylbenzenesulfonamide as colorless powder. The product was further transformed by Method G (using cyclohexanecarboxaldehyde). M.p. 172–175° C.

Compound 117

3-Cyclohexyl-6-methoxy-7-piperidinosulfonyl-1,2,3,4-tetrahydro-1,2,4-benzothia-diazine-1,1-dioxide m-Anisidine was used as starting material for the following transformation sequence: Method B [2-amino-6-methoxybenzenesulfonamide was separated from 2-amino-4-methoxybenzenesulfonamide by flash chromatography (EtOAc/hexane)], Method C, Method A (using piperidine as amine), Method D, Method G (using cyclohexanecarboxaldehyde). M.p. 237–240° C.

Compound 118 and Compound 122

3-Cyclohexyl-7,8-ethylenedioxy-1,2,3,4-tetrahydro-1,2,4-benzothiadiazine-1,1-dioxide (122) and 3-cyclohexyl-6,7-ethylenedioxy-1,2,3,4-tetrahydro-1,2,4-benzothiadiazine-1,1-dioxide (118)

6-Amino-1,4-benzodioxane was used as starting material and transformed into a mixture of ethylendioxy-2-aminobenzenesulfonamide isomers by use of Method B. The two isomers were separated by column chromatography.

3-Cyclohexyl-6,7-ethylenedioxy-1,2,3,4-tetrahydro-1,2,4-benzothiadiazine-1,1-dioxide (118): 2-amino-5,6-ethylendioxybenzenesulfonamide was transformed by use of Method G (using cyclohexanecarboxylaldehyde). M.p. 196–200° C.

3-Cyclohexyl-7,8-ethylenedioxy-1,2,3,4-tetrahydro-1,2,4-benzothiadiazine-1,1-dioxide (122): 2-amino-7,8-ethylendioxybenzenesulfonamide was transformed by use of Method G (using cyclohexanecarboxylaldehyde). M.p. 268–270° C.

Compound 119

3-Cyclohexyl-6-chloro-7-sulfamoyl-1,2,3,4-tetrahydro-1,2,4-benzothiadiazine-1,1-dioxide 2-Amino-4-chloro-5-sulfamoylbenzenesulfonamide was transformed by Method G (using cyclohexanecarboxaldehyde). M.p. 274–276° C.

Compound 120

3-Phenyl-6-chloro-7-sulfamoyl-1,2,3,4-tetrahydro-1,2,4-benzothiadiazine-1,1-dioxide 2-Amino-4-chloro-5-sulfamoylbenzenesulfonamide was transformed by Method G (using benzaldehyde). M.p. 235–238° C.

Compound 121

3-Cyclohexyl-6-bromo-7-piperidinosulfonyl-1,2,3,4-tetrahydro-1,2,4-benzothia-diazine-1,1-dioxide m-Bromoaniline was used as starting material for the following transformation sequence: Method B [2-amino-6-bromobenzenesulfonamide was separated from 2-amino-4-bromobenzenesulfonamide by recrystallization (EtOAc/hexane)], Method C, Method A (using piperidine as amine), Method D, Method G (using cyclohexanecarboxaldehyde). M.p. 238–241° C.

Compound 122

See compound 118.

Compound 123

2-cyclohexylmethylamino-5-N,N-dimethylsulfamoylbenzenesulfonamide

2-Aminobenzenesulfonamide was used as starting material for the following transformation sequence: Method E (using cyclohexanecarbonyl chloride), Method A (using dimethylamine as amine), Method F (the reaction mixture was left over night with DIBALH at rt. with stirring). M.p. 123–125° C.

Compound 124

2-Ethylamino-7-(1',2',3',6'-tetrahydropiperidino)sulfonylbenzene sulfonamide

3-Methyl-1,2-dihydro-1,2,4-benzothiadiazine-1,1-dioxide (see compound 73) was transformed by Method A (using 1,2,3,6-tetrahydropyridine as amine) followed by Method F (using LiAlH$_4$ and rt.). M.p. 175–177° C.

Compound 125

2-Amino-3,5-dibromobenzenesulfonamide

A stirred solution of 2-aminobenzenesulfonamide (8.6 g; 50 mmol) in AcOH (100 ml) was slowly added a solution of Br$_2$ (5.13 ml; 100 mmol) in AcOH (20 ml). The reaction mixture was heated to 55° C. for 60 h, poured into ice water (800 ml), filtered, adsorbed onto silica and purified by column chromatography to give 11.1 g (67%) product. M.p. 165–169° C.

Compound 126

2-Acetamidobenzenesulfonamide

A stirred solution of 2-aminobenzenesulfonamide (1.72 g; 10 mmol) and triethylamine (1.53 ml; 11 mmol) in THF (25 ml) at 0° C. was added AcCl (0.85 ml; 12 mmol) and left with stirring at rt. over night. The reaction mixture was filtered and adsorbed onto silica. Column chromatography gave 1.7 g (79%) product. M.p. 153.5–155.5° C.

Compound 127

3-Isobutyl-8-(piperidinosulfonyl)-2,3,4,5-tetrahydro-1,2,5-benzothiadiazepine-1,1-dioxide N-(3'-Methyl-1'-carboxybutyl)-2-nitrobenzenesulfonamide: A solution of 2-nitrobenzenesulfonylchloride (11 g; 50 mmol) and NaOH (2.1 g; 53 mmol) in H$_2$O (100 ml) was added DL-leucine (6.55 g; 50 mmol) and left over night with stirring at rt. The reaction mixture was added 4 M NaOH (12.5 ml) and filtered. The filtrate was acidified with 1 M HCl (50 ml) and extracted with EtOAc. The combined organic fractions were dried (Na$_2$SO$_4$) and evaporated to dryness to give 6.7 g (42%) product.

3-Isobutyl-4-oxo-2,3,4,5-tetrahydro-1,2,5-benzothiadiazepine-1,1-dioxide: A stirred suspension of N-(3'-methyl-1'-carboxybutyl)-2-nitrobenzenesulfonamide (6.7 g; 21.2 mmol) and 10% Pd/C (200 mg) in abs. EtOH was hydrogenated at 1 bar. The reaction mixture was filtered through celite and evaporated to dryness. A solution of the crude product in dry THF (50 ml) at 0° C. was added N-hydroxysuccinimide (2.53 g; 22 mmol) and DCC (4.54 g; 22 mmol). The reaction mixture was slowly warmed to rt. and left with stirring over night. The reaction mixture was filtered and the solid material was washed with THF. The combined organic fractions were evaporated to dryness and the remanense added H$_2$O and extracted with EtOAc. The combined organic fractions were dried (Na$_2$SO$_4$) and evaporated to dryness to give 3 g (53%) product.

3-Isobutyl-8-piperidinosulfonyl-2,3,4,5-tetrahydro-1,2,5-benzothiadiazepine-1,1-dioxide: A solution of 3-isobutyl-4-oxo-2,3,4,5-tetrahydro-1,2,5-benzothiadiazepine-1,1-dioxide (500 mg; 1.8 mmol) in dry THF (20 ml) under N$_2$ at 0° C. was added a solution of 2M BH$_3$•SMe$_2$ (9.2 ml; 18 mmol) in THF. After complete addition, the reaction mixture was warmed to rt. and then to reflux for 2 h. The reaction mixture was cooled to rt. and carefully quenched by addition of 6 M HCl (15 ml). The reaction mixture was made strongly alkaline by addition of 7.5 M NaOH (aq.) and extracted by EtOAc. The combined organic fractions were dried (Na$_2$SO$_4$) and evaporated to dryness to yield 320 mg (70%) product. The product was transformed by Method A (using piperidine as amine). M.p. 209–211° C.

Compound 128

3-Cyclohexyl-8-(piperidinosulfonyl)-2,3,4,5-tetrahydro-1,2,5-benzothiadiazepine-1,1-dioxide DL-Cyclohexylglycine: A solution of NaCN (15.9 g; 0.32 mol) in H$_2$O (60 ml) was added NH$_4$Cl (17 g; 0.32 mol) followed by a solution of cyclohexanecarboxaldehyde (37 ml; 0.31 mol) in MeOH (60 ml). The reaction mixture was stirred vigorously for 2 h at rt. The reaction mixture was diluted with H$_2$O (100 ml) and extracted with toluene (2×70 ml). The combined organic phases were washed with H$_2$O (2×50 ml) and extracted with 6 M HCl (2×90 ml). The acidic aqueous phase and the precipitate, which formed upon acidification, were combined and refluxed for 24 h. The reaction mixture was cooled to rt. and made slightly alkaline (using 25% NH$_3$ (aq.)). The precipitate formed, was isolated by filtration, washed with cold H$_2$O and air dried to yield 13 g (26%) of the free amino acid.

Compound 128 was synthesized by the method used for compound 127 (using DL-cyclohexylglycine as amino acid).

Compound 129

3-Cyclohexyl-7-cyclopentylsulfinyl-1,2,3,4-tetrahydro-1,2,4-benzothiadiazine-1,1-dioxide 2-Amino-5-cyclopentylthiobenzenesulfonamide: A mixture of 5-iodo-2-aminobenzenesulfonamide (1.192 g; 4 mmol), triethylamine (750 µl; 10 mmol), CuI (76 mg; 0.4 mmol); cyclopentylmercaptane (590 µl; 6 mmol) and Pd(PPh$_3$)$_4$ (462 mg; 0.4 mmol) in dry dioxane (10 ml) under N$_2$ was stirred in a screw cap ampule at 130° C. over night. The reaction mixture was cooled to rt., diluted with H$_2$O, made alkaline (using 4 M NaOH) and filtered through celite. The filtrate was neutralized to pH 8.5 and evaporated to dryness. Column chromatography gave 327 mg (30%) product.

3-Cyclohexyl-7-cyclopentylsulfinyl-1,2,3,4-tetrahydro-1,2,4-benzothiadiazine-1,1-dioxide (129): 2-Amino-5-cyclopentylthiobenzenesulfonamide was ring brominated (3-position) and S-oxidized under the conditions described by Ali and Bohnert (*Synthesis*, (1998) 1238), using 2 equivalents of Br$_2$. The product was reduced at 1 bar using 5% Pd/C in 96% EtOH and transformed by Method G (using cyclohexanecarboxaldehyde).

The following table summarises the compounds described:

| No. | G$^1$ | G$^2$ | bond type | R$^2$ | R$^3$ | R$^4$ | R$^5$ | R$^6$ | R$^7$ | R$^8$ |
|---|---|---|---|---|---|---|---|---|---|---|
| | | | | 3-monosubstituted compounds with ring single bonds | | | | | | |
| 1 | C=O | N | Single | H | cyclohexyl | H | H | H | H | H |
| 2 | C=O | N | Single | H | phenyl | H | H | H | H | H |
| 3 | C=O | O | Single | H | CH$_3$ | — | H | H | H | H |
| 4 | C=O | O | Single | H | phenyl | — | H | H | H | H |
| 5 | SO$_2$ | N | Single | H | *norbornyl* | H | H | H | H | H |
| 6 | SO$_2$ | N | Single | H | phenyl | H | H | H | H | H |
| | | | | 2,3-disubstituted compounds with ring single bonds | | | | | | |
| 7 | SO$_2$ | N | Single | *cyclopentyl* | | H | H | H | H | H |

-continued

| No. | G¹ | G² | bond type | R² | R³ | R⁴ | R⁵ | R⁶ | R⁷ | R⁸ |
|---|---|---|---|---|---|---|---|---|---|---|
| | | | | | 3,3-disubstituted compounds with ring single bonds | | | | | |
| 8 | C=O | O | Single | H | CH₃, CH₂CH₃ | — | H | H | H | H |
| | | | | | 3,6-disubstituted compounds with ring single bonds | | | | | |
| 9 | SO₂ | N | Single | H | cyclohexyl | H | H | 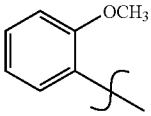 | H | H |
| 10 | SO₂ | N | Single | H | cyclohexyl | H | H | 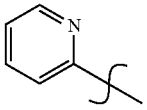 | H | H |
| 11 | SO₂ | N | Single | H | cyclohexyl | H | H | 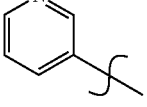 | H | H |
| | | | | | 3,7-disubstituted compounds with ring single bonds | | | | | |
| 12 | SO₂ | N | Single | H | cyclohexyl | H | H | H | 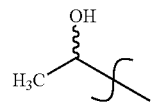 | H |
| 13 | SO₂ | N | Single | H | cyclohexyl | H | H | H | 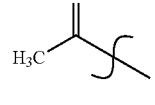 | H |
| 14 | SO₂ | N | Single | H | cyclohexyl | H | H | H | 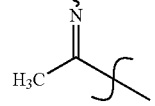 | H |
| 15 | SO₂ | N | Single | H | cyclohexyl | H | H | H | 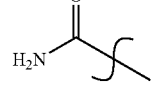 | H |
| 16 | SO₂ | N | Single | H | cyclohexyl | H | H | H | 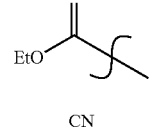 | H |
| 17 | SO₂ | N | Single | H | cyclohexyl | H | H | H | CN | H |
| 18 | SO₂ | N | Single | H |  | H | H | H | phenyl | H |
| 19 | SO₂ | N | Single | H | cyclohexyl | H | H | H | 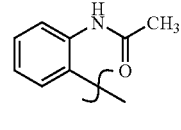 | H |

-continued

| No. | G¹ | G² | bond type | R² | R³ | R⁴ | R⁵ | R⁶ | R⁷ | R⁸ |
|---|---|---|---|---|---|---|---|---|---|---|
| 20 | SO₂ | N | Single | H | cyclohexyl | H | H | H | 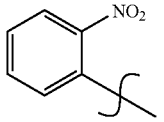 | H |
| 21 | SO₂ | N | Single | H | cyclohexyl | H | H | H | 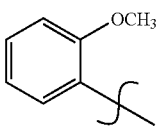 | H |
| 22 | SO₂ | N | Single | H | cyclohexyl | H | H | H | 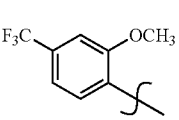 | H |
| 23 | SO₂ | N | Single | H | cyclohexyl | H | H | H | 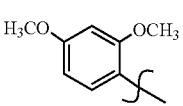 | H |
| 24 | SO₂ | N | Single | H | cyclohexyl | H | H | H | 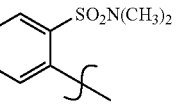 | H |
| 25 | SO₂ | N | Single | H | cyclohexyl | H | H | H | 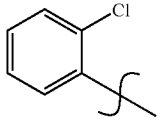 | H |
| 26 | SO₂ | N | Single | H | cyclohexyl | H | H | H | 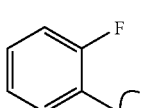 | H |
| 27 | SO₂ | N | Single | H | cyclohexyl | H | H | H | 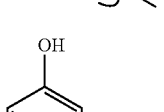 | H |
| 28 | SO₂ | N | Single | H | cyclohexyl | H | H | H | 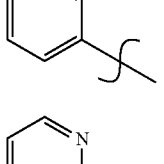 | H |
| 29 | SO₂ | N | Single | H | cyclohexyl | H | H | H | 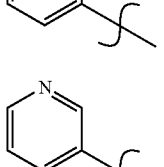 | H |
| 30 | SO₂ | N | Single | H | cyclohexyl | H | H | H | 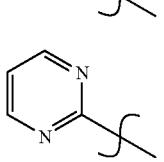 | H |
| 31 | SO₂ | N | Single | H | cyclohexyl | H | H | H | 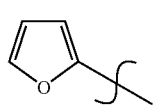 | H |

-continued

| No. | G¹ | G² | bond type | R² | R³ | R⁴ | R⁵ | R⁶ | R⁷ | R⁸ |
|---|---|---|---|---|---|---|---|---|---|---|
| 32 | SO₂ | N | Single | H | cyclohexyl | H | H | H | 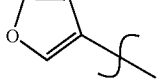 | H |
| 33 | SO₂ | N | Single | H | cyclohexyl | H | H | H | 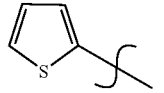 | H |
| 34 | SO₂ | N | Single | H | cyclohexyl | H | H | H | 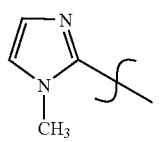 | H |
| 35 | SO₂ | N | Single | H | cyclohexyl | H | H | H | 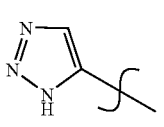 | H |
| 36 | SO₂ | N | Single | H | cyclohexyl | H | H | H | 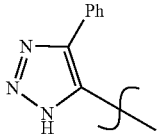 | H |
| 37 | SO₂ | N | Single | H | cyclohexyl | H | H | H | 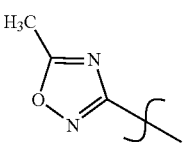 | H |
| 38 | SO₂ | N | Single | H | cyclohexyl | H | H | H | CH₃CONH | H |
| 39 | SO₂ | N | Single | H | cyclohexyl | H | H | H | CH₃SO₂NH | H |
| 40 | SO₂ | N | Single | H | cyclohexyl | H | H | H | O₂N | H |
| 129 | SO₂ | N | single | H | cyclohexyl | H | H | H | 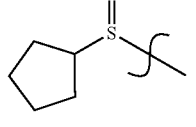 | H |
| 41 | SO₂ | N | Single | H | cyclohexyl | H | H | H | PhSO₂ | H |
| 42 | CH₂ | N | Single | H | cyclohexyl | H | H | H | H₂NSO₂ | H |
| 43 | C=O | N | Single | H | cyclohexyl | H | H | H | H₂NSO₂ | H |
| 44 | SO₂ | N | Single | H | cyclohexyl | H | H | H | H₂NSO₂ | H |
| 45 | SO₂ | N | Single | H | CH₃ | H | H | H | 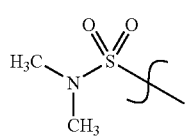 | H |
| 46 | CH₂ | N | Single | H | cyclohexyl | H | H | H | 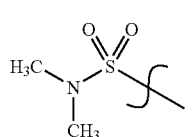 | H |
| 47 | SO₂ | N | Single | H | cyclohexyl | H | H | H | 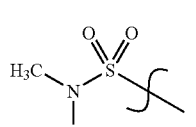 | H |

-continued
| No. | G¹ | G² | bond type | R² | R³ | R⁴ | R⁵ | R⁶ | R⁷ | R⁸ |
|---|---|---|---|---|---|---|---|---|---|---|
| 48 | SO₂ | N | Single | H | cyclohexyl | H | H | H | 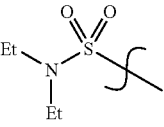 | H |
| 49 | SO₂ | N | Single | H | cyclohexyl | H | H | H | 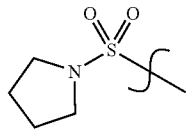 | H |
| 50 | SO₂ | N | Single | H | CH₃ | H | H | H | 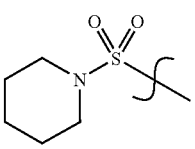 | H |
| 51 | SO₂ | N | Single | H | cyclopropyl | H | H | H | 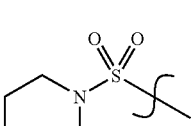 | H |
| 52 | SO₂ | N | Single | H | isopropyl | H | H | H | 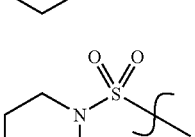 | H |
| 53 | SO₂ | N | Single | H | propyl | H | H | H | 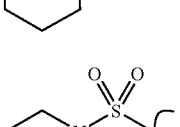 | H |
| 54 | SO₂ | N | Single | H | CH₂Ph | H | H | H | 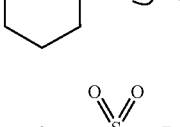 | H |
| 55 | SO₂ | N | Single | H | cyclopentyl | H | H | H | 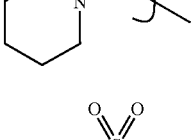 | H |
| 56 | SO₂ | N | Single | H | cyclohexyl | H | H | H | 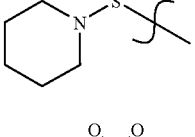 | H |
| 57 | SO₂ | N | Single | H |  | H | H | H | 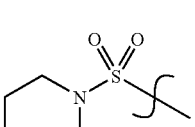 | H |

-continued

| No. | G¹ | G² | bond type | R² | R³ | R⁴ | R⁵ | R⁶ | R⁷ | R⁸ |
|---|---|---|---|---|---|---|---|---|---|---|
| 58 | SO₂ | N | Single | H | cyclohexyl | H | H | H |  | H |
| 59 | SO₂ | N | Single | H | cyclohexyl | H | H | H |  | H |
| 60 | SO₂ | N | Single | H | cyclohexyl | H | H | H |  | H |
| 61 | SO₂ | N | Single | H | cyclohexyl | H | H | H |  | H |
| 62 | SO₂ | N | Single | H | cyclohexyl | H | H | H |  | H |
| 63 | SO₂ | N | Single | H | cyclohexyl | H | H | H |  | H |
| 64 | SO₂ | N | Single | H | cyclohexyl | H | H | H | Br | H |
| | | | | | 3,7-disubstituted compounds with ring double bonds | | | | | |
| 65 | C=O | N | double undef. | (H) | CH₃ | (H) | H | H |  | H |
| 66 | C=O | N | double undef. | (H) | CF₃ | (H) | H | H | H₂NSO₂ | H |
| 67 | C=O | N | double undef. | (H) | CF₃ | (H) | H | H |  | H |
| 68 | C=O | N | double undef. | (H) | CF₃ | (H) | H | H |  | H |
| 69 | C=O | N | double undef. | (H) | CF₃ | (H) | H | H |  | H |

-continued

| No. | G¹ | G² | bond type | R² | R³ | R⁴ | R⁵ | R⁶ | R⁷ | R⁸ |
|---|---|---|---|---|---|---|---|---|---|---|
| 70 | C=O | N | double undef. | (H) | CF₃ | (H) | H | H | morpholine-N-SO₂– | H |
| 71 | C=O | N | double undef. | (H) | cyclohexyl | (H) | H | H | H₂NSO₂ | H |
| 72 | SO₂ | N | double undef. | (H) | CH₃ | (H) | H | H | H₂NSO₂ | H |
| 73 | SO₂ | N | double undef. | (H) | CH₃ | (H) | H | H | (CH₃)₂NSO₂– | H |
| 74 | SO₂ | N | double undef. | (H) | CH₃ | (H) | H | H | 3,6-dihydro-2H-pyridin-1-yl-SO₂– | H |
| 75 | SO₂ | N | double undef. | (H) | CH₃ | (H) | H | H | 3-methoxyphenyl– | H |
| 76 | SO₂ | N | double undef. | (H) | CF₃ | (H) | H | H | (CH₃)₂NSO₂– | H |
| 77 | SO₂ | N | double undef. | (H) | CF₃ | (H) | H | H | HOSO₂ | H |
| | | | | | 3,8-disubstituted compounds with ring single bonds | | | | | |
| 78 | SO₂ | N | Single | H | cyclohexyl | H | H | H | H | CH₃ |
| 79 | SO₂ | N | Single | H | cyclohexyl | H | H | H | H | CH₂OH |
| 80 | SO₂ | N | Single | H | cyclohexyl | H | H | H | H | 2-methoxyphenyl– |
| 81 | SO₂ | N | Single | H | cyclohexyl | H | H | H | H | 3-methoxyphenyl– |
| 82 | SO₂ | N | Single | H | cyclohexyl | H | H | H | H | pyridin-2-yl– |
| 83 | SO₂ | N | Single | H | cyclohexyl | H | H | H | H | OCH₃ |
| | | | | | 5,7-disubstituted compounds with ring double bonds | | | | | |
| 84 | SO₂ | N | double undef. | (H) | H | (H) | Br | H | Br | H |

-continued

| No. | G¹ | G² | bond type | R² | R³ | R⁴ | R⁵ | R⁶ | R⁷ | R⁸ |
|---|---|---|---|---|---|---|---|---|---|---|
| | | | | | 2,3,7-trisubstituted compounds with ring single bonds | | | | | |
| 85 | SO₂ | N | Single | CH₃ | cyclohexyl | H | H | H | 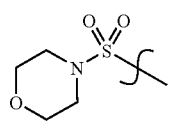 | H |
| | | | | | 3,4,7-trisubstituted compounds with ring single bonds | | | | | |
| 86 | SO₂ | N | Single | H | cyclohexyl | CH₃ | H | H | 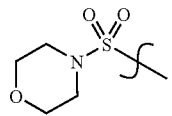 | H |
| 87 | SO₂ | N | Single | H |  | | H | H | CH₃SO₂NH | H |
| 88 | SO₂ | N | Single | H |  | | H | H | H₂NSO₂ | H |
| 89 | SO₂ | N | Single | H |  | | H | H | 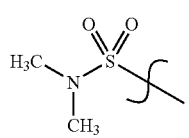 | H |
| 90 | SO₂ | N | Single | H |  | | H | H | 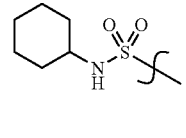 | H |
| 91 | SO₂ | N | Single | H |  | | H | H | 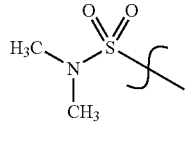 | H |
| | | | | | 3,4,7-trisubstituted compounds with ring double bonds | | | | | |
| 92 | SO₂ | N | double 2,3 | — |  | | H | H | 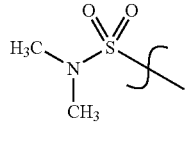 | H |
| 93 | SO₂ | N | double 2,3 | — |  | | H | H | 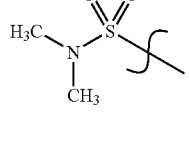 | H |

-continued

| No. | G¹ | G² | bond type | R² | R³ | R⁴ | R⁵ | R⁶ | R⁷ | R⁸ |
|---|---|---|---|---|---|---|---|---|---|---|
| 94 | SO$_2$ | N | double 2,3 | — | (cycloheptyl structure) | | H | H | (N-cyclohexyl sulfonamide structure) | H |
| 95 | SO$_2$ | N | double 2,3 | — | (cycloheptyl structure) | | H | H | (tetrahydropyridinyl sulfonamide structure) | H |

3,5,7-trisubstituted compounds with ring single bonds

| No. | G¹ | G² | bond type | R² | R³ | R⁴ | R⁵ | R⁶ | R⁷ | R⁸ |
|---|---|---|---|---|---|---|---|---|---|---|
| 96 | SO$_2$ | N | Single | H | (norbornenyl) | H | CH$_3$ | H | CH$_3$ | H |
| 97 | SO$_2$ | N | Single | H | cyclohexyl | H | CH$_3$ | H | (N,N-diethyl sulfonamide structure) | H |
| 98 | SO$_2$ | N | Single | H | (norbornenyl) | H | phenyl | H | phenyl | H |
| 99 | SO$_2$ | N | Single | H | (norbornenyl) | H | H$_2$NSO$_2$ | H | H$_2$NSO$_2$ | H |
| 100 | SO$_2$ | N | Single | H | (norbornenyl) | H | Cl | H | Cl | H |
| 101 | SO$_2$ | N | Single | H | cyclohexyl | H | Br | H | H$_2$NSO$_2$ | H |
| 102 | CH$_2$ | N | Single | H | (norbornenyl) | H | Br | H | Br | H |
| 103 | C=O | N | Single | H | (norbornenyl) | H | Br | H | Br | H |
| 104 | SO$_2$ | N | Single | H | (norbornenyl) | H | Br | H | Br | H |
| 105 | SO$_2$ | N | Single | H | (norbornenyl) | H | Br | H | Br | H |
| 106 | SO$_2$ | N | Single | H | cyclohexyl | H | Br | H | Br | H |
| 107 | SO$_2$ | N | Single | H | (adamantyl) | H | Br | H | Br | H |
| 108 | SO$_2$ | N | Single | H | phenyl | H | Br | H | Br | H |
| 109 | SO$_2$ | N | Single | H | OCH$_2$CH$_3$ | H | Br | H | Br | H |

-continued

| No. | G¹ | G² | bond type | R² | R³ | R⁴ | R⁵ | R⁶ | R⁷ | R⁸ |
|---|---|---|---|---|---|---|---|---|---|---|
| | | | | | 3,5,7-trisubstituted compounds with ring double bonds | | | | | |
| 110 | SO₂ | N | double undef. | (H) | CH₃ | (H) | Br | H | Br | H |
| | | | | | 3,6,7-trisubstituted compounds with ring single bonds | | | | | |
| 111 | SO₂ | N | Single | H | cyclohexyl | H | H | CH₃ | 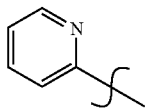 | H |
| 112 | SO₂ | N | Single | H | cyclohexyl | H | H | CH₃ | 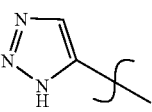 | H |
| 113 | SO₂ | N | Single | H | cyclohexyl | H | H | CH₃ | H₂NSO₂ | H |
| 114 | SO₂ | N | Single | H | cyclopentyl | H | H | CH₃ | 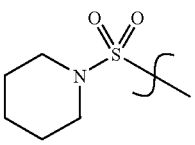 | H |
| 115 | SO₂ | N | Single | H | cyclohexyl | H | H | CH₃ | 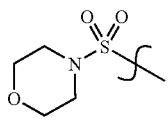 | H |
| 116 | SO₂ | N | Single | H | cyclohexyl | H | H | 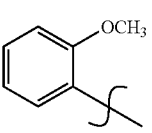 | CH₃ | H |
| 117 | SO₂ | N | Single | H | cyclohexyl | H | H | OCH₃ | 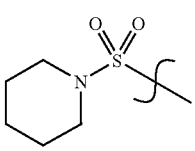 | H |
| 118 | SO₂ | N | Single | H | cyclohexyl | H | H | 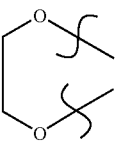 | | H |
| 119 | SO₂ | N | Single | H | cyclohexyl | H | H | Cl | H₂NSO₂ | H |
| 120 | SO₂ | N | Single | H | phenyl | H | H | Cl | H₂NSO₂ | H |
| 121 | SO₂ | N | Single | H | cyclohexyl | H | H | Br | 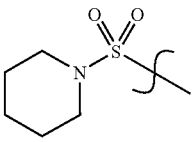 | H |

-continued

| No. | G¹ | G² | bond type | R² | R³ | R⁴ | R⁵ | R⁶ | R⁷ | R⁸ |
|---|---|---|---|---|---|---|---|---|---|---|
| 3,7,8-trisubstituted compounds with ring single bonds | | | | | | | | | | |
| 122 | SO₂ | N | Single | H | cyclohexyl | H | H | | H | 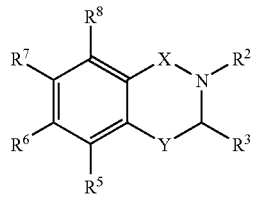 |

The invention claimed is:

1. A 1,2,4-benzothiadiazine derivative of the formula:

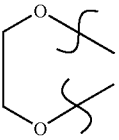

wherein
$R^3$ represents cycloalkyl; and
$R^4$ represents hydrogen; and
$R^5$ represents hydrogen; and
$R^6$ represents hydrogen or alkyl; and
$R^7$ represents —SO₂—NR¹⁷R¹⁸, wherein $R^{17}$ and $R^{18}$ independently of each another represent hydrogen or alkyl, or $R^{17}$ and $R^{18}$ together with the nitrogen to which they are attached form a heterocyclic 3- to 8-membered ring structure, which ring structure is optionally substituted with alkyl; and
$R^8$ represents hydrogen or alkyl.

2. The 1,2,4-benzothiadiazine derivative of claim 1, wherein $R^7$ represents —SO₂—NR¹⁷R¹⁸, wherein $R^{17}$ and $R^{18}$ independently represent hydrogen or alkyl.

3. The 1,2,4-benzothiadiazine derivative of claim 1, wherein
$R^3$ represents cycloalkyl; and
$R^4$ represents H; and
$R^5$ represents H; and
$R^6$ represents hydrogen or alkyl; and
$R^7$ represents —SO₂—NR¹⁷R¹⁸, wherein $R^{17}$ and $R^{18}$ independently represent hydrogen or alkyl, or $R^{17}$ and $R^{18}$ together with the nitrogen to which they are attached form a heterocyclic 3- to 8-membered ring structure, which ring structure is optionally substituted with alkyl; and
$R^8$ represents alkyl.

4. The 1,2,4-benzothiadiazine derivative of claim 1, wherein $R^3$ represents cyclopentyl or cyclohexyl.

5. The 1,2,4-benzothiadiazine derivative of claim 1, wherein $R^6$ represents hydrogen or methyl.

6. The 1,2,4-benzothiadiazine derivative of claim 1, wherein $R^7$ represents N,N-dimethylsulfamoyl, N,N-diethylsulfamoyl, or —SO₂-heterocyclic ring, wherein the heterocyclic ring is selected from the group of piperidine, pyrrolidine, 1,2,5,6-tetrahydropyridine, N-methylpiperazine, N-sulfonylmethyl-piperazine, and morpholine.

7. The 1,2,4-benzothiadiazine derivative of claim 1, wherein
$R^3$ represents cyclohexyl; and
$R^7$ represents N,N-dimethylsulfamoyl; and
$R^5$, $R^4$, $R^6$, and $R^8$ all represent hydrogen.

8. The 1,2,4-benzothiadiazine derivative according to claim 1, said compound being:
3-Cyclohexyl-7-(N,N-diethylamino)sulfonyl-1,2,3,4-tetrahydro-1,2,4-benzothiadiazine-1,1-dioxide;
3-Cyclohexyl-7-pyrrolidinosulfonyl-1,2,3,4-tetrahydro-1,2,4-benzothiadiazine-1,1-dioxide;
3-Cyclopropyl-7-piperidinosulfonyl-1,2,3,4-tetrahydro-1,2,4-benzothiadiazine-1,1-dioxide;
3-Cyclopentyl-7-piperidinosulfonyl-1,2,3,4-tetrahydro-1,2,4-benzothiadiazine-1,1-dioxide;
3-Cyclohexyl-7-piperidinosulfonyl-1,2,3,4-tetrahydro-1,2,4-benzothiadiazine-1,1-dioxide;
3-Cyclohexyl-7-(1',2',3',6'-tetrahydropiperidino)sulfonyl-1,2,3,4-tetrahydro-1,2,4-benzothiadiazine-1,1-dioxide;
3-Cyclohexyl-7-(4'-methylpiperazino)sulfonyl-1,2,3,4-tetrahydro-1,2,4-benzothiadiazine-1,1-dioxide;
3-Cyclohexyl-7-(4'-methylsulfonylpiperazino)sulfonyl-1,2,3,4-tetrahydro-1,2,4-benzothiadiazine-1,1-dioxide;
3-Cyclohexyl-7-morpholinosulfonyl-1,2,3,4-tetrahydro-1,2,4-benzothiadiazine-1,1-dioxide;
3-Cyclopentyl-6-methyl-7-piperidinosulfonyl-1,2,3,4-tetrahydro-1,2,4-benzothia-diazine-1,1-dioxide;
3-Cyclohexyl-6-methyl-7-morpholinosulfonyl-1,2,3,4-tetrahydro-1,2,4-benzothiadiazine-1,1-dioxide; or
3-Cyclohexyl-7-sulfamoyl-1,2,3,4-tetrahydro-1,2,4-benzothiadiazine-1,1-dioxide;
or a pharmaceutical acceptable salt thereof.

9. A pharmaceutical composition comprising an effective amount of a 1,2,4-benzothiadiazine derivative according to claim 1, or a pharmaceutically acceptable salt thereof, or a pharmaceutically acceptable excipient, carrier or diluent.

10. A method of treating a disorder or disease of a living animal body, including a human, which disorder or disease is responsive to modulation of the AMPA receptor complex of the central nervous system wherein the disorder or disease is selected from psychotic disorders, sexual dysfunction, intellectual impairment disorders, and depression, which method comprises administration of a therapeutically effective amount of a 1,2,4-benzothiadiazine derivative according to claim 1.

11. The 1,2-4-benzothiadiazine derivative of claim 8, which is 3-cyclopentyl-6-methyl-7-piperidinosulfonyl-1,2,3,4-tetrahydro-1,2,4-benzothiadiazine-1,1-dioxide; or a pharmaceutically acceptable salt thereof.

* * * * *